(12) United States Patent
Hainfeld

(10) Patent No.: US 7,906,147 B2
(45) Date of Patent: Mar. 15, 2011

(54) FUNCTIONAL ASSOCIATIVE COATINGS FOR NANOPARTICLES

(75) Inventor: James F. Hainfeld, Shoreham, NY (US)

(73) Assignee: Nanoprobes, Inc., Yaphank, NY (US)

( * ) Notice: Subject to any disclaimer, the term of this patent is extended or adjusted under 35 U.S.C. 154(b) by 0 days.

(21) Appl. No.: 11/549,071

(22) Filed: Oct. 12, 2006

(65) Prior Publication Data

US 2008/0089836 A1 Apr. 17, 2008

(51) Int. Cl.
*A61K 9/16* (2006.01)
(52) U.S. Cl. .................................................. 424/490
(58) Field of Classification Search .................. None
See application file for complete search history.

(56) References Cited

U.S. PATENT DOCUMENTS

| | | | |
|---|---|---|---|
| 4,094,804 A * | 6/1978 | Shimoiizaka | 252/62.52 |
| 5,360,895 A | 11/1994 | Hainfeld et al. | |
| 5,443,813 A | 8/1995 | Hainfeld | |
| 5,521,289 A | 5/1996 | Hainfeld et al. | |
| 5,690,903 A | 11/1997 | Hainfeld | |
| 6,001,054 A | 12/1999 | Regulla et al. | |
| 6,121,425 A | 9/2000 | Hainfeld et al. | |
| 6,369,206 B1 | 4/2002 | Leone et al. | |
| 6,521,773 B1 | 2/2003 | Hainfeld | |
| 6,534,039 B2 | 3/2003 | Hainfeld | |
| 6,645,464 B1 | 11/2003 | Hainfeld | |
| 6,660,058 B1 * | 12/2003 | Oh et al. | 75/351 |
| 6,818,199 B1 | 11/2004 | Hainfeld et al. | |
| 6,955,639 B2 | 10/2005 | Hainfeld et al. | |
| 2007/0031505 A1 * | 2/2007 | Roy et al. | 424/490 |
| 2007/0051202 A1 * | 3/2007 | Raghuraman et al. | 75/370 |

OTHER PUBLICATIONS

Swami et al, Formation of Water-Dispersible Gold Nanoparticles Using a Technique Based on Surface-Bound Interdigitated Bilayers, Langmuir, 2003, 19, 1168-1172.*
Shen et al, Bilayer Surfactant Stabilized Magnetic Fluids: Synthesis and Interactions at Interfaces, Langmuir, 1999, 15, 447-453.*
Patil et al, Surface Derivatization of Colloidal Silver Particles Using Interdigitated Bilayers: A Novel Strategy for Electrostatic Immobilization of Colloidal Particles in Thermally Evaporated Fatty Acid/Fatty Amine Films, Langmuir, 1998, 14, 2707-2711.*
Fan et al, Self-Assembly of Ordered, Robust, Three-Dimensional Gold Nanocrystal/Silica Arrays, Science, 2004, 304, 567-571.*
Zhang et al, Didodecyldimethylammonium Bromide Lipid Bilayer-Protected Gold Nanoparticles: Synthesis, Characterization, and Self-Assembly, Langmuir, 2006, 22, 2838-2843.*
Daniel, M.C. and Astruc, D., "Gold Nanoparticles: Assembly, Supramolecular Chemistry, Quantum-Size-Related Properties, and Applications toward Biology, Catalysis, and Nanotechnology," Chem. Rev. 104:293-346 (2004).
Hoeben, Freek J.M. et al., "About Supramolecular Assemblies of π-Conjugated Systems," Chem Rev. 105:1491-1546 (2005).
Love, J.C. et al., "Self-Assembled Monolayers of Thiolates on Metals as a Form of Nanotechnology," Chem. Rev. 105:1103-1169 (2005).
Goodman et al., "Surfactant layering on mixed monolayer-protected gold clusters," Colloids and Surfaces B:Biointerfaces 39:119-123 (2004).
Nikoobakht et al., "Evidence for Bilayer Assembly of Cationic Surfactants on the Surface of Gold Nanorods," Langmuir 17:6368-6374 (2001).
Patil et al., "Evidence for Novel Interdigitated Bilayer Formation of Fatty Acids during Three-Dimensional Self-Assembly on Silver Colloidal Particles," J. Am. Chem. Soc. 119:9281-9282 (1997).
Patil et al., "Role of Particle Size in Individual and Competitive Diffusion of Carboxylic Acid Derivatized Colloidal Gold Particles in Thermally Evaporated Fatty Amine Films," Langmuir 15:8197-8206 (1999).
Sastry et al., "Phase transfer of aqueous colloidal gold particles into organic solutions containing fatty amine molecules," Colloids and Surfaces A: Physicochemical and Engineering Aspects 181:255-259 (2001).
Sastry et al., "Langmuir-Blodgett Films of Carboxylic Acid Derivatized Silver Colloidal Particles: Role of Subphase pH on Degree of Cluster Incorporation," J. Phys. Chem. B 101:4954-4958 (1997).
Simard, J. et al., "Formation and pH-controlled assembly of amphiphilic gold nanoparticles," Chem. Commun., 2000, 1943-1944.

* cited by examiner

*Primary Examiner* — Michael G Hartley
*Assistant Examiner* — Paul Dickinson
(74) *Attorney, Agent, or Firm* — Wilson Sonsini Goodrich & Rosati

(57) ABSTRACT

Described herein are nanoparticles that are coated with a bilayer of molecules formed from surface binding molecules and amphiphatic molecules. The bilayer coating self assembles on the nanoparticles from readily available materials/molecules. The modular design of the bilayer coated nanoparticles provides a means for readily and efficiently optimizing the properties of the bilayer coated nanoparticle compositions. Also described herein are uses of such nanoparticles in medicine, laboratory techniques, industrial and commercial applications.

14 Claims, 8 Drawing Sheets

Test Tube 1.   Test Tube 2.                Test Tube 3.   Test Tube 4.

FUNCTIONAL ASSOCIATIVE COATINGS FOR NANOPARTICLES

FIELD OF THE INVENTION

Nanoparticles, coated nanoparticles, methods of making nanoparticles, methods of making coated nanoparticles, methods of coating nanoparticles and methods of use thereof are disclosed.

BACKGROUND OF THE INVENTION

Nanoparticles have properties that are valuable in a variety of applications, such as in biology, chemistry, materials science, and medicine. The usefulness of the nanoparticles is limited by their stability and/or toxicity. The nature of the coating on nanoparticles influences the physical and chemical behavior of the nanoparticle. The coating on a nanoparticle determines the surface properties of the coated nanoparticle.

SUMMARY OF THE INVENTION

Provided herein are nanoparticles that are coated with a bilayer of molecules formed from surface binding molecules and amphiphatic molecules. The bilayer coating self assembles on the nanoparticles from readily available materials/molecules. The modular design of the bilayer coated nanoparticles provides a means for readily and efficiently optimizing the properties of the bilayer coated nanoparticle compositions.

Provided herein are nanoparticles, coated nanoparticles, methods of making nanoparticles and coated nanoparticles, and methods of use thereof. In one embodiment, provided herein is a composition including: a nanoparticle coated with a bilayer of molecules, wherein said bilayer of molecules is formed from:
  a layer of surface binding molecules in direct contact with the nanoparticle, wherein the surface binding molecules include:
    (i) a hydrophobic moiety; and
    (ii) a moiety that has an affinity for the nanoparticle; and
  (b) a layer of amphiphatic molecules;
wherein the layer of surface binding molecules of (a) and the layer of amphiphatic molecules of (b) are held together by hydrophobic interactions.

In some embodiments, the layer of surface binding molecules of (a) forms a complete monolayer that coats the nanoparticle.

In some embodiments, the hydrophobic interactions are selected from among van der Waals forces, $\pi$-$\pi$ stacking interactions, and London Dispersion forces.

The hydrophobic region of the bilayer coating that includes the hydrophobic moieties of the surface binding molecules and the hydrophobic moieties, of the amphiphatic molecules provides a physical barrier to the nanoparticle. In some embodiments, the hydrophobic region of the bilayer coating that includes the hydrophobic moieties of the surface binding molecules and the hydrophobic moieties of the amphiphatic molecules prevents water, metals, ions, and other charged species from interacting with the nanoparticle.

For any and all of the embodiments, attributes or components of the compositions can be selected from among a subset of the listed alternatives. For example, in some embodiments, compositions provided herein include a nanoparticle with a diameter of about 1 nm up to about 200 nm. In some embodiments, compositions provided herein include a nanoparticle with a diameter of about 3 nm up to about 200 nm. In other embodiments, compositions provided herein include a nanoparticle with a diameter of about 1 nm up to about 100 nm. In some other embodiments, compositions provided herein include a nanoparticle that has a diameter of about 1 nm up to about 40 nm.

In one embodiment, compositions provided herein include a nanoparticle selected from among inorganic metals, inorganic metal halides, inorganic metal oxides, inorganic metal sulfides, mixed metal clusters, inorganic metal nitrides, metal alloys, ceramics, semiconductors, magnetic nanoparticles, and heteropolyanion nanoparticles. In other embodiments, compositions provided herein include a nanoparticle selected from among inorganic metals, inorganic metal halides, inorganic metal oxides, metal alloys, ceramics, semiconductors, and magnetic nanoparticles. In some other embodiments, compositions provided herein include a nanoparticle selected from among inorganic metals, inorganic metal halides, and magnetic nanoparticles.

In some embodiments, compositions provided herein include a nanoparticle which includes at least one metal selected from among scandium, titanium, vanadium, chromium, manganese, iron, cobalt, nickel, copper, zinc, yttrium, zirconium, niobium, molybdenum, ruthenium, rhodium, palladium, silver, cadmium, hafnium, tantalum, tungsten, rhenium, osmium, iridium, platinum, gold, gadolinium, aluminum, gallium, indium, tin, thallium, lead, bismuth, magnesium, calcium, strontium, barium, lithium, sodium, potassium, boron, silicon, phosphorus, germanium, arsenic, antimony, and combinations thereof. In other embodiments, compositions provided herein include a nanoparticle that includes at least one metal selected from among scandium, titanium, vanadium, chromium, manganese, iron, cobalt, nickel, copper, zinc, yttrium, zirconium, niobium, molybdenum, ruthenium, rhodium, palladium, silver, cadmium, hafnium, tantalum, tungsten, rhenium, osmium, iridium, platinum, gold, aluminum, gallium, indium, tin, thallium, lead, bismuth and combinations thereof. In some other embodiments, compositions provided herein include a nanoparticle that includes at least one metal selected from among titanium, vanadium, chromium, manganese, iron, cobalt, nickel, copper, zinc, zirconium, molybdenum, ruthenium, rhodium, palladium, silver, cadmium, tungsten, rhenium, osmium, iridium, platinum, gold, aluminum, bismuth, and combinations thereof. In some embodiments, compositions provided herein include a nanoparticle that includes a metal selected from among iron and gold. In some embodiments, compositions provided herein include a nanoparticle that includes gold. In other embodiments, compositions provided herein include a nanoparticle that includes iron.

In one embodiment, the binding moiety of the surface binding molecules of (a) includes a neutral moiety or a charged moiety. In some embodiments, the binding moiety of the surface binding molecules of (a) has an affinity for the nanoparticle that results in an ionic interaction, a covalent bond, or coordination with the nanoparticle.

In some embodiments, the binding moiety of the surface binding molecules of (a) is selected from among a thiol moiety, a thiolate moiety, an alcohol moiety, an alkoxide moiety, a carboxyl moiety, a carboxylate moiety, an amine moiety, an amine oxide moiety, a phosphine moiety, a phosphine oxide moiety, a phosphonate moiety, a phosphinite moiety, a silane moiety, a sulfonate moiety, a sulfate moiety, and combinations thereof. In some other embodiments, the binding moiety of the surface binding molecules of (a) is selected from among a thiol moiety, a thiolate moiety, an alcohol moiety, an alkoxide moiety, a carboxyl moiety, a carboxylate moiety, an amine moiety, a phosphine moiety, a phosphine oxide moiety, a phosphonate moiety, a phosphinite moiety, a silane moiety, and combinations thereof. In other embodiments, the binding moiety of the surface binding molecules of (a) is selected from among a thiol moiety, a thiolate moiety, an alcohol moiety, an alkoxide moiety, a carboxyl moiety, a carboxylate moiety, an amine moiety, a silane moiety, and combinations thereof. In one embodiment, the binding moiety of the surface binding molecules of (a) is selected from among a thiol moiety and a thiolate moiety.

In some embodiments, the hydrophobic moiety of the surface binding molecules of (a) is selected from among alkyl moieties, alkene moieties, alkyne moieties, aryl moieties, hydrophobic moieties of fatty acids or lipids, steroid moieties, and combinations thereof. In other embodiments, the hydrophobic moiety of the surface binding molecules of (a) is selected from among alkyl moieties, alkene moieties, hydrophobic moieties of fatty acids or lipids, and combinations thereof.

In one embodiment, the surface binding molecules of (a) are selected from among alkyl thiols, alkyl amines, alcohols, and carboxylic acids. In some embodiments, the surface binding molecules are selected from among alkyl thiols and fatty acids. In some embodiments the surface binding molecules are selected from among ($C_8$-$C_{20}$)alkyl thiols and ($C_8$-$C_{20}$) alkyl fatty acids.

In one aspect, the surface binding molecules of (a) are selected from among dodecanethiol, octanethiol, decanethiol, hexadecylthiol, octadecylthiol, thiophenol, aminothiophenol, triphenylphosphine, tributylphosphine, tri(dodecyl)phosphine, dodecylamine, phenyldimethylsilyl chloride, dimethyl-n-octadecylchlorosilane, hexadecyldichlorosilane, and cetyl alcohol. In another aspect, the surface binding molecules of (a) are selected from among dodecanethiol, octanethiol, octadecylthiol, dodecylamine, and cetyl alcohol. In yet another aspect, the surface binding molecules of (a) are selected from among dodecanethiol and octadecylthiol.

In some embodiments, the surface binding molecules of (a) are all identical or all derived from moieties having the same structure.

In some embodiments, the layer of amphiphatic molecules of (b) increases the water solubility of the nanoparticle coated with the layer of surface binding molecules of (a). In some embodiments, the layer of amphiphatic molecules of (b) increases biocompatibility of the nanoparticle coated with the layer of surface binding molecules of (a). In some other embodiments, the layer of amphiphatic molecules of (b) increases the water solubility and biocompatibility of the nanoparticle coated with the layer of surface binding molecules of (a). In other embodiments, the amphiphatic molecules of (b) include a hydrophobic moiety selected from among alkyl moieties, alkene moieties, alkyne moieties, aryl moieties, hydrophobic moieties of fatty acids, lipids, steroid moieties, and combinations thereof. In some embodiments, the amphiphatic molecules of (b) include a hydrophobic moiety that is compatible with the hydrophobic moiety of the surface binding molecules of (a) such that the hydrophobic interactions between the layer of surface binding molecules and the layer of amphiphatic molecules is maximized. In some embodiments, the amphiphatic molecules of (b) include a hydrophobic moiety that is compatible with the hydrophobic moiety of the surface binding molecules of (a) such that the hydrophobic interactions between the layer of surface binding molecules and the layer of amphiphatic molecules is considerable and holds the two layers together non-covalently.

In some embodiments, the amphiphatic molecules of (b) include a hydrophilic moiety selected from among phosphate groups, sulfonate groups, sulfate groups, hydroxyl groups, carboxyl groups, amino groups, amide groups, carbohydrate groups, peptide groups, protein groups, nucleic acid groups, ethylene glycol groups, and combinations thereof.

In some embodiments, the amphiphatic molecules of (b) are selected from among detergents, soaps, emulsifiers, surfactants, saturated fatty acids, unsaturated fatty acids, bile salts, monoglycerides, diglycerides, phospholipids, glycerophospholipids, sphingolipids, sterol lipids, sugar-linked lipids (glycolipids), protein linked lipids, and derivatives thereof. In other embodiments, the ampiphatic molecules of (b) are selected from among sorbitan monolaurate, polyoxyethylene (20) sorbitan monolaurate (Tween® 20), sorbitan monopalmitate, polyoxyethylene (20) sorbitan monopalmitate (Tween® 40), sorbitan monostearate, polyoxyethylene (20) sorbitan monostearate (Tween® 60), sorbitan monooleate, and polyoxyethylene (20) sorbitan monooleate (Tween® 80). In some other embodiments, the ampiphatic molecules of (b) are selected from among phosphatidic acid, phosphatidylcholine, phosphatidylserine, phosphatidylglycerol, phosphatidylethanolamine, phosphatidylinositol, and bisphosphatidyl glycerol. In yet some other embodiments, the ampiphatic molecules of (b) are selected from among sodium dodecylsulfate, sodium cholate, sodium deoxycholate, taurocholic acid, N-lauroylsarcosine sodium salt, lauryldimethylamine-oxide, cetyltrimethylammonium bromide, and bis(2-ethylhexyl)sulfosuccinate sodium salt. In other embodiments, the ampiphatic molecules of (b) are selected from among butyric acid, lauric acid (dodecanoic acid), myristic acid (tetradecanoic acid), palmitic acid (hexadecanoic acid), stearic acid (octadecanoic acid), arachidic acid (eicosanoic acid), linolenic acid, alpha-linolenic acid, docosahexaenoic acid, eicosapentaenoic acid, linolenic acid, arachidonic acid, oleic acid, erucic acid, stearidonic acid, eicosatetraenoic acid, gamma-linolenic acid, dihomogamma-linolenic acid, arachidonic acid, and alkali metal salts thereof.

In some embodiments, all ampiphatic molecules of (b) are identical or derived from moieties having the same chemical structure.

In some embodiments, provided herein is a method of solubilizing nanoparticles in hydrophilic media that includes:
coating the nanoparticles with a bilayer of molecules, wherein said bilayer includes:
(a) a layer of surface binding molecules in direct contact with the nanoparticle, wherein the surface binding molecules include:
(i) a hydrophobic moiety; and
(ii) a binding moiety that has an affinity for the nanoparticle; and
(b) a layer of amphiphatic molecules;
wherein the layer of surface binding molecules of (a) and the layer of ampiphatic molecules of (b) are held together by hydrophobic interactions.

In some embodiments, surface binding molecules and amphiphatic molecules self assemble into a bilayer coating on the nanoparticle. In some embodiments, the compositions provided herein self assemble. In some embodiments, surface binding molecules self assemble a complete monolayer on the nanoparticle. In some embodiments, amphiphatic molecules self assemble a layer on the nanoparticle that is coated with a layer of surface binding molecules.

Also provided herein is a method of reducing the apparent toxicity of a nanoparticle to a mammal, wherein said method includes coating the nanoparticle with a bilayer of molecules, wherein said bilayer includes:

(a) a layer of surface binding molecules in direct contact with the nanoparticle, wherein said surface binding molecules include:
  (i) a hydrophobic moiety; and
  (ii) a binding moiety that has an affinity for the nanoparticle; and
(b) a layer of ampiphatic molecules;
wherein the layer of surface binding molecules of (a) and the layer of ampiphatic molecules of (b) are held together by hydrophobic interactions.

In some embodiments, the compositions provided herein include a nanoparticle that can absorb radiation. In some embodiments, the compositions provided herein include a nanoparticle that can absorb radiation selected from among X-ray radiation, infrared radiation, microwave radiation, ultrasound radiation, radiofrequencies, visible electromagnetic radiation, and/or ultraviolet radiation. In some embodiment, the compositions provided herein include a nanoparticle that can absorb X-Ray radiation and/or radiofrequencies. In other embodiments, compositions provided herein include a nanoparticle that an absorb X-ray radiation.

In some embodiments, the compositions provided herein are used in X-ray imaging. In some embodiments, the compositions provided herein are used in X-ray imaging and include gold nanoparticles. In some embodiments, compositions provided herein are used in computer tomography (CT). In some embodiments, compositions provided herein are used in computer tomography (CT) and include gold nanoparticles. In some embodiments, the compositions provided herein are used in magnetic resonance imaging (MRI). In some other embodiments, compositions provided herein are used in magnetic resonance imaging (MRI) and include gold nanoparticles. In other embodiments, compositions provided herein are used in medical applications as a contrast agent. In other embodiments, compositions provided herein are used in cancer therapy to increase and/or direct radiation to tumor cells. In other embodiments, compositions provided herein are used to increase the amount of radiation delivered to tissues and/or cells. In other embodiments, compositions provided herein are used to direct radiation to tissues and/or cells. In some other embodiments, compositions provided herein include a radioisotope of an element that emits radiation, such as, but not limited to, beta radiation.

In some embodiments, provided herein is a composition that includes superparamagnetic nanoparticles of iron coated with a bilayer of molecules, which includes:

(a) a layer of oleic acid in direct contact with the superparamagnetic particles of iron; and
(b) a layer of Tween® 20.

Any combination of the groups described above for the various variables is contemplated herein. For any and all of the embodiments, attributes or components of the compositions can be selected from among a subset of the listed alternatives in order to provide stable compositions.

In another aspect are compositions comprising:
a surface coated with a bilayer of molecules, wherein said bilayer of molecules is formed from:
(a) a layer of surface binding molecules in direct contact with the nanoparticle, comprising:
  (i) a hydrophobic moiety; and
  (ii) a binding moiety that has an affinity for the nanoparticle; and
(b) a layer of amphiphatic molecules;
wherein the layer of surface binding molecules of (a) and the layer of ampiphatic molecules of (b) are held together by hydrophobic interactions.

In a further or alternative embodiment, the layer of surface binding molecules of (a) forms a complete monolayer that coats the surface. In a further or alternative embodiment, the hydrophobic interactions are selected from among van der Waals forces, $\pi$-$\pi$ stacking interactions, and London Dispersion forces.

In a further or alternative embodiment, the binding moiety of the surface binding molecules of (a) comprises a neutral moiety or a charged moiety. In a further or alternative embodiment, the binding moiety of the surface binding molecules of (a) is selected from among a thiol moiety, a thiolate moiety, an alcohol moiety, an alkoxide moiety, a carboxyl moiety, a carboxylate moiety, an amine moiety, an amine oxide moiety, a phosphine moiety, a phosphine oxide moiety, a phosphonate moiety, a phosphinite moiety, a silane moiety, a sulfonate moiety, a sulfate moiety, and combinations thereof. In a further or alternative embodiment, the hydrophobic moiety of the surface binding molecules of (a) is selected from among alkyl moieties, alkene moieties, alkyne moieties, aryl moieties, hydrophobic moieties of fatty acids, steroid moieties, and combinations thereof. In a further or alternative embodiment, the surface binding molecules of (a) are selected from among alkyl thiols, alkyl amines, alcohols, and carboxylic acids. In a further or alternative embodiment, the surface binding molecules of (a) are selected from among dodecanethiol, octanethiol, octadecylthiol, thiophenol, aminothiophenol, triphenylphosphine, tributylphosphine, tri (dodecyl)phosphine, dodecylamine, phenyldimethylsilyl chloride, dimethyl-n-octadecylchlorosilane, hexadecyldichlorosilane, and cetyl alcohol. In a further or alternative embodiment, the surface binding molecules of (a) are selected from among dodecanethiol, octanethiol, octadecylthiol, dodecylamine, and cetyl alcohol. In a further or alternative embodiment, the surface binding molecules of (a) have the same or are derived from the same chemical structure.

In a further or alternative embodiment, the ampiphatic molecules of (b) comprise a hydrophobic moiety selected from among alkyl moieties, alkene moieties, alkyne moieties, aryl moieties, hydrophobic moieties of fatty acids, steroid moieties, and combinations thereof. In a further or alternative embodiment, the ampiphatic molecules of (b) comprise a hydrophilic moiety selected from among phosphate groups, sulfonate groups, sulfate groups, hydroxyl groups, carboxyl groups, amino groups, amide groups, carbohydrate groups, peptide groups, protein groups, nucleic acid groups, ethylene glycol groups, and combinations thereof. In a further or alternative embodiment, the ampiphatic molecules are selected from among detergents, soaps, emulsifiers, surfactants, saturated fatty acids, unsaturated fatty acids, bile salts, monoglycerides, diglycerides, phospholipids, glycerophospholipids, sphingolipids, sterol lipids, sugar-linked lipids (glycolipids), protein linked lipids, and derivatives thereof. In a further or alternative embodiment, the ampiphatic molecules of (b) are selected from among sorbitan monolaurate, polyoxyethylene (20) sorbitan monolaurate (Tween® 20), sorbitan monopalmitate, polyoxyethylene (20) sorbitan monopalmitate (Tween® 40), sorbitan monostearate, polyoxyethylene (20) sorbitan monostearate (Tween® 60), sorbitan monooleate, and polyoxyethylene (20) sorbitan monooleate (Tween® 80). In a further or alternative embodiment, the ampiphatic molecules of (b) are selected from among phosphatidic acid, phosphatidylcholine, phosphatidylserine, phosphatidylglycerol, phosphatidylethanolamine, phosphatidylinositol, and bisphosphatidyl glycerol. In a further or alternative embodiment, the ampiphatic molecules of (b) are selected from among sodium dodecylsulfate, sodium cholate, sodium deoxycholate, taurocholic acid, N-lauroylsarcosine sodium salt, lauryldimethylamine-oxide, cetyltrimethylammonium bromide, and bis(2-ethylhexyl)sulfosuccinate sodium salt. In a further or alternative embodiment, the ampiphatic molecules of (b) are selected from among butyric acid, lauric acid (dodecanoic acid), myristic acid (tetradecanoic acid), palmitic acid (hexadecanoic acid), stearic acid (octadecanoic acid), arachidic acid (eicosanoic acid), linolenic acid, alpha-linolenic acid, docosahexaenoic acid, eicosapentaenoic acid, linolenic acid, arachidonic acid, oleic acid, erucic acid, stearidonic acid, eicosatetraenoic acid, gamma-linolenic acid, dihomo-gamma-linolenic acid, arachidonic acid, and alkali metal salts thereof. In a further or alternative embodiment, the ampiphatic molecules of (b) have the same or are derived from the same chemical structure.

Other objects, features and advantages of the methods and compositions described herein will become apparent from the following detailed description. It should be understood, however, that the detailed description and the specific examples, while indicating specific embodiments, are given by way of illustration only, since various changes and modifications within the spirit and scope of the present disclosure will become apparent to those skilled in the art from this detailed description. All references cited herein, including patents, patent applications, and publications, are hereby incorporated by reference in their entirety.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features are set forth with particularity in the appended claims. A better understanding of the features and advantages of the present disclosure will be obtained by reference to the following detailed description that sets forth illustrative embodiments, in which the principles described herein are utilized, and the accompanying drawings of which:

DETAILED DESCRIPTION

Figure 1:
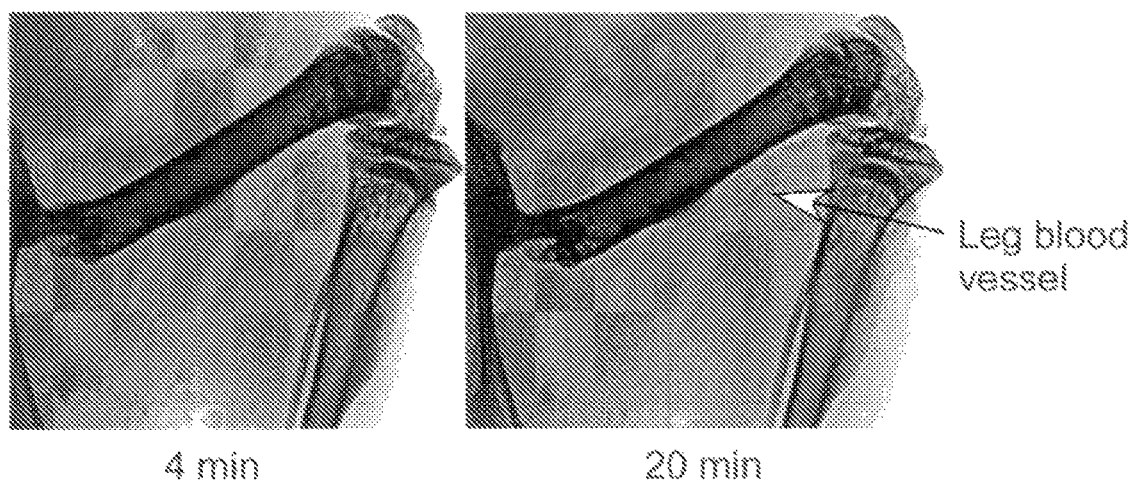
FIG. 1 is an illustrative, non-limiting planar X-ray image of mouse legs after an intravenous injection of bilayer coated 15 nm gold nanoparticles, which were prepared as described in Example 1. Images were acquired after 4 minutes and after 20 minutes of the injection with a Skyscan 1076 microCT unit operating at 41 kVp with no filter. The bilayer coated gold nanoparticles enabled imaging of blood vessels without perceptible decrement over this time period.

Coatings play an important role in industrialized life. They include, but are not limited to, paints, magnetic disks, phosphor screens, non-stick surfaces, reflectors, abrasives, rust inhibitors, water proofing, adhesives, catalytic surfaces, cosmetics, hair products, and many others. Many man-made objects are coated. Some coatings are deposited by drying and other coatings bind to the surface of a substrate from a liquid. Coatings are generally applied to a substrate as a solid, liquid or gas. The attachment to the surface can be by chemical reaction forming covalent bonds with the surface, whereas others are bound by ionic forces, or just physically immobilized on the surface, such as a dried layer that is a solid. Coatings generally function to alter the surface properties of the substrate that is coated. For example, in some cases, coatings function to make a substrate more stable, to make it magnetic, to prevent rust or corrosion, to seal it from water, to make it less sticky or to make it more sticky, to make it catalytic, to change its physical characteristics, such as roughness or smoothness, to change its color or reflectivity, to alter its charge, and/or to make it reactive or inert. In some cases, coatings stabilize surface atoms, and/or modify the electronic states of the atoms that are being coated. In general, a coating adheres to a surface and imparts some desired property to the coated material. The choice of a particular coating generally requires considerations, such as, for example, the nature of the interaction of the coating with the surface of the substrate, and the nature of the interaction of the applied coating with the exterior environment. These two features may be achieved by mixing two or more components in a binder material. Another approach has been to utilize a coating molecule that has two functional ends, one for binding the surface, and the other to present the desired functionality to the environment.

The surface that is created by coatings generally controls the chemical and physical properties of the coated substrate. Coating molecules that have two functional ends connected by a suitable spacer (i.e. bifunctional molecules), one for binding to the surface to be coated and the other that faces the environment, generally require multi-step syntheses, prolonged reaction times, time consuming isolations and purifications. Coating molecules that have two functional ends, one for binding to the surface that is coated and the other to face the environment, generally require complex synthetic methods for their preparation, and require chemical protection of one end of the molecule while the other end is chemically modified. The end result is a more expensive and laborious coating molecule. A considerable amount of effort and resources would be required in order to optimize the properties of a specific coating molecule for a particular substrate surface and/or exterior environment.

Although coatings are important in all aspects of life, there are shortcomings that have not been overcome in some applications. Stability of the coating is frequently an issue, and the surface may need to be recoated, incurring additional effort and expense, as well as yielding a surface with changing properties over its life and possible failure. Expense is also a drawback with many coatings since frequently the best coatings are more difficult to produce or require more expensive materials.

Nanoparticle and nanostructure coatings are important due to their use in, for example:

forming novel materials with improved attributes;

medical applications such as, for example, drugs, diagnostic and therapeutic agents, as drug delivery vehicles;

biomedical studies as labels, as catalysts, in foods and fuels; and incorporation into other coatings.

In in vivo applications, such as, for example, medical applications, the toxicity of nanoparticles and route of clearance from the body are largely determined by the coating on the nanoparticle. Many nanoparticles, even though they have useful physical properties, such as producing a large MRI signal, are not suitable for in vivo use due to their toxicity and poor clearance. Nanoparticles that are used as stains or labels in tissues and/or cells suffer from background binding to undesired molecules and this hinders specific targeting. Gold nanoparticles are used in lateral flow devices for rapid diagnostic tests, but the sensitivity is limited by background binding, flow characteristics, and the binding of the targeting moiety. These properties are largely controlled by the coating on the colloidal gold particles.

Self assembled monolayers (SAMs) are surfaces consisting of a single layer of molecules on a substrate. Rather than having to use a technique such as chemical vapor deposition or molecular beam epitaxy to add molecules to a surface (often with poor control over the thickness of the molecular layer), self assembled monolayers can be prepared simply by adding a solution of the desired molecule onto the substrate surface and washing off the excess. For example, in one embodiment, SAMs of alkane thiols form on gold. Sulfur has particular affinity for gold, with a binding energy in the range of 20-35 kcal/mol. An alkane with a thiol head group will stick to the gold surface and form an ordered assembly with the alkyl chains packing together due to van der Waals forces The initial stage of SAM formation usually takes minutes or less under the normal conditions of 0.1-10 mM thiol concentration in a solvent. More ordering of the assembly can take place over days or months, depending on the molecules involved.

Many other molecules that have surface binding moieties and hydrophobic molecules, such as, but not limited to, alkyl chains, also form SAMs on substrates. However, it may not be desirable to have a coated substrate that has a hydrophobic surface. SAMs may also form from bifunctional molecules, however the properties may not be desirable or may require much time and effort to optimize.

Molecules that include only one of the functionalities described above, i.e. either a surface binding moiety or a moiety that is suitable for facing the environment are known and readily available. Many such molecules also contain a hydrophobic moiety. Provided herein are methods and materials to construct bilayer coatings for surfaces, including planar and curved surfaces and particles and nanoparticles, based on molecules that are or may be pre-associated through non-covalent hydrophobic interactions, wherein some molecules have a moiety that has an affinity for the nanoparticle and some molecules have a hydrophilic moiety that has a preference to face the environment, which in some embodiments is a hydrophilic environment. These coatings can be added to bare surfaces to functionalize them or used in the synthesis of novel nanoparticles. Such coatings can confer unusual stability, provide enhanced reactivity, reduce non-specific binding, and enable economic production.

Previous or currently used methods for optimizing the coatings on nanoparticles involve trying to adsorb a variety of polymers onto the nanoparticle or to try to bind a variety of smaller molecules, which may not possess desired environmental groups to be exposed to the environment. Attempts to find stable combinations often lead to time consuming and/or expensive outcomes and/or unsuccessful outcomes. However, even if a small molecule and/or polymer was found that had a stable interaction with the nanoparticle, there still remains the problem of optimizing the outer surface of the coating to be best suited to a particular environment, and to provide linking groups to bind additional materials or targeting moieties.

Disclosed herein are compositions that include a nanoparticle coat with a bilayer of molecules, wherein the bilayer is or can be formed from inexpensive, and readily available materials. Coatings provided herein are stable, are self-assembled from, in many cases, inexpensive and readily available materials, the properties of the coatings can readily be modified by changing the components of the coatings, the external surface of the coatings can be made multifunctional, the external surface of the coating can be linked to drugs, antibodies, peptides, carbohydrates, lipids, organic compounds, proteins, nucleic acids, metals, plastics, and other materials in a straightforward manner, and the coatings can be biocompatible for use in biological systems and in vivo applications.

In one embodiment, compositions are provided that include a nanoparticle that is coated with a bilayer of molecules. The bilayer that coats the nanoparticle is formed from two types of molecules, wherein each type of molecule has a hydrophobic group. One layer of the bilayer that coats the nanoparticle is formed from surface binding molecules that include: (i) a hydrophobic moiety, (ii) and a binding moiety that has an affinity for the nanoparticle surface that is coated. The surface binding molecules are in direct contact with the nanoparticle surface. The layer of surface binding molecules forms a complete layer on the surface of the nanoparticle. The other layer of the bilayer is formed from amphiphatic molecules, which include both a hydrophobic moiety and a hydrophilic moiety. The hydrophilic moiety of the amphiphatic molecules confers a desirable property to the external environment. In some embodiments, the amphiphatic molecules increase the water solubility of the nanoparticle coated with a complete layer of the surface binding molecules. In some embodiments, the bilayer coating reduces the toxicity of nanoparticles.

In one embodiment, compositions provided herein are formed by combining surface binding molecules and amphiphatic molecules. The two types of molecules become associated due to the interaction of their hydrophobic moieties. The interaction of the hydrophobic moieties of the surface binding molecules with the hydrophobic moieties of the amphiphatic molecules leads to the formation of an intermediate complex, which is characterized as having three domains: 1) the first domain includes the binding moiety of the surface binding molecules; 2) the second domain includes the hydrophobic moieties from both the surface binding molecules and the amphiphatic molecules; and 3) the third domain include the hydrophilic moiety of the amphiphatic molecules. This intermediate complex is then applied to the surface of a nanoparticle, and upon binding, a self-assembling coating is formed from the pre-formed intermediate complex. The hydrophobic domains in the bilayer coating will further interact and bind together, thus strengthening the coating by providing lateral bonding. In an aqueous environment, this hydrophobic layer resists solubilization, thus providing additional stability. A further property of this design is the sealing that this laterally bonded layer provides, making it difficult or impossible for aqueous ions or molecules to penetrate this layer and reach the surface of the nanoparticle. Some aqueous phase molecules and ions can degrade the bare surface of nanoparticles and then continue degrading the underlying bulk material. The compositions and methods provided herein inhibit or prevent such a degradative process by providing an impermeable coating for nanoparticles.

Small water soluble nanoparticles are typically sensitive to disruption by high concentrations of thiols or cyanide or halides ions, whereas the nanoparticles of this disclosure are resistant to this breakdown.

Bilayer coated nanoparticles as provided herein are stable under experiments that test the response of bilayer coated gold nanoparticles to silver enhancement. For example, gold nanoparticles coated by conventional methods can nucleate silver metal deposition on their catalytic surface in the presence of a reducing agent. The gold particle then grows in size. Nanoparticles that are coated with a bilayer of molecules as disclosed herein, the deposition of metal onto the nanoparticle is strongly inhibited, indicating that the catalytic gold surface is not readily accessible to the silver ions and reducing agent. This was found to be also the case with a similar process, gold enhancement, where gold ions are reduced onto the metal surface.

Nanoparticles such as, but not limited to, those that include gold, silver, uranium, platinum, palladium, iridium, tungsten, bismuth, vanadium, cobalt, nickel, iron, aluminium, copper, and gadolinium may be coated using the molecules and methods disclosed herein. Provided herein are bilayer coated nanoparticles that show low non-specific binding, do not aggregate, have very high solubility, and excellent stability. Bilayer coated nanoparticles provided herein are stable and withstand challenges to chemical degradation such as, for example, are stable in boiling solvents such as, for example boiling water, and do not aggregate in high salt solutions such as, for example, 1 M aqueous NaCl. Typically, larger nanoparticles, for example greater than 10 nm have been difficult to stabilize and prevent aggregation and non-specific binding. In some embodiments, 20 nm gold nanoparticles that are coated with the bilayer of molecules disclosed herein show good stability, do not aggregate, are not affected when present in boiling solvents, such as, for example, boiling water, are not affected by exposure to 1M aqueous NaCl and/or are not affected by exposure to 100 mM mercaptoethanol.

It has been observed that highly charged nanoparticles can precipitate proteins, like albumin, or highly charged proteins, such as, for example, lectins and nuclear proteins. However, neutralizing the charged nanoparticle as disclosed herein and rendering the bilayer coated nanoparticle water soluble can prevent precipitation. In some embodiments, charged nanoparticles that are coated with a bilayer coating of molecules as discussed herein provides a water soluble composition that does not precipitate from solution. In some embodiments, coating polyionic nanoparticles with a bilayer of molecules as disclosed herein reduces the toxicity of the nanoparticle in vitro and in vivo.

In some embodiments, 1-50 nm immunogold conjugates that are formed by antibody adsorption, which is a standard technique used to stabilize and functionalize gold particles, show instability when purified and/or isolated upon a single centrifugation and/or multiple centrifugations, wherein aggregation of the gold particles is observed. Gold particles that are coated with the bilayer of molecules as disclosed herein do not show aggregation when purified/isolated by centrifugation(s) and almost complete recovery of the bilayer coated nanoparticles is possible after each centrifugation. In some embodiments, gold particles are coated with a bilayer of molecules as disclosed herein and the bilayer coated gold is then conjugated to an antibody.

Nanoparticles provided herein are or may be coated with a bilayer of molecules formed from readily available molecules. The modular design of the bilayer coatings allows rapid assemblage of the bilayer coatings on nanoparticles and ease in optimizing the features of the bilayer coating, such as, for example, optimizing the interaction of the surface binding molecules with the surface of the nanoparticle, optimizing the hydrophobic interactions between the surface binding molecules and the amphiphatic molecules, which hold the layers of the bilayer together, and optimizing the hydrophilic moieties of the amphiphatic molecules, which present the functional groups to the environment and control the surface properties of the bilayer coated nanoparticle. Although single molecules that have a surface binding moiety, a hydrophobic moiety, and an environmental group could be used to coat nanoparticles, such molecules are not readily available, and/or synthesis is complicated and/or expensive.

Stable compositions are provided herein that include nanoparticles coated with a bilayer of molecules formed from surface binding molecules and amphiphatic molecules. The surface binding molecules form a complete layer and the surface that is coated. The coatings formed by the methods and molecules disclosed herein can produce stable nanoparticles in solution. For example, bilayer coated nanoparticles provided herein are or may be stable when heating an aqueous solution that includes the bilayer coated nanoparticles at 100° C. Nanoparticles that are coated with a bilayer of molecules as disclosed herein are not or may not be affected or degraded when exposed to a 0.1M solution of beta-mercaptoethanol, and the bilayer coated nanoparticles do not or may not show aggregation in high salt solutions, such as, for example, 1M aqueous NaCl. Nanoparticles that are coated with a bilayer of molecules as discussed herein can be purified by repeated centrifugations to form soft pellets, which are easily resuspended in solvents.

Compositions provided herein include a nanoparticle that is coated with a bilayer of molecules, wherein the two layers of molecules are held together by hydrophobic interactions. The bilayer coated nanoparticles are stable; the components of the bilayer can be inexpensive and available in large quantities; the properties of the surface facing the external environment can be flexibly designed; the external surface can be made multifunctional; drugs, antibodies, peptides, carbohydrates, lipids, organic compounds, proteins, nucleic acids, metals, and other materials can be attached to the surface of the bilayer coating in a straightforward manner; the coatings can be biocompatible for use in biological systems and in vivo applications.

Throughout the disclosure, reference will be made to nanoparticles. It will be understood that the methods disclosed herein can be used to coat any surface that has a layer of surface metal atoms. Surfaces include those of flat substrates, curved substrates, surfaces with defects, nanoparticles, and particles.

Certain Terminology

Unless defined otherwise, all technical and scientific terms used herein have the same meaning as is commonly understood by one of skill in the art to which the claimed subject matter belongs. All patents, patent applications, published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

Definition of standard chemistry terms may be found in reference works, including Carey and Sundberg "ADVANCED ORGANIC CHEMISTRY $4^{TH}$ ED." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Standard techniques can be used for recombinant DNA, oligonucleotide synthesis, and tissue culture and transformation (e.g., electroporation, lipofection). Reactions and purification techniques can be performed e.g., using kits of manufacturer's specifications or as commonly accomplished in the art or as described herein.

An "alkoxy" group refers to a (alkyl)O—group, where alkyl is as defined herein.

An "alkyl" group refers to an aliphatic hydrocarbon group. The alkyl moiety may be a "saturated alkyl" group, which means that it does not contain any alkene or alkyne moieties. The alkyl moiety may also be an "unsaturated alkyl" moiety, which means that it contains at least one alkene or alkyne moiety. An "alkene" moiety refers to a group that has at least one carbon-carbon double bond, and an "alkyne" moiety refers to a group that has at least one carbon-carbon triple bond. The alkyl moiety, whether saturated or unsaturated, may be branched, straight chain, or cyclic. Depending on the structure, an alkyl group can be a monoradical or a diradical (i.e., an alkylene group).

As used herein, $C_1$-$C_x$ includes $C_1$-$C_2$, $C_1$-$C_3$ ... $C_1$-$C_x$.

The "alkyl" moiety may have 1 to 30 carbon atoms (whenever it appears herein, a numerical range such as "1 to 30" refers to each integer in the given range; e.g., "1 to 30 carbon atoms" means that the alkyl group may have 1 carbon atom, 2 carbon atoms, 3 carbon atoms, etc., up to and including 30 carbon atoms, although the present definition also covers the occurrence of the term "alkyl" where no numerical range is designated). The alkyl group of the compounds described herein may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from among methyl, ethyl, propyl, iso-propyl, n-butyl, iso-butyl, sec-butyl, and t-butyl. Thus $C_1$-$C_4$ alkyl includes $C_1$-$C_2$ alkyl and $C_1$-$C_3$ alkyl. Alkyl groups can be substituted or unsubstituted. Typical alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, heptyl, octyl, nonyl, decyl, undecyl, dodecyl, tridecyl, tetradecyl, pentadecyl, hexadecyl, heptadecyl, octadecyl, and nonadecyl.

As used herein, the term "non-cyclic alkyl" refers to an alkyl that is not cyclic (i.e., a straight or branched chain containing at least one carbon atom). Non-cyclic alkyls can be fully saturated or can contain non-cyclic alkenes and/or alkynes. Non-cyclic alkyls can be optionally substituted.

The term "alkylamine" refers to the —N(alkyl)$_x$H$_y$ group, where x and y are selected from among x=1, y=1 and x=2, y=0. When x=2, the alkyl groups, taken together with the N atom to which they are attached, can optionally form a cyclic ring system.

An "amide" is a chemical moiety with the formula —C(O) NHR or —NHC(O)R, where R is selected from among alkyl, cycloalkyl, aryl, heteroaryl (bonded through a ring carbon) and heteroalicyclic (bonded through a ring carbon). An amide moiety may form a linkage between an amino acid or a peptide molecule and a compound described herein, thereby forming a prodrug. Any amine, or carboxyl side chain on the compounds described herein can be amidified. The procedures and specific groups to make such amides are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein by reference in its entirety.

The term "aromatic" refers to a planar ring having a delocalized π-electron system containing 4n+2π electrons, where n is an integer. Aromatic rings can be formed by five, six, seven, eight, nine, or more than nine atoms. Aromatics can be optionally substituted. The term "aromatic" includes both carbocyclic aryl (e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, naphthalenyl, phenanthrenyl, anthracenyl, fluorenyl, and indenyl. Depending on the structure, an aryl group can be a monoradical or a diradical (i.e., an arylene group).

The term "carbocyclic" refers to a compound which contains one or more covalently closed ring structures, and that the atoms forming the backbone of the ring are all carbon atoms. The term thus distinguishes carbocyclic from heterocyclic rings in which the ring backbone contains at least one atom which is different from carbon.

The term "bond" or "single bond" refers to a chemical bond between two atoms, or two moieties when the atoms joined by the bond are considered to be part of larger substructure.

As used herein, "non-covalent" interactions refers to interactions that are generally weaker than covalent bonds and include Coulomb interactions, hydrogen bonds, ion-ion interactions, ion-dipole interactions, dipole-dipole interactions, cation-π interactions, π-π interactions, van der Waals forces, London Dispersion Forces, hydrophobic effects and metal ligand coordination (Steed, J. W. Atwood, J. L. Supramolecular Chemistry; Wiley & Sons: Chichester, 2000; Hoeben F. J. M., Jonkhejim, P.; Meijer, E. W., Schenning, A. P. H. J, Chem. Rev. 2005, 105, 1491-1546). Covalent bonds normally have a homolytic bond dissociation energy that ranges between about 100 kJmol$^{-1}$ to about 420 kJmol$^{-1}$.

As used herein, "amphipatic molecules" refers to molecules that contain both a hydrophilic moiety and a hydrophobic moiety. In reference to amphipatic molecules, a hydrophilic group is also referred herein to an environmental group.

The term "cycloalkyl" refers to a monocyclic or polycyclic radical that contains only carbon and hydrogen, and may be saturated, partially unsaturated, or fully unsaturated. Cycloalkyl groups include groups having from 3 to 10 ring atoms. Illustrative examples of cycloalkyl groups include the following moieties:

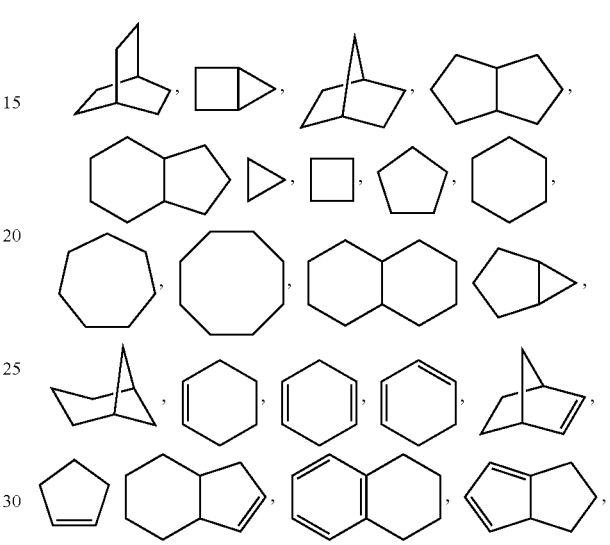

and the like. Depending on the structure, an cycloalkyl group can be a monoradical or a diradical (e.g., an cycloalkylene group).

As used herein, the term "carbocycle" refers to a ring, wherein each of the atoms forming the ring is a carbon atom. Carbocylic rings can be formed by three, four, five, six, seven, eight, nine, or more than nine carbon atoms. Carbocycles can be optionally substituted.

The term "ester" refers to a chemical moiety with formula —COOR, where R is selected from among alkyl, cycloalkyl, aryl, heteroaryl (bonded through a ring carbon) and heteroalicyclic (bonded through a ring carbon). Any hydroxy, or carboxyl side chain on the compounds described herein can be esterified. The procedures and specific groups to make such esters are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein by reference in its entirety.

The term "halo" or, alternatively, "halogen" or "halide" means fluoro, chloro, bromo or iodo.

The terms "haloalkyl," "haloalkenyl," "haloalkynyl" and "haloalkoxy" include alkyl, alkenyl, alkynyl and alkoxy structures in which at least one hydrogen is replaced with a halogen atom. In certain embodiments in which two or more hydrogen atoms are replaced with halogen atoms, the halogen atoms are all the same as one another. In other embodiments in which two or more hydrogen atoms are replaced with halogen atoms, the halogen atoms are not all the same as one another. The terms "fluoroalkyl" and "fluoroalkoxy" include haloalkyl and haloalkoxy groups, respectively, in which the halo is fluorine. In certain embodiments, haloalkyls are optionally substituted.

As used herein, the terms "heteroalkyl" "heteroalkenyl" and "heteroalkynyl" include optionally substituted alkyl, alkenyl and alkynyl radicals in which one or more skeletal chain atoms are selected from an atom other than carbon, e.g., oxygen, nitrogen, sulfur, silicon, phosphorus or combinations thereof.

The term "heteroatom" refers to an atom other than carbon or hydrogen. Heteroatoms are typically independently selected from among oxygen, sulfur, nitrogen, silicon and phosphorus, but are not limited to these atoms. In embodiments in which two or more heteroatoms are present, the two or more heteroatoms can all be the same as one another, or some or all of the two or more heteroatoms can each be different from the others.

As used herein, the term "ring" refers to any covalently closed structure. Rings include, for example, carbocycles (e.g., aryls and cycloalkyls), heterocycles (e.g., heteroaryls and non-aromatic heterocycles), aromatics (e.g. aryls and heteroaryls), and non-aromatics (e.g., cycloalkyls and non-aromatic heterocycles). Rings can be optionally substituted. Rings can form part of a ring system.

As used herein, the term "ring system" refers to two or more rings, wherein two or more of the rings are fused. The term "fused" refers to structures in which two or more rings share one or more bonds.

The terms "heteroaryl" or, alternatively, "heteroaromatic" refers to an aryl group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. The polycyclic heteroaryl group may be fused or non-fused. Illustrative examples of heteroaryl groups include the following moieties:

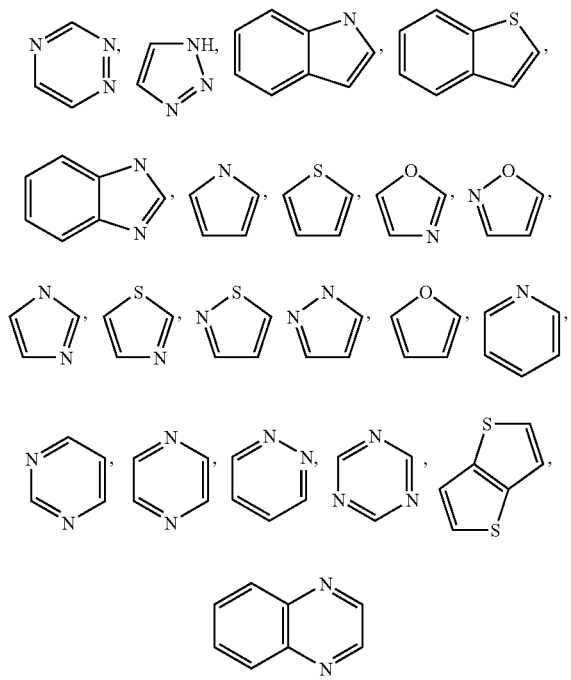

and the like. Depending on the structure, a heteroaryl group can be a monoradical or a diradical (i.e., a heteroarylene group).

The term "membered ring" can embrace any cyclic structure. The term "membered" is meant to denote the number of skeletal atoms that constitute the ring. Thus, for example, cyclohexyl, pyridine, pyran and thiopyran are 6-membered rings and cyclopentyl, pyrrole, furan, and thiophene are 5-membered rings.

An "isocyanato" group refers to a —NCO group.

The term "moiety" refers to a specific segment or functional group of a molecule. Chemical moieties are often recognized chemical entities embedded in or appended to a molecule.

As used herein, the term "O-carboxy" refers to a group of formula RC(=O)O—.

As used herein, the term "C-carboxy" refers to a group of formula —C(=O)OR.

As used herein, the term "acetyl" refers to a group of formula —C(=O)CH$_3$.

As used herein, a "xanthate" refers to RO—C(=S)—SR.

As used herein, a "thiocarbamate" refers to RO—C(=S)—NR$_2$.

As used herein, a "urea" refers to R$_2$N—C(=O)—NR$_2$.

As used herein, a "thiourea" refers to R$_2$N—C(=S)—NR$_2$.

As used herein, the term "trihalomethanesulfonyl" refers to a group of formula X$_3$CS(=O)$_2$— where X is a halogen.

As used herein, the term "cyano" refers to a group of formula —CN.

A "selenol" refers to R—SeH.

A "selenolate" refers to R—Se$^-$, which is the deprotonated form of a selenol.

A "diselane" refers to R—Se—Se—R.

A "thiol" refers to R—SH.

A "thiolate" refers to R—S$^-$, which is the deprotonated form of a thiol.

A "sulfate" refers to a —OS(=O)$_2$—OR

A "sulfinyl" group refers to a —S(=O)—R.

A "sulfonyl" group refers to a —S(=O)$_2$—R.

A "thioalkoxy" group refers to a —S-alkyl group.

As used herein, the term "S-sulfonamido" refers to a group of formula —S(=O)$_2$NR$_2$.

As used herein, the term "N-sulfonamido" refers to a group of formula RS(=O)$_2$NH—.

As used herein, the term "sulfate" refers to a group of the formula —OS(=O)$_2$OR.

As used herein, the term "phosphate" refers to a groups of the formula —OP(=O)$_2$OR.

As used herein, the term "phosphonate" refers to a groups of the formula —OP(=O)OR$_2$.

As used herein, the term "phosphinate" refers to a groups of the formula —OP(=O)R$_2$.

As used herein, the term "O-carbamyl" refers to a group of formula —OC(=O)NR$_2$.

As used herein, the term "N-carbamyl" refers to a group of formula ROC(=O)NH—.

As used herein, the term "C-amido" refers to a group of formula —C(=O)NR$_2$.

As used herein, the term "N-amido" refers to a group of formula RC(=O)NH—.

As used herein, the substituent "R" appearing by itself and without a number designation refers to a substituent selected from among from hydrogen, alkyl, cycloalkyl, aryl, heteroaryl (bonded through a ring carbon) and non-aromatic heterocycle (bonded through a ring carbon).

Throughout the specification, groups and variables thereof can be chosen by one skilled in the field to provide stable bilayer coatings on nanoparticle and stable compositions.

Nanoparticles

Compositions provided herein include a nanoparticle coated with a bilayer of molecules, wherein the bilayer of molecules is formed from:

(a) a layer of surface binding molecules in direct contact with the nanoparticle, wherein the surface binding molecules include:
  (i) a hydrophobic moiety; and
  (ii) a binding moiety that has an affinity for the nanoparticle surface; and
(b) a layer of amphiphatic molecules;

wherein the layer of surface binding molecules of (a) and the layer of amphiphatic molecules of (b) are held together by hydrophobic interactions. The layer of surface binding molecules of (a) forms a complete layer that coats the nanoparticle surface.

Compositions provided herein include a nanoparticle, which has a diameter of about 1 nm up to about 900 nm. In some embodiments, compositions provided herein include a nanoparticle with a diameter of about 1 nm up to about 10 nm, about 20 nm, about 30 nm, about 40 nm, about 50 nm about 60 nm, about 70 nm, about 80 nm, about 90 nm, about 100 nm, about 200 nm, about 300 nm, about 400 nm, about 500 nm about 600 nm, about 700 nm, about 800 nm, or up to about 900 nm. In some embodiments, compositions provided herein include a nanoparticle with a diameter of about 0.5 nm up to about 200 nm. In other embodiments, compositions provided herein include a nanoparticle with a diameter of about 1 nm up to about 100 nm. In some other embodiments, compositions provided herein include a nanoparticle that has a diameter of about 1 nm up to about 40 nm. In some embodiments, compositions provided herein include a nanoparticle with a diameter of about 1 nm about 2 nm, about 3 nm, about 4 nm, about 5 nm, about 10 nm about 15 nm, about 20 nm, about 25 nm, about 30 nm, about 35 nm, about 40 nm, about 45 nm, about 50 nm, about 55 nm, or about 60 nm.

In other embodiments, provided herein are compositions that include a microparticle coated with a bilayer of molecules, wherein the bilayer of molecules is formed from:

(a) a layer of surface binding molecules in direct contact with the microparticle, wherein the surface binding molecules include:
  (i) a hydrophobic moiety; and
  (ii) a binding moiety that has an affinity for the nanoparticle surface; and
(b) a layer of amphiphatic molecules;

wherein the layer of surface binding molecules of (a) and the layer of amphiphatic molecules of (b) are held together by hydrophobic interactions. The layer of surface binding molecules of (a) form a complete layer that coats the microparticle surface.

In some embodiments, compositions provided herein include a microparticle that has a diameter of about 1 micron up to about 1000 microns. In other embodiments, the microparticle has a diameter of about 1 micron, about 2 micron, about 3 microns, about 4 microns, about 5 microns, about 10 microns, about 15 microns, about 20 microns, about 40 microns, about 80 microns, about 100 microns, about 200 microns, about 300 microns, about 400 microns, about 500 microns, about 600 microns, about 700 microns, about 800 microns, about 900 microns, or about 1000 microns. In some embodiments, the microparticle has a diameter of about 1 micron up to about 500 microns. In other embodiments, the microparticle has a diameter of about 1 micron up to about 200 microns. In some other embodiments, the microparticle has a diameter of about 1 micron up to about 100 microns.

In some embodiments, the nanoparticle in the compositions provided herein does not have a charge and is neutral. In some other embodiments, the nanoparticle in the compositions provided herein has a charge. In other embodiments, the nanoparticle in the compositions provided herein has a positive charge. In some other embodiments, the nanoparticle in the compositions provided herein has a negative charge. It is understood that if a nanoparticle is charged it will be accompanied by an appropriate counter ion(s) to balance the charge of the nanoparticle.

Compositions provided herein include a nanoparticle selected from among inorganic metals, inorganic metal halides, inorganic metal oxides, inorganic metal sulfides, inorganic metal serenades, mixed metal clusters, inorganic metal nitrides, metal alloys, ceramics, semiconductors, magnetic nanoparticles, and heteropolyanion nanoparticles. In other embodiments, compositions provided herein include a nanoparticle selected from among inorganic metals, inorganic metal halides, inorganic metal oxides, metal alloys, ceramics, semiconductors, and magnetic nanoparticles. In some other embodiments, compositions provided herein include a nanoparticle selected from among inorganic metals, inorganic metal halides, and magnetic nanoparticles.

Compositions provided herein include a nanoparticle which includes at least one metal selected from among scandium, titanium, vanadium, chromium, manganese, iron, cobalt, nickel, copper, zinc, yttrium, zirconium, niobium, molybdenum, ruthenium, rhodium, palladium, silver, cadmium, hafnium, tantalum, tungsten, rhenium, osmium, iridium, platinum, gold, gadolinium, aluminum, gallium, indium, tin, thallium, lead, bismuth, magnesium, calcium, strontium, barium, lithium, sodium, potassium, boron, silicon, phosphorus, germanium, arsenic, antimony, and combinations thereof. In other embodiments, compositions provided herein include a nanoparticle that includes at least one metal selected from among scandium, titanium, vanadium, chromium, manganese, iron, cobalt, nickel, copper, zinc, yttrium, zirconium, niobium, molybdenum, ruthenium, rhodium, palladium, silver, cadmium, hafnium, tantalum, tungsten, rhenium, osmium, iridium, platinum, gold, aluminum, gallium, indium, tin, thallium, lead, bismuth, and combinations thereof In some other embodiments, compositions provided herein include a nanoparticle that includes at least one metal selected from among titanium, vanadium, chromium, manganese, iron, cobalt, nickel, copper, zinc, zirconium, molybdenum, ruthenium, rhodium, palladium, silver, cadmium, tungsten, rhenium, osmium, iridium, platinum, gold, aluminum, bismuth and combinations thereof. In some embodiments, compositions provided herein include a nanoparticle that includes a metal selected from among iron and gold. In other embodiments, compositions provided herein include a nanoparticle that includes gold. In some other embodiments, compositions provided herein include a nanoparticle that includes iron.

In some embodiments, compositions provided herein include a nanoparticle that includes a heavy metal. Heavy metals are metals that have an atomic number (Z) greater than about 20. Examples of heavy metals include, but are not limited to, scandium (Z=21), titanium (Z=22), vanadium (Z=23), chromium (Z=24), manganese (Z=25), iron (Z=26), cobalt (Z=27), nickel (Z=28), copper (Z=29), zinc (Z=30), yttrium (Z=39), zirconium (Z=40), niobium (Z=41), molybdenum (Z=42), ruthenium (Z=44), rhodium (Z=45), palladium (Z=46), silver (Z=47), cadmium (Z=48), hafnium (Z=72), tantalum (Z=73), tungsten (Z=74), rhenium (Z=75), osmium (Z=76), iridium (Z=77), platinum (Z=78), gold (Z=79), gadolinium (Z=64), gallium (Z=31), indium (Z=49), tin (Z=50), thallium (Z=81), lead (Z=82), bismuth (Z=83), and uranium (Z=92).

In some embodiments, compositions provided herein include a nanoparticle that is charged. In embodiments where the nanoparticle has a positive charge or negative charge, the nanoparticle will have an affinity for surface binding molecules that include a binding moiety that has the opposite charge to that on the nanoparticle.

In some embodiments, the nanoparticle includes a magnetic element, such as, for example, a magnetic element selected from among iron, cobalt, nickel, cobalt, chromium, manganese, gadolinium, platinum, and combinations thereof. In other embodiments, the nanoparticle includes any element that is capable of becoming magnetic. The nanoparticle can include any magnetic element, or element that is capable of becoming magnetic, including metal oxides and halides salts thereof, as well as combinations with other suitable elements. In one embodiment, compositions provided herein include iron oxide nanoparticles, such as, for example, magnetite ($Fe_3O_4$).

In some embodiments, the nanoparticle is a gold nanoparticle or a silver-gold mixed metal nanoparticle or a copper-gold mixed metal nanoparticle or an iron oxide nanoparticle or a platinum nanoparticle.

In one embodiment, compositions provided herein include a nanoparticle that can absorb radiation, such as, but not limited to, X-rays, infrared radiation, microwaves, ultrasound radiation, radiofrequencies, visible radiation, and/or ultraviolet radiation. In some embodiments, compositions provided herein include a nanoparticle that can absorb radiation, such as, but not limited to, X-ray radiation and/or radiofrequencies. In some embodiments, compositions provided herein include a nanoparticle that can absorb X-ray radiation.

In some embodiments, compositions provided herein include a nanoparticle that includes radioisotopes. In some other embodiments, compositions provided herein include a nanoparticle that includes radioisotopes that can emit radiation, such as, for example, beta radiation. Radioisotopes can emit radiation, such as for example, beta radiation and are useful, for example, in treating tumors with radiation; further, gamma emitters are useful for imaging, and alpha emitters are useful for therapies.

In some embodiments, compositions provided herein include nanoparticles with a narrow particle size distribution. In some other embodiments, provided herein are methods for coating nanoparticles in solution with a bilayer of molecules formed from surface binding molecules and amphiphatic molecules, wherein the nanoparticles have a narrow particle size distribution.

Surface Binding Molecule

Provided herein are compositions that include a nanoparticle that is coated with a bilayer of molecules, methods of coating nanoparticles with a bilayer of molecules, methods of making nanoparticles coated with a bilayer of molecules, and methods of use thereof. The bilayer that coats the nanoparticle self assembles from the interaction of surface binding molecules (bound to a nanoparticle) and amphiphatic molecules. The compositions provided herein include a nanoparticle coated with a bilayer of molecules, wherein the bilayer of molecules is formed from:

(a) a layer of surface binding molecules in direct contact with the nanoparticle, wherein the surface binding molecules include:

(i) a hydrophobic moiety; and
(ii) a binding moiety that has an affinity for the nanoparticle: and (b) a layer of amphiphatic molecules;

wherein the layer of surface binding molecules of (a) and the layer of amphiphatic molecules of (b) are held together by hydrophobic interactions. The layer of surface binding molecules of (a) forms a complete layer on the nanoparticle. In some embodiments, the surface binding molecules have the same or are derived from the same chemical structure.

Nanoparticles have a variety of surface atoms and chemical properties. The surface binding molecules will bind to the nanoparticle by a means appropriate to the specific surface to be coated.

The binding moiety of the surface binding molecules of (a) includes a neutral moiety or a charged moiety. The binding moiety that has an affinity for the surface to be coated, such as, for example, the nanoparticle, can be one that covalently reacts with the surface, that non-covalently interacts, that interacts through ionic interactions or that coordinates and attaches with an intermediate bond strength.

In some embodiments, the surface of the nanoparticle is charged and the surface binding molecule(s) may be attached to the surface of the nanoparticle by charge interaction or coordination. In such cases, the surface binding molecule would include a binding moiety that has a charge that is opposite to that found on the surface of the nanoparticle. For binding to a negatively charged surface, the surface binding molecule would contain one or more ionizable groups that can bear a positive charge, such as, for example, amino groups. For binding to a positively charged surface, the surface binding molecule would include one or more negatively charged groups, such as, for example, carboxyl or sulfonate groups.

The binding moiety of the surface binding molecules of (a) can be any moiety that interacts with the surface of the nanoparticle, which results in an ionic interaction, covalent bond or coordination with the nanoparticle. In some embodiments, the binding moiety of the surface binding molecules is selected from among a thiol moiety, a thiolate moiety, a disulfide moiety, a sulfide moiety, a sulfate moiety, a selenol moiety, a seleneloate moiety, a diselane moiety, an alcohol moiety, an alkoxide moiety, a carboxyl moiety, a carboxylate moiety, an ester moiety, an anhydride moiety, an amine moiety, an amine oxide moiety, a nitrile moiety, a diazonium moiety, a phosphine moiety, a phosphine oxide moiety, a phosphonate moiety, a phosphinite moiety, a silane moiety, a sulfonate moiety, a sulfate moiety, an isonitrile moiety, an alkene moiety, an alkyne moiety, a carbamate moiety, a xanthate moiety, a thiocarbamate moiety, a urea moiety, a thiourea moiety, and combinations thereof. (see, for example, Love, J. C., Estroff, L. A., Kriebel, J. K, Nuzzo, R. G., Whitesides, G. M. "Self-Assembled Monolayers of Thiolates on Metals as a Form of Nanotechnology" Chem. Rev. 2005, 105, 1103-1169, herein incorporated by reference)

In some embodiments, the binding moiety of the surface binding molecules is selected from among a thiol moiety, a thiolate moiety, an alcohol moiety, an alkoxide moiety, a carboxyl moiety, a carboxylate moiety, an amine moiety, an amine oxide moiety, a phosphine moiety, a phosphine oxide moiety, a phosphonate moiety, a phosphinite moiety, a silane moiety, a sulfonate moiety, a sulfate moiety, and combinations thereof.

The hydrophobic moiety of the surface binding molecules of (a) is selected from among alkyl moieties, alkene moieties, alkyne moieties, aryl moieties, hydrophobic moieties of fatty acids, steroid moieties, and combinations thereof.

The surface binding molecules form a complete layer on the nanoparticle and the hydrophobic moieties of the surface binding molecules of (a) provide a physical barrier, preventing access to the nanoparticle. The surface binding molecules form a complete layer on the nanoparticle and the hydrophobic moieties of the surface binding molecules of (a) provide a physical barrier, preventing access of water, ions, metals, and/or other hydrophilic species to the nanoparticle.

In some embodiments, the binding moiety of the surface binding molecules includes sulfur, phosphorus, nitrogen, oxygen, and/or silicon atoms that have an affinity for metal surfaces, such as, but not limited to, gold, silver, platinum, palladium, copper, nickel, iron, as well as the corresponding metal oxides. Suitable surface binding molecules include, but are not limited to, compounds with the formula R—SH, R—S—R', R—S—S—R', (RR'R"—P), (R—NH$_2$), (RR'—NH), RCOOH, where the R, R', and R" groups are organic moieties that are hydrophobic moieties. Hydrophobic moieties, include, but are not limited to, alkyl groups CH$_3$—(CH$_2$)$_n$—, where n is 2 to 30, aryl moieties, such as, for example, phenyl moieties, naphthyl moieties, anthracenyl moieties, and the like, or hydrocarbon ring structures. The hydrophobic moieties may be linear or branched, saturated or unsaturated.

In some embodiments, the surface binding molecules will be chosen so that surface binding molecules will be able to pack closely together on the surface of the nanoparticle and maximize the hydrophobic interactions of the hydrophobic moieties with neighboring molecules, such as, for example, maximizing the van der Waals forces or hydrogen bonds. Surface binding molecules that are able to pack closely and minimize the nearest-neighbor distances between adjacent surface binding molecules will lead to coating layers that are durable and provide increased protection of the underlying nanoparticle surface to environmental elements, such as, for example, moisture, ions, and oxygen.

In some embodiments, a combination of surface binding molecules may be used in order vary the protrusion distance or roughness of the coating and/or to create weak and strong surface regions for further exchange or modification.

Surfaces, particles and/or nanoparticles that contain oxides, such as those containing oxides of iron, cobalt, chromium, nickel, copper, molybdenum, and other metals, can be reacted with surface binding molecules that include a binding moiety that includes silicon. For example, the surface binding molecules can be selected from among alkylchlorosilanes and alkylalkoxysilanes. Surface binding molecules that include a silicon binding moiety will react with hydroxylated metal surfaces and metal oxide surfaces. The driving force for the self-assembly of a monolayer of the silicon containing surface binding molecules is the formation of Si—O bonds. Examples of silicon containing surface binding molecules include, but are not limited to, phenyldimethylsilyl chloride, dimethyl-n-octadecylchlorosilane, n-octadecyltrimethoxysilane, octadecyltrichlorosilane, hexadecyldichlorosilane, and other silanes (see, e.g., Ulman, A. *Chem Rev.* 1996, 96, 1533-1554, herein incorporated by reference).

In some embodiments, the surface binding molecules of (a) are selected from among alkyl thiols, alkyl amines, alcohols, and carboxylic acids. In other embodiments, the surface binding molecules of (a) are selected from among dodecanethiol, octanethiol, octadecylthiol, thiophenol, aminothiophenol, triphenylphosphine, tributylphosphine, tri(dodecyl)phosphine, dodecylamine, phenyldimethylsilyl chloride, dimethyl-n-octadecylchlorosilane, hexadecyldichlorosilane, and cetyl alcohol. In some other embodiments, the surface binding molecules of (a) are selected from among dodecanethiol, octanethiol, octadecylthiol, dodecylamine, and cetyl alcohol.

In some embodiments, the surface binding molecules of (a) are identical or derived from moieties have the same chemical structure.

In some embodiments, the surface binding molecules of (a) are selected from among:

Alkyl thiols: Methane thiol, ethane thiol, propane thiol, butane thiol, pentane thiol, hexane thiol, heptane thiol, octane thiol, nonane thiol, decane thiol, undecane thiol, dodecane thiol, tridecane thiol, tetradecane thiol, pentadecane thiol, hexadecane thiol, heptadecane thiol, octadecane thiol, nonadecane thiol, eicosane thiol, heneicosane thiol, docosane thiol, tricosane thiol, tetracosane thiol, pentacosane thiol, hexaconsane thiol, heptacosane thiol, octacosane thiol, nonacosane thiol, triacontane thiol, hentriacontane thiol.

Alkyl Disulfides: such moieties can bind to the surface of a nanoparticle by more than one site per moiety (in the case of cyclic disulfides) or can provide more than one moiety that binds to the nanoparticle (in the case of linear disulfides); appropriate disulfides include dimers of the aforementioned alkyl thiols or cyclic analogs of the aforementioned alkyl thiols.

Saturated alkyl acids: methanoic acid (formic acid), ethanoic acid (acetic acid), propanoic acid (propionic acid), butanoic acid (butyric acid), pentanoic acid (valeric acid), hexanoic acid (caproic acid), heptanoic acid (enanthic acid), octanoic acid (caprylic acid), nonanoic acid (pelargonic acid), decanoic acid (capric acid), undecanoic acid (undecylic acid), dodecanoic acid (lauric acid), tridecanoic acid (tridecylic acid), tetradecanoic acid (myristic acid), pentadecanoic acid (pentadecylic acid), hexadecanoic acid (palmitic acid), heptadecanoic acid (margaric acid), octadecanoic acid (stearic acid), nonadecanoic acid (nonadecylic acid), eicosanoic acid (arachidic acid), heneicosanoic acid, docosanoic acid (behenic acid), tricosanoic acid, tetracosanoic acid (lignoceric acid), pentacosanoic acid, hexaconsanoic acid (cerotic acid), heptacosanoic acid, octacosanoic acid (montanic acid), nonacosanoic acid, triacontanoic acid (melissic acid), hentriacontanoic acid.

Unsaturated fatty acids: 10-undecenoic acid (10-undecylenic acid), cis-9-tetradecenoic acid (myristoleic acid), trans-9-tetradecenoic acid (myristelaidic acid), 9-tetradecynoic acid, cis-10-pentadecenoic acid cis-9-hexadecenoic acid (palmitoleic acid), trans-9-hexadecenoic acid (palmitelaidic acid), cis-10-heptadecenoic acid, cis-6-octadecenoic acid (petroselinic acid), trans-6-octadecenoic acid, cis-7-octadecenoic acid, trans-7-octadecenoic acid, cis-9-octadecenoic acid (oleic acid), trans-9-octadecenoic acid (elaidic acid), 9-octadecynoic acid (stearolic acid), cis-11-octadecenoic acid (cis-vaccenic acid), trans-11-octadecenoic acid (trans-vaccenic acid), cis-12-octadecenoic acid, trans-12-octadecenoic acid, cis-13-octadecenoic acid, trans-13-octadecenoic acid, cis-15-octadecenoic acid, 17-octadecynoic acid, cis-12-hydroxy-9-octadecenoic acid (ricinoleic acid), trans-12-hydroxy-9-octadecenoic acid (ricinelaidic acid), cis-9,12-octadecadienoic acid (linoleic acid), trans-9,12-octadecadienoic acid (linolenelaidic acid), 9,11(10,12)-octadecadienoic acid, cis-6,9,12-octadecatrienoic acid (γ-linolenic acid), cis-9,12,15-octadecatrienoic acid (linolenic acid), trans-9,12,15-octadecatrienoic acid (linolenelaidic acid), cis-6,9,12,15-octadecatetraenoic acid, cis-10-nonadecenoic acid, cis-5-eicosenoic acid, cis-8-eicosenoic acid, cis-11-eicosenoic acid (gondoic acid), trans-11-eicosenoic acid, cis-13-eicosenoic acid, 13-eicosynoic acid, cis-11,14-eicosadienoic acid, cis-5,8,11-eicosatrienoic acid, 5,8,11-eicosatriynoic acid, cis-8,11,14-eicosatrienoic acid, 8,11,14-eicosatriynoic acid, cis-11,14,17-eicosatrienoic acid, cis-5,8,11,14-eicosatetraenoic acid (arachidonic acid), cis-5,8,11,14,17-eicosapentaenoic acid, cis-13-docosenoic acid (erucic acid), trans-13-docosenoic acid (brassidic acid), cis-13,16-docosadienoic acid, cis-13,16,19-docosatrienoic acid, cis-7,10,13,16-docosatetraenoic acid, cis-7,10,13,16,19-docosapentaenoic acid, cis-4, 7,10,13,16,19-docosahexaenoic acid, cis-15-tetracosenoic acid (nervonic acid).

Saturated Alcohols: methanol, ethanol, propanol, butanol, pentanol, hexanol, heptanol, octanol, nonanol, decanol, undecanol, dodecanol, tridecanol, tetradecanol, pentadecanol, hexadecanol, heptadecanol, octadecanol, nonadecanol, eicosanol, heneicosanol, docosanol, tricosanol, tetracosanol, pentacosanol, hexaconsanol, heptacosanol, octacosanol, nonacosanol, triacontanol, hentriacontanol.

Alkyl Amines: ethylamine, propylamine, butylamine, pentylamine, hexylamine, heptylamine, octanylamine, nonanylamine, decanylamine, undecanylamine, dodecanylamine, tridecanylamine, tetradecanylamine, pentadecanylamine, hexadecanylamine, heptadecanylamine, octadecanylamine, nonadecanylamine, eicosanylamine, heneicosanylamine, docosanylamine, tricosanylamine, tetracosanylamine, pentacosanylamine, hexaconsanylamine, heptacosanylamine, octacosanylamine, nonacosanylamine, triacontanylamine, hentriacontanylamine.

Resorcinolic lipids (Kozubek, A.; Tyman, J. H. Chem. Rev. 1999, vol. 99, No. 1, 1-25): -olivetol, persoonol, grevillol, ardisinol I, ardisinol II, adipostatin A, adipostatin B, bilobol, hydrobilobol, cardol, irisresorcinol, panosialin, stemphol, α-leprosol, β-leprosol, merulinic acid, xenognosin; or see Table 2, pages 5-8 of Kozubek, A.; Tyman, J. H. Chem. Rev. 1999, vol. 99, No. 1.

Coatings provided herein include surface binding molecules, which include:

(i) a hydrophobic moiety; and (ii) a binding moiety that has an affinity for the surface to be coated.

In some embodiments, the surface binding molecules can attach to the surface by covalent attachment or coordination. In other embodiments, the nanoparticle may already contain a reactive group that can undergo a reaction with the binding moiety of the surface binding molecules. For example, in some cases nanoparticles may already be coated with a monolayer of bifunctional molecules (i.e. molecules that have reactive functional group(s) at both ends of the molecule, one for binding to the surface to be coated and the other that faces the environment) (see, for example, Love, J. C.; Estroff, L. A.; Kreibel, J. K.; Nuzzo, R. G. Whitesides, G. M., *Chem Rev.*, 2005, 105, 1103-1169, section 5.2, incorporated herein by reference). The monolayer coating formed from the bifunctional molecules includes terminal exposed reactive functional groups that can be reacted with the surface binding molecules provided herein. In these embodiments, a monolayer of surface binding molecules will then coat the monolayer of the bifunctional molecules.

For example, terminal exposed functional groups on monolayers formed from bifunctional molecules that coat nanoparticles and surfaces include: maleimide functional groups (that can react with surface binding molecules that have a thiol or thiolate are a binding moiety); disulfide functional groups (that can reactive with surface binding molecules that have a thiol or thiolate binding moiety); amine functional groups (that can react with surface binding molecules that have a isocyanate, isothiocyante or carboxylic acid or carboxylic acid derivative binding moiety); alkene functional groups (that can react with surface binding molecules that have an alkene binding moiety in the presence of a metathesis catalyst); azide functional groups (that can react with surface binding molecules that have an alkyne binding moiety); alkyne functional groups (that can react with surface binding molecules that have an azide binding moiety); substituted phosphane functional groups (that can react with surface binding molecules that have an azide binding moiety to form an amide bond); phosphonate functional groups (that can react with surface binding molecules that have an alcohol binding moiety); aldehyde moieties (that can react with surface binding molecules that have an amine binding moiety); anhydride moieties (that can react with surface binding molecules with an amine binding moiety); alkene moieties (that can react with surface binding molecules that have a 1,4-diene binding moiety). In some embodiments, chemical modification/derivitization of the terminal, exposed reactive functional group of the monolayer formed from the bifunctional molecules can be carried out prior to exposure to surface binding molecules. By way of example only, nanoparticles and/or surfaces that are coated with a monolayer of bifunctional molecules that have terminal, exposed carboxylic acid reactive groups, the carboxylic acid groups can be chemically modified to acid anhydrides, acid halides, or activated with N-hydroxysuccinimide or pentafluorophenol, prior to reaction/exposure to the surface binding molecules.

In some embodiments, the nanoparticle will be coated with three layers that include: 1) a layer of bifunctional molecules that include the terminal, exposed reactive functional groups; 2) a layer of surface binding molecules that form a covalent bond with the terminal, exposed reactive functional groups of 1); and 3) a layer of amphiphatic molecules in contact with the surface binding molecules; wherein the layer of surface binding molecules and amphiphatic molecules are held together by hydrophobic interactions.

The bonding, interaction or coordination of the surface binding molecules to the nanoparticle may be strengthened by multiple binding groups (i.e. multiple reactive moieties) on the same surface binding molecule. Branches in the hydrophobic moiety of the surface binding molecule permit multiple reactive moieties to exist on the same surface binding molecule. For example, lipoic acid or dihydrolipoic acid contain one carboxylic acid moiety and two sulfur atoms, which are capable of bonding, interacting or coordinating to the surface of nanoparticles. Chelating molecules, which include multiple reactive moieties, and also include a hydrophobic moiety, are also contemplated as surface binding molecules for use in the compositions provided herein. Some small oligomers or polymers also contain multiple reactive moieties and may be included in the compositions provided herein as surface binding molecules. For example, some small oligomers and or polymers, such as, for example, polylysine (which has multiple amine groups), polyglutamic acid (which has multiple carboxyl groups), polycysteine (which has multiple thiol groups), could be derivatized to include a hydrophobic moiety/moieties and thus be used as surface binding molecules in the composition provided herein. Carboxyl and amine groups are not only useful for charge interaction or coordination, but may also be covalently coupled to the surface. Other compounds, oligomers, or polymers known to those skilled in the art are also capable of providing multiple attachment sites to the surface to be coated.

In some embodiments, surface binding molecules provided herein include multiple reactive moieties. In some embodiments, surface binding molecules provided herein include multiple reactive moieties that are spaced apart. In other embodiments, surface binding molecules provided herein include multiple reactive moieties that are spaced apart and are charged.

In some embodiments, nanoparticles provided herein are charged. In other embodiments, nanoparticles provided herein include, for example, heteropolyanion nanoparticles, such as, for example, the heteropolytungstates and vanadates. In some embodiments, nanoparticles provided herein include heteropolyanions, such as, for example, $SiW_{12}O_{42}^{4-}$ and $P_2W_{18}O_{42}^{7-}$ which have diameters of about 1 nm to about 1.3 nm. For example, 12-silicotungstic acid in the Keggin structure ($SiW_{12}O_{42}^{4-}$) can be complexed or bound to ammonium salts. Surface binding molecules that include single cationic reactive moieties for binding to the nanoparticle do provide charge neutralization, however, multiple surface binding molecules are required to coat the surface and fully bind to the charged regions. In some embodiments, single binding molecules or singly charged molecules are not as stable as multipoint binding from a single molecule. In some embodiments, it may be advantageous to use a coating molecule with multiple cationic groups to bind to heteropolyanion nanoparticles. In embodiments where the size of heteropolyionic particles is known, an optimal neutralizing molecule can then be designed that will include one or a multitude of ionic moieties that will bind to the particle and neutralize the charge of the polyionic particle.

In some embodiments, the surface binding molecule(s) will include reactive moieties that bear a positive charge or are capable of bearing a positive charge, such as, for example, primary, secondary, tertiary, or quaternary amines. In some embodiments, quaternary amine moieties are stable in basic environments. Examples of surface binding molecules that include one or more cationic amine moieties include, but are not limited to, choline chloride, phosphatidyl choline, tetrabutylammoium bromide, 1,12 diaminododecane, derivatives of tetraminoethane, such as, for example, 1,1,4,7,10,10-hexamethyltriethylenetetramine and N,N'-bis(3-aminopropyl)-1,4-diaminobutane, and other compounds containing one or more amines.

In some embodiments, surface binding molecules can be prepared that include multiple amine moieties that are spaced apart with hydrophobic organic moieties. The surface binding molecules may be prepared such that the hydrophobic organic moieties space apart that amine moieties, which may be protonated and bear a positive charge, allowing the neutralization of the distributed charge on the nanoparticle. The hydrophobic organic moieties could interact with the amphiphatic molecules to form the bilayer coating on the nanoparticle. By way of example only, 1 nm $SiW_{12}O_{42}^{4-}$ nanoparticles could be coated with surface binding molecules that have multiple amine groups spaced apart with hydrophobic organic moieties that have about 10-18 atom-to-atoms bonds in the chain. This would then be a single molecule that could neutralize the distributed charge and would have increased stability than surface binding molecules that include a single amine moiety or a single cationic amine moiety. In one embodiment, $SiW_{12}O_{42}^{4-}$ nanoparticles could be coated with a bilayer that is formed from surface binding molecules selected from among diamino compounds, and amphiphatic molecules selected from among surfactant molecules. In one embodiment, $SiW_{12}O_{42}^{4-}$ nanoparticles could be coated with a bilayer formed from 1,12 diaminododecane and Tween 20, wherein the hydrophobic region of the 1,12 diaminododecane molecules interact non-covalently with the hydrophobic region of the Tween 20 molecules, to yield a neutralized and stabilized tungsten cluster with ethylene glycol units presented to the aqueous environment.

In some embodiments, more than one type of surface binding molecule is used in the compositions provided herein. In other embodiments, the surface binding molecules in the compositions provided herein are different. In other embodiments, the surface binding molecules in the composition provided herein have the same or are derived from the same chemical structure. In one embodiment, compositions provided herein include a single type of surface binding molecule.

In some embodiments, compositions provided herein include nanoparticles coated with a bilayer of molecules, wherein the bilayer is formed from surface binding molecules and amphiphatic molecules that do not readily absorb radiation that is applied to the composition.

In some embodiments, compositions provided herein include surface binding molecules that are selected from among the amphiphatic molecules provided herein.

Amphiphatic Molecules

Compositions provided herein include nanoparticles that are coated with a bilayer of molecules formed from surface binding molecules and amphiphatic molecules. The outer layer of the bilayer coatings provided herein are made from amphiphatic molecules. The amphiphatic molecules include a hydrophobic moiety, which will interact with the hydrophobic moieties of the surface binding molecules, and a hydrophilic moiety, which faces the environment and determines the surface properties of the bilayer coating. The hydrophilic moiety of the amphiphatic molecules presents chemical functional groups to the environment. The hydrophilic groups of the amphiphatic molecules are terminal functional groups that are also referred to as environmental groups.

In some embodiments, the layer of amphiphatic molecules of (b) increase the water solubility of the nanoparticle coated with the layer of surface binding molecules of (a). In some embodiments, the amphiphatic molecules of (b) include a hydrophilic moiety selected from among phosphate groups, sulfonate groups, sulfate groups, hydroxyl groups, carboxyl groups, amino groups, amide groups, carbohydrate groups, peptide groups, protein groups, nucleic acid groups, ethylene glycol groups, and combinations thereof. The hydrophilic moieties of the amphiphatic molecules determine the surface properties of the bilayer-coated nanoparticles. In some embodiments, the hydrophilic moieties of the amphiphatic molecules increase the water solubility of the bilayer-coated nanoparticles. In other embodiments, the hydrophilic moieties of the amphiphatic molecules increase the biocompatibility of the bilayer-coated nanoparticles. In other embodiments, the hydrophilic moieties of the amphiphatic molecules increase the water solubility and the biocompatibility of the bilayer-coated nanoparticles. In some embodiments, the hydrophilic moieties of the amphiphatic molecules decrease the toxicity of the bilayer-coated nanoparticles.

The amphiphatic molecules in the bilayer coatings interact with the surface binding molecules non-covalently. The amphiphatic molecules form a coating on the monolayer of the surface binding molecules that coats the nanoparticle. The amphiphatic molecules and the surface binding molecules interact non-covalently through their hydrophobic moieties. Such non-covalent interactions results in hydrophobic effects and/or hydrophobic interactions, such as, for example, van der Waals forces, π-π stacking interactions, and/or London Dispersion forces.

In some embodiments, the hydrophobic moieties of the amphiphatic molecules of (b) include a hydrophobic moiety selected from among alkyl moieties, alkene moieties, alkyne moieties, aryl moieties, carbocyclic moieties, hydrophobic moieties of fatty acids, steroid moieties, and combinations thereof. The hydrophobic moieties may be linear or branched. Hydrophobic alkyl moieties include, but are not limited to, $CH_3-(CH_2)_n-$, where n is 2 to 30, and branched and unsaturated forms thereof.

The hydrophobic moieties of the amphiphatic molecules will interact with the hydrophobic moieties of the surface binding molecules to form a composite structure/intermediate. In some embodiments this composite structure/intermediate self assembles into a bilayer coating on nanoparticles.

The amphiphatic molecules have a hydrophobic moiety and a hydrophilic moiety, also referred herein to an environmental moiety, which is designed or chosen to provide desired functionalities/chemical groups to be presented to the environment once the nanoparticle is coated with the bilayer of molecules as discussed herein.

In some embodiments, the hydrophilic moieties of the amphiphatic molecules is/are chosen to confer some desired property to the bilayer coated nanoparticle. In some cases, the hydrophilic moieties will confer water solubility and/or biocompatibility. In other embodiments, the surface of the bilayer coated nanoparticles provided herein will include hydrophilic moieties from the amphiphatic molecules that are reactive functional groups to which other molecules can be coupled in order to provide bilayer-coated nanoparticle conjugates.

In some embodiments, the hydrophilic moieties of the amphiphatic molecules are selected from among polyethylene glycols and sugars, which confer water solubility and biocompatibility. Examples of amphiphatic molecules that have polyethylene glycol and sugar moieties, include, but are not limited to, n-dodecyl β-D-maltoside, dodecyl tetraethylene glycol ether, triethylene glycol monododecyl ether, and Tween 20. In other embodiments, the ampiphatic molecules of (b) include a hydrophilic moiety selected from among phosphate groups, sulfonate groups, sulfate groups, hydroxyl groups, carboxyl groups, amino groups, amide groups, carbohydrate groups, peptide groups, protein groups, nucleic acid groups, ethylene glycol groups, and combinations thereof.

In some embodiments, the amphiphatic molecules are selected from among detergents, soaps, emulsifiers, and surfactants. Examples of detergents, soaps, emulsifiers, and surfactants include, but are not limited to, Tween 20, Brij, triton, polysorbates, sorbitan fatty acid esters, fatty acids and phospholipids.

Any molecule that has a hydrophobic moiety and a hydrophilic moiety is contemplated for use as an amphiphatic molecule in the compositions provided herein. In some embodiments, compositions provided herein include amphiphatic molecules that are selected from among the surface binding molecules provided herein.

In some embodiments, the amphiphatic molecules in the compositions provided herein include a hydrophilic moiety that has reactive functional groups that may be used to bind to additional molecules. In some embodiments, the amphiphatic molecules in the compositions provided herein include a hydrophilic moiety that has reactive functional groups that may be used to form a covalent bond with molecules in solution. For example, amphiphatic molecules that include a terminal aldehyde functional group that faces the environment can react with amino groups from other molecules to form Schiff bases. For example, bilayer coated nanoparticles that include amphiphatic molecules such as, for example, dodecanal, can be coupled to antibodies that include a reactive amine functional group to form a Schiff base. In some cases, the Schiff base formed from the bilayer coated nanoparticle that includes dodecanal is reduced with, for example, a hydride source, to provide an amine product. Other reactive groups that could be used to couple molecules to the bilayer coated nanoparticles include: amine functional groups (such as, for example, dodecylamine), carboxylic functional groups (such as, for example, fatty acids, such as for example, dodecanoic acid), chloroformate functional groups (such as, for example, dodecyl chloroformate), isocyanate functional groups (such as, for example, dodecylisocyante), alkyl halide functional groups (such as, for example, 1-bromododecane). Those skilled in the art can choose or design amphipahtic molecules that can be included in the bilayer coat nanoparticles and be used to couple antibodies, drugs, peptides, proteins, nucleic acids, carbohydrates, cells, and/or other surfaces to the bilayer coated nanoparticles.

In some embodiments, the terminal functional groups of the amphiphatic molecules, which form the outer layer of the bilayer, face the environment and can react directly with molecules present in solution (see, for example, Love, J. C.; Estroff, L. A.; Kreibel, J. K.; Nuzzo, R. G. Whitesides, G. M., *Chem Rev.,* 2005, 105, 1103-1169, section 5.2, incorporated herein by reference). For example, amphiphatic molecules that include the following terminally exposed reactive groups can be used to couple other molecules to the bilayer-coated nanoparticles or to functionalize the bilayer coating:

maleimide functional groups on the amphiphatic molecules can react with molecules that have a thiol or thiolate binding moiety disulfide functional groups on the amphiphatic molecules can react with molecules that have a thiol or thiolate binding moiety amine functional groups on the amphiphatic molecules can react with molecules that have a carboxylic, halide, isocyanate or isothiocyante binding moiety;

alkene functional groups on the amphiphatic molecules can (a) react with molecules that have an alkene binding moiety in the presence of a metathesis catalyst or with molecules that have a 1,4-diene moiety, (b) be alkylated, (c) add organic free radicals, or (d) add organic groups by free radical or ionic polymerization;

azide functional groups on the amphipahtic molecules can react with molecules that have an alkyne binding moiety, or undergo photochemical reactions;

alkyne functional groups on the amphiphatic molecules can react with molecules that have an azide binding moiety;

substituted phosphane functional groups on the amphiphatic molecules can react with molecules that have an azide binding moiety to form an amide bond;

phosphonate functional groups on the amphiphatic molecules can react with molecules that have an alcohol binding moiety;

aldehyde moieties on the amphiphatic molecules can react with molecules that have an amine binding moiety; and anhydride moieties on the amphiphatic molecules can react with molecules with an amine binding moiety.

In some embodiments, the environmental or hydrophilic moieties of the amphiphatic molecules are activated to react with other molecules in solution. In some embodiments, chemical modification/derivitization of the terminal, exposed reactive functional group of the amphiphatic molecules in the outer layer of the bilayer coating the nanoparticle is carried out prior to exposure to molecules that are to be coupled to the bilayer coated nanoparticle. For example, terminally exposed carboxylic acid reactive groups in the bilayer coating provided herein can be chemically modified to acid anhydrides, acid halides, or activated with N-hydroxysuccinimide or pentafluorophenol, prior to reaction/exposure to other molecules, such as, for example, antibodies, drugs, peptides, proteins, nucleic acids, carbohydrates, cells, and/or other surfaces.

In some embodiments, compositions provided herein include amphiphatic molecules that include charged moieties and/or moieties that can be charged. The charged moieties and/or moieties that can be charged will create a charged surface presented to the environment. Amphiphatic molecules that have a moiety that can be charged and/or are charged include, but are not limited to, 1-aminodecane, dodecylamine, 1-carboxydecane, sodium dodecylsulfate, cetyltrimethylammonium chloride. Amine, carboxyl, sulfate, phosphate, sulfonamide, and quaternary ammonium groups are useful groups for incorporating charges. Many other molecules with varying chain lengths, various branching patterns, various hydrophilic regions that have a hydrophilic region to ultimately be presented to the hydrophilic environment may be selected for use as the amphiphatic molecules in the compositions provided herein.

The covalent attachment of molecules to the bilayer coating of the nanoparticles is one strategy contemplated herein for the derivitization of the surface properties of the bilayer coating. In another embodiment, the properties of the surface of the bilayer coating are used to promote the adsorption of molecules from solution. In some embodiments, the amphipahtic molecules confer properties to the surface of the bilayer coating, such as, for example, hydrophilicity, hydrophobicity, electrostatics, and/or the predisposition of functional groups on the surface of the bilayer that are used to promote non-covalent interactions with adsorbed molecules on the surface. Non-covalent interactions stabilize adsorbed molecules on the surface of the bilayer coating of the nanoparticle. In some embodiments, non-covalent interactions that stabilize adsorbed molecules onto the surface of the bilayer coating are selected from among hydrogen bonds, van der Waals forces and electrostatics.

In some embodiments, the amphiphatic molecules include a chelate moiety as the environmental group. The incorporation of chelating functional groups into the amphiphatic molecules will enable the binding of ions, metals, and/or radio-isotopes to the bilayer coated nanoparticles. For example, amphiphatic molecules that have a hydrophobic domain and a nitrilotriacetic acid (NTA) group can be used to bind nickel, copper, or other ions that then permit attachment of 6-histidine or histidine tagged proteins. For example, the nickel salt of 1,2-dioleoyl-sn-glycero-3-[(N-(5-amino-1-carboxypentyl)iminodiacetic acid)succinyl] may be used in the layer of amphiphatic molecules in the compositions provided herein. Other chelating groups contemplated herein, include, but are not limited to, diethylenetriaminepentaacetate (DTPA) and 1,4,7,10-tetraazacyclododecane-1,4,7,10-tetraacetic acid (DOTA). In one embodiment, the layer of amphiphatic molecules in the compositions provided herein includes 1,2-dimyristoyl-sn-glycero-3-phosphoethanolamine-N-DTPA.

In some embodiments, compositions provided herein include amphiphatic molecules that are derivatized with biotin, such as, for example, 1-(12-biotinyl(aminododecanoyl))-rac-glycerol. In other embodiments, compositions provided herein include amphiphatic molecules that are selected from among bioactive lipids, such as, for example, the VCAM inhibitor N-palmitoyl-serine phosphoric acid. In other embodiments, compositions provided herein include amphiphatic molecules that are selected from among fluorescent lipids and fatty acids, such as, for example, 1,2-dioleoyl-sn-glycero-3-phosphoethanolamine-N-(7-nitro-2-1,3-benzoxadiazol-4-yl) (phosphatidylethanolamine (NBD)) and 1-oleoyl-2-[6-[(7-nitro-2-1,3-benzoxadiazol-4-yl)amino]hexanoyl]-sn-glycero-3-phosphocholine (phosphatidylcholine (NBD)). In some other embodiments, compositions provided herein include amphiphatic molecules that include transfection lipids and molecules with hydrophobic domains coupled to the TAT peptide (trans-activating transcriptional activator peptide), or other protein transduction domains, which confer enhanced cellular entry of the bilayer coated nanoparticle (Torchilin, V. P, Rammohan, R., Weissig, V, Levchenko, T. S. PNAS, vol 98, no. 15, 8786-8791, 2001, herein incorporated by reference).

In other embodiments, compositions provided herein will include amphiphatic molecules that include reactive groups, charged groups, and/or functional groups other than the specific examples mentioned herein may be used unmodified or may be linked to other molecules, such as, for example, antibodies, drugs, nucleic acids, carbohydrates, lipids, proteins, peptides, aptamers, chelated metals, and other functional groups, to provide a modified coating. In some embodiments, the modified coating of the bilayer coated nanoparticle will aid in targeting or localizing the bilayer coated nanoparticle to certain biological tissues and/or cells in vivo and/or in vitro.

In some embodiments, the amphiphatic molecules are selected from among fatty acids and fatty acid derivatives, glycerolipids, glycerophospholipids, sterol lipids and sphingolipids. Fatty acids and fatty acid derivatives include, but are not limited to, fatty acids and conjugates, octadecanoids, eicosanoids, docosanoids, fatty alcohols, fatty aldehydes, fatty acid esters, and fatty acid amides. Glycerolipids, include, but are not limited to, monoradylglycerols, diradylglycerols, and triradylglycerols. Glycerophospholipids include, but are not limited to, phosphatidic acids, phosphatidylcholines, phosphatidylserines, phosphatidylglycerols, phosphatidylethanolamines, phosphatidylinositols, phosphatidylinositides, and cardiolipins. Sterol lipids include, but are not limited to, sterols, steroids, secosteroids, bile acids and derivatives. Sphingolipids include, but are not limited to, sphingoid bases, ceramides, phosphosphingolipids, phosphonosphingolipids, neutral glycosphinglipids, and acidic glycosphingolipids.

In some embodiments, the ampiphatic molecules of (b) are selected from among detergents, soaps, emulsifiers, surfactants, saturated fatty acids, unsaturated fatty acids, bile salts, monoglycerides, diglycerides, phospholipids, glycerophospholipids, sphingolipids, sterol lipids, sugar-linked lipids (glycolipids), protein linked lipids, and derivatives thereof.

In other embodiments, the ampiphatic molecules of (b) are selected from among sorbitan monolaurate, polyoxyethylene (20) sorbitan monolaurate (Tween® 20), sorbitan monopalmitate, polyoxyethylene (20) sorbitan monopalmitate (Tween®40), sorbitan monostearate, polyoxyethylene (20) sorbitan monostearate (Tween® 60), sorbitan monooleate, and polyoxyethylene (20) sorbitan monooleate (Tween® 80).

In some other embodiments, the ampiphatic molecules of (b) are selected from among phosphatidic acid, phosphatidylcholine, phosphatidylserine, phosphatidylglycerol, phosphatidylethanolamine, phosphatidylinositol, and bisphosphatidyl glycerol.

In other embodiments, the ampiphatic molecules of (b) are selected from among sodium dodecylsulfate, sodium cholate, sodium deoxycholate, taurocholic acid, N-lauroylsarcosine sodium salt, lauryldimethylamine-oxide, cetyltrimethylammonium bromide, and bis(2-ethylhexyl)sulfosuccinate sodium salt.

In some embodiments, the ampiphatic molecules of (b) are selected from among butyric acid, lauric acid (dodecanoic acid), myristic acid (tetradecanoic acid), palmitic acid (hexadecanoic acid), stearic acid (octadecanoic acid), arachidic acid (eicosanoic acid), linolenic acid, alpha-linolenic acid, docosahexaenoic acid, eicosapentaenoic acid, linoleic acid, arachidonic acid, oleic acid, erucic acid, stearidonic acid, eicosatetraenoic acid, gamma-linolenic acid, dihomo-gamma-linolenic acid, arachidonic acid, and alkali metal salts thereof.

In some embodiments, the ampiphatic molecules of (b) are selected from among:

Anionic Biological Detergents: chenodeoxycholic acid; chenodeoxycholic acid sodium salt; cholic acid; dehydrocholic acid; deoxycholic acid; deoxycholic acid methyl ester; digitonin; digitoxigenin; N,N-dimethyldodecylamine N-oxide; docusate sodium salt; glycochenodeoxycholic acid sodium salt; glycocholic acid hydrate; glycocholic acid sodium salt hydrate; glycodeoxycholic acid monohydrate; glycodeoxycholic acid sodium salt; glycolithocholic acid 3-sulfate; glycolithocholic acid ethyl ester; N-lauroylsarcosine sodium salt; lithium dodecyl sulfate; Lugol solution L6146; Niaproof 4; Triton QS-15, Triton QS-44; 1-octanesulfonic acid sodium salt; sodium 1-butanesulfonate, sodium 1-decanesulfonate, sodium 1-dodecanesulfonate, sodium 1-heptanesulfonate, sodium 1-nonanesulfonate, sodium 1-propanesulfonate; sodium 2-bromoethanesulfonate; sodium cholate hydrate, sodium choleate S9875; sodium deoxycholate, sodium deoxycholate monohydrate; sodium dodecyl sulfate; sodium hexanesulfonate anhydrous; sodium octyl sulfate; sodium pentanesulfonate, sodium pentanesulfonate anhydrous; sodium taurocholate; taurochenodeoxycholic acid sodium salt; taurodeoxycholic acid sodium salt monohydrate; taurohyodeoxycholic acid sodium salt hydrate; taurolithocholic acid 3-sulfate disodium salt; tauroursodeoxycholic acid sodium salt; Triton X-100, Triton X-200, Triton® XQS-20; Trizma® dodecyl sulfate; ursodeoxycholic acid.

Cationic Biological Detergents: alkyltrimethylammonium bromide; benzalkonium chloride; benzyldimethylhexadecylammonium chloride, benzyldimethyltetradecylammonium chloride; benzyldodecyldimethylammonium bromide; benzyltrimethylammonium tetrachloroiodate; dimethyldioctadecylammonium bromide; dodecylethyldimethylammonium bromide; dodecyltrimethylammonium bromide; dodecyltrimethylammonium bromide; ethylhexadecyldimethylammonium bromide; hexadecyltrimethylammonium bromide; hexadecyltrimethylammonium bromide; N,N',N'-polyoxyethylene(10)-N-tallow-1,3-diaminopropane; thonzonium bromide; trimethyl(tetradecyl)ammonium bromide, cetyltrimethylammonium bromide.

Non-Ionic Biological Detergents: BigCHAP (N,N-Bis[3-(D-gluconamido)propyl]cholamide); Bis(polyethylene glycol bis[imidazoyl carbonyl]); Brij® 35, Brij® 56, Brij® 72, Brij® 76, Brij® 92V, Brij® 97, Brij® 58P; Cremophor® EL; decaethylene glycol monododecyl ether; N-decanoyl-N-methylglucamine; n-decyl a-D-glucopyranoside; decyl b-D-maltopyranoside; n-dodecanoyl-N-methylglucamide; n-dodecyl a-D-maltoside; n-dodecyl b-D-maltoside; n-hexadecyl b-D-maltoside; heptaethylene glycol monodecyl ether; heptaethylene glycol monododecyl ether; heptaethylene glycol monotetradecyl ether; hexaethylene glycol monododecyl ether; hexaethylene glycol monohexadecyl ether; hexaethylene glycol monooctadecyl ether; hexaethylene glycol monotetradecyl ether; Igepal CA-630; methyl-6-O—(N-heptylcarbamoyl)-a-D-glucopyranoside; nonaethylene glycol monododecyl ether; N-nonanoyl-N-methylglucamine; N-nonanoyl-N-methylglucamine; octaethylene glycol monodecyl ether; octaethylene glycol monododecyl ether; octaethylene glycol monohexadecyl ether; octaethylene glycol monooctadecyl ether; octaethylene glycol monotetradecyl ether; octyl-b-D-glucopyranoside; pentaethylene glycol monodecyl ether; pentaethylene glycol monododecyl ether; pentaethylene glycol monohexadecyl ether; pentaethylene glycol monohexyl ether; pentaethylene glycol monooctadecyl ether; pentaethylene glycol monooctyl ether; polyethylene glycol diglycidyl ether; polyethylene glycol ether W-1; polyoxyethylene 10 tridecyl ether; polyoxyethylene 100 stearate; polyoxyethylene 20 isohexadecyl ether; polyoxyethylene 20 oleyl ether; polyoxyethylene 40 stearate; polyoxyethylene 50 stearate; polyoxyethylene 8 stearate, polyoxyethylene bis(imidazolyl carbonyl), polyoxyethylene 25 propylene glycol stearate; Saponin; Span® 20, Span® 40, Span® 60, Span® 65, Span® 80, Span® 85; Tergitol, Type 15-S-12, Tergitol, Type 15-S-30, Tergitol, Type 15-S-5, Tergitol, Type 15-S-7, Tergitol, Type 15-S-9, Tergitol, Type NP-10, Tergitol, Type NP-4, Tergitol, Type NP-40, Tergitol, Type NP-7, Tergitol, Type NP-9, Tergitol; tetradecyl-b-D-maltoside; tetraethylene glycol monodecyl ether, tetraethylene glycol monododecyl ether, tetraethylene glycol monotetradecyl ether; triethylene glycol monodecyl ether, triethylene glycol monododecyl ether, triethylene glycol monohexadecyl ether, triethylene glycol monooctyl ether, triethylene glycol monotetradecyl ether; Triton® CF-21, Triton® CF-32, Triton® DF-12, Triton® DF-16, Triton® GR-5M, Triton® X-100, Triton® X-102, Triton® X-15, Triton® X-151, Triton® X-207, Triton® X-114, Triton® X-165, Triton® X-305, Triton® X-405, Triton® X-45, Triton® X-705-70; TWEEN®20, TWEEN® 21, TWEEN® 40, TWEEN® 60, TWEEN® 61, TWEEN® 65, TWEEN® 80, TWEEN® 81, TWEEN® 85; Tyloxapol; n-undecyl b-D-glucopyranoside.

Zwitterionic Biological Detergents: CHAPS (3-[(3-Cholamidopropyl)dimethylammonio]-1-propanesulfonate); CHAPSO (3-([3-Cholamidopropyl]dimethylammonio)-2-hydroxy-1-propanesulfonate); 3-(decyldimethylammonio) propanesulfonate inner salt; 3-(dodecyldimethylammonio) propanesulfonate inner salt; 3-(N,N-dimethylmyristylammonio)propanesulfonate; 3-(N,N-dimethyloctadecylammonio)propanesulfonate; 3-(N,N-dimethyloctylammonio)propanesulfonate inner salt; 3-(N,N-dimethylpalmitylammonio)propanesulfonate.

Saturated Alkyl Acids: butanoic acid (butyric acid), pentanoic acid (valeric acid), hexanoic acid (caproic acid), heptanoic acid (enanthic acid), octanoic acid (caprylic acid), nonanoic acid (pelargonic acid), decanoic acid (capric acid), undecanoic acid (undecylic acid), dodecanoic acid (lauric acid), tridecanoic acid (tridecylic acid), tetradecanoic acid (myristic acid), pentadecanoic acid (pentadecylic acid), hexadecanoic acid (palmitic acid), heptadecanoic acid (margaric acid), octadecanoic acid (stearic acid), nonadecanoic acid (nonadecylic acid), eicosanoic acid (arachidic acid), heneicosanoic acid, docosanoic acid (behenic acid), tricosanoic acid, tetracosanoic acid (lignoceric acid), pentacosanoic acid, hexaconsanoic acid (cerotic acid), heptacosanoic acid, octacosanoic acid (montanic acid), nonacosanoic acid, triacontanoic acid (melissic acid), hentriacontanoic acid.

Unsaturated fatty acids: 10-undecenoic acid (10-undecylenic acid), cis-9-tetradecenoic acid (myristoleic acid), trans-9-tetradecenoic acid (myristelaidic acid), 9-tetradecynoic acid, cis-10-pentadecenoic acid cis-9-hexadecenoic acid (palmitoleic acid), trans-9-hexadecenoic acid (palmitelaidic acid), cis-10-heptadecenoic acid, cis-6-octadecenoic acid (petroselinic acid), trans-6-octadecenoic acid, cis-7-octadecenoic acid, trans-7-octadecenoic acid, cis-9-octadecenoic acid (oleic acid), trans-9-octadecenoic acid (elaidic acid), 9-octadecynoic acid (stearolic acid), cis-11-octadecenoic acid (cis-vaccenic acid), trans-11-octadecenoic acid (trans-vaccenic acid), cis-12-octadecenoic acid, trans-12-octadecenoic acid, cis-13-octadecenoic acid, trans-13-octadecenoic acid, cis-15-octadecenoic acid, 17-octadecynoic acid, cis-12-hydroxy-9-octadecenoic acid (ricinoleic acid), trans-12-hydroxy-9-octadecenoic acid (ricinelaidic acid), cis-9,12-octadecadienoic acid (linoleic acid), trans-9,12-octadecadienoic acid (linolenelaidic acid), 9,11(10,12)-octadecadienoic acid, cis-6,9,12-octadecatrienoic acid (γ-linolenic acid), cis-9,12,15-octadecatrienoic acid (linolenic acid), trans-9,12,15-octadecatrienoic acid (linolenelaidic acid), cis-6,9,12,15-octadecatetraenoic acid, cis-10-nonadecenoic acid, cis-5-eicosenoic acid, cis-8-eicosenoic acid, cis-11-eicosenoic acid (gondoic acid), trans-11-eicosenoic acid, cis-13-eicosenoic acid, 13-eicosynoic acid, cis-11,14-eicosadienoic acid, cis-5,8,11-eicosatrienoic acid, 5,8,11-eicosatriynoic acid, cis-8,11,14-eicosatrienoic acid, 8,11,14-eicosatriynoic acid, cis-11,14,17-eicosatrienoic acid, cis-5,8,11,14-eicosatetraenoic acid (arachidonic acid), cis-5,8,11,14,17-eicosapentaenoic acid, cis-13-docosenoic acid (erucic acid), trans-13-docosenoic acid (brassidic acid), cis-13,16-docosadienoic acid, cis-13,16,19-docosatrienoic acid, cis-7,10,13,16-docosatetraenoic acid, cis-7,10,13,16,19-docosapentaenoic acid, cis-4,7,10,13,16,19-docosahexaenoic acid, cis-15-tetracosenoic acid (nervonic acid).

Saturated Alkyl Aldehydes: butanal, pentanal, hexanal, heptanol, octanal, nonanal, decanal, undecanal, dodecanal, tridecanal, tetradecanal, pentadecanal, hexadecanal, heptadecanal, octadecanal, nonadecanal, eicosanal, heneicosanal, docosanal, tricosanal, tetracosanal, pentacosanal, hexacosanal, heptacosanal, octacosanal, nonacosanal, triacontanal, hentriacontanal.

Unsaturated Alkyl Aldehydes: 10-undecenal, cis-9-tetradecenal, trans-9-tetradecenal, 9-tetradecynal, cis-10-pentadecenal, cis-9-hexadecenal, trans-9-hexadecenal, cis-10-heptadecenal, cis-6-octadecenal, trans-6-octadecenal, cis-7-octadecenal, trans-7-octadecenal, cis-9-octadecenal, trans-9-octadecenal, 9-octadecynal, cis-11-octadecenal, trans-11-octadecenal, cis-12-octadecenal, trans-12-octadecenal, cis-13-octadecenal, trans-13-octadecenal, cis-15-octadecenal, 17-octadecynal, cis-12-hydroxy-9-octadecenal, trans-12-hydroxy-9-octadecenal, cis-9,12-octadecadienal, trans-9,12-octadecadienal, 9,11(10,12)-octadecadienal, cis-6,9,12-octadecatrienal, cis-9,12,15-octadecatrienal, trans-9,12,15-octadecatrienal, cis-6,9,12,15-octadecatetraenal, cis-10-nonadecenal, cis-5-eicosenal, cis-8-eicosenal, cis-11-eicosenal, trans-11-eicosenal, cis-13-eicosenal, 13-eicosynal, cis-11,14-eicosadienal, cis-5,8,11-eicosatrienal, 5,8,11-eicosatriynal, cis-8,11,14-eicosatrienal, 8,11,14-eicosatriynal, cis-11,14,17-eicosatrienal, cis-5,8,11,14-eicosatetraenal, cis-5,8,11,14,17-eicosapentaenal, cis-13-docosenal, trans-13-docosenal, cis-13,16-docosadienal, cis-13,16,19-docosatrienal, cis-7,10,13,16-docosatetraenal, cis-7,10,13,16,19-docosapentaenal, cis-4,7,10,13,16,19-docosahexaenal, cis-15-tetracosenal.

Glycerophosphates: 1,2-di(cis-9-octadecenoyl)-sn-glycerol 3-phosphate sodium salt; 1,2-didecanoyl-sn-glycerol 3-phosphate sodium salt; 1,2-diheptadecanoyl-sn-glycerol 3-phosphate sodium salt; 1,2-dimyristoyl-sn-glycero-3-phosphate disodium salt; 1,2-dimyristoyl-sn-glycero-3-phosphate monosodium salt; 1,2-dioctanoyl-sn-glycerol 3-phosphate sodium salt; 1,2-dioleoyl-sn-glycero-3-phosphoric acid sodium salt; 1,2-dipalmitoyl-sn-glycero-3-phosphate calcium salt; 1,2-dipalmitoyl-sn-glycero-3-phosphate disodium salt; 1,2-dipalmitoyl-sn-glycero-3-phosphate monosodium salt; 1,2-dipalmitoyl-sn-glycero-3-phosphate sodium salt; 1,2-dipalmitoyl-sn-glycerol 3-phosphate diphenyl ester; 1,2-distearoyl-sn-glycero-3-phosphate sodium salt; 1-oleoyl-sn-glycero-3-phosphate sodium salt; 3-sn-phosphatidic acid sodium salt; L-α-phosphatidyl-DL-glycerol ammonium salt; L-α-phosphatidyl-DL-glycerol sodium salt; Lipid A, monophosphorylated; oleoyl-L-α-lysophosphatidic acid sodium salt; rac-1,2-dipalmitoyl-glycero-3-phosphate disodium salt.

Glycerophosphocholines: 1,2-dimyristoylamino-1,2-dideoxyphosphatidylcholine; D-α-phosphatidylcholine, dipalmitoyl; DL-α-phosphatidylcholine, distearoyl; L-α-lysophosphatidylcholine; L-α-phosphatidylcholine; β-acetyl-γ-O-alkyl-L-α-phosphatidylcholine; β-acetyl-γ-O-hexadecyl-L-α-phosphatidylcholine.

Glycerophosphoethanolamines: 1,2-dipalmitoyl-rac-glycero-3-phospho(dimethylaminoethanol); 3-sn-lysophosphatidylethanolamine; 3-sn-phosphatidylethanolamine; L-α-phosphatidylethanolamine; L-α-phosphatidylethanolamine, dioleoyl; L-α-phosphatidylethanolamine, dipalmitoyl, N-dansyl; L-α-phosphatidylethanolamine, distearoyl methoxypolyethylene glycol conjugate; phosphatidylethanolamine, dioleoyl, N-dansyl.

Glycerophosphoglycerols: 1,2-dihexadecanoyl-rac-glycero-3-phospho-rac-(1-glycerol) ammonium salt; 1,2-dimyristoyl-sn-glycero-3-phospho-rac-(1-glycerol) sodium salt; 1,2-dioctadecanoyl-sn-glycero-3-phospho-rac-(1-glycerol) ammonium salt; 1,2-dioleoyl-sn-glycero-3-phospho-rac-(1-glycerol) sodium salt; 1,2-dipalmitoyl-sn-glycero-3-phospho-rac-(1-glycerol) sodium salt; 1-(3-sn-phosphatidyl)-rac-glycerol ammonium salt; 1-(3-sn-phosphatidyl)-rac-glycerol sodium salt; 1-palmitoyl-2-oleoyl-sn-glycero-3-phospho-rac-(1-glycerol) ammonium salt.

Glycerophosphogycerophosphoglycerols (cardiolipins): cardiolipin disodium salt; cardiolipin.

Glycerophosphoinositol bisphosphates: phosphatidylinositol 4,5-bisphosphate disodium salt).

Glycerophosphoinositol monophosphates: L-α-phosphatidyl-D-myo-inositol 3-monophosphate, dioctanoyl; L-α-phosphatidyl-D-myo-inositol 3-monophosphate, dipalmitoyl; L-α-phosphatidyl-D-myo-inositol 4-monophosphate, dioctanoyl; L-α-phosphatidyl-D-myo-inositol 4-monophosphate, dipalmitoyl; L-α-phosphatidyl-D-myo-inositol 5-monophosphate, dioctanoyl; L-α-phosphatidyl-D-myo-inositol 5-monophosphate, dipalmitoyl; L-α-phosphatidylinositol 4-monophosphate sodium salt.

Glycerophosphoinositol trisphosphates: 1,2-dipalmitoylphosphatidylinositol 3,4,5-trisphosphate.

Glycerophosphoinositols: 1,2-dipalmitoylphosphatidylinositol 3,4-diphosphate; 1,2-dipalnitoylphosphatidylinositol 4,5-diphosphate; L-α-lysophosphatidylinositol sodium salt; L-α-phosphatidyl-D-myo-inositol 3,4,5-triphosphate, dioctanoyl; L-α-phosphatidyl-D-myo-inositol 3,4-diphosphate, dioctanoyl; L-α-phosphatidyl-D-myo-inositol 3,5-diphosphate, dioctanoyl; L-α-phosphatidyl-D-myo-inositol 3,5-diphosphate, dipalmitoyl; L-α-phosphatidyl-D-myo-inositol 4,5-diphosphate, dioctanoyl; L-α-phosphatidylinositol 4,5-diphosphate sodium salt; L-α-phosphatidylinositol ammonium salt; L-α-phosphatidylinositol dipalmitoyl ammonium salt; L-α-phosphatidylinositol; L-α-phosphatidylinositol sodium; phosphatidylinositol 4-phosphate sodium salt; phosphatidylinositol ammonium salt; phosphatidylinositol sodium salt; phosphoinositides sodium salt.

Glycerophosphonocholines: 1,2-di(palmitoyl-d31)-sn-glycero-3-phosphocholine; 1,2-di-O-hexadecyl-sn-glycero-3-phosphocholine; 1,2-diarachidoyl-sn-glycero-3-phosphocholine; 1,2-dibutyryl-sn-glycero-3-phosphocholine; 1,2-didecanoyl-sn-glycero-3-phosphocholine; 1,2-didocosanoyl-sn-glycero-3-phosphocholine; 1,2-didodecanoyl-rac-glycero-3-phosphocholine; 1,2-didodecanoyl-sn-glycero-3-phosphocholine; 1,2-dielaidoyl-sn-glycero-3-phosphocholine; 1,2-diheptanoyl-sn-glycero-3-phosphocholine; 1,2-dihexadecyl-rac-glycero-3-phosphocholine; 1,2-dihexadecyl-sn-glycero-3-phosphocholine dihydrate; 1,2-dihexanoyl-sn-glycero-3- phosphocholine; 1,2-dilinoleoyl-sn-glycero-3-phosphocholine; 1,2-dimyristoyl-rac-glycero-3-phosphocholine, 1,2-dimyristoyl-sn-glycero-3-phosphocholine; 1,2-dinonanoyl-sn-glycero-3-phosphocholine; 1,2-dioleoyl-sn-glycero-3-phosphocholine; 1,2-dipalmitoyl-rac-glycero-3-phosphocholine; 1,2-dipamitoyl-sn-glycero-3-phosphocholine; 1,2-dipentadecanoyl-sn-glycero-3-phosphocholine; 1,2-distearoyl-sn-glycero-3-phosphocholine; 1,2-diundecanoyl-sn-glycero-3-phosphocholine; 1-dodecanoyl-sn-glycero-3-phosphocholine; 1-heptadecanoyl-sn-glycero-3-phosphocholine; 1-hexanoyl-sn-glycero-3-phosphocholine; 1-myristoyl-2-oleoyl-sn-glycero-3-phosphocholine; 1-myristoyl-sn-glycero-3-phosphocholine; 1-myristoyl-sn-glycero-3-phosphocholine; 1-O-(cis-9-octadecenyl)-2-acetyl-sn-glycero-3-phosphocholine; 1-O-octadecyl-2-O-methyl-sn-glycero-3-phosphorylcholine; 1-O-palmityl-2-(cis-8,11,14-eicosatrienoyl)-sn-glycero-3-phosphocholine; 1-O-palmityl-2-acetyl-rac-glycero-3-phosphocholine; 1-O-palmityl-2-arachidonoyl-sn-glycero-3-phosphocholine; 1-O-palmityl-2-O-methyl-rac-glycero-3-phosphocholine; 1-O-palmityl-2-palmitoyl-rac-glycero-3-phosphocholine; 1-O-palmityl-rac-glycero-3-phosphocholine; 1-O-palmityl-sn-glycero-3-phosphocholine; 1-oleoyl-2-palmitoyl-sn-glycero-3-phosphocholine; 1-oleoyl-sn-glycero-3-phosphocholine; 1-palmitoyl-2-(cis-4,7,10,13,16,19-docosahexaenoyl)-sn-glycero-3-phosphocholine; 1-palmitoyl-2-(pyrene-1-yl)decanoyl-sn-glycero-3-phosphocholine; 1-palmitoyl-rac-glycero-3-phosphocholine, 1-palmitoyl-sn-glycero-3-phosphocholine; 1-stearoyl-2-linoleoyl-sn-glycero-3-phosphocholine; 1-stearoyl-sn-glycero-3-phosphocholine; 2,3-didocecanoyl-sn-glycero-1-phosphocholine; 2,3-dipalmitoyl-sn-glycero-1-phosphocholine; 2-arachidonoyl-1-palmitoyl-sn-glycero-3-phosphocholine; 2-arachidonoyl-1-stearoyl-sn-glycero-3-phosphocholine; 2-linoleoyl-1-palmitoyl-sn-glycero-3-phosphocholine; 2-oleoyl-1-palmitoyl-sn-glycero-3-phosphocholine; 2-oleoyl-1-stearoyl-sn-glycero-3-phosphocholine; rac-1,2-dipalmitoyl-glycero-3-phosphocholine monohydrate.

Glycerophosphonoethanolamines: 1,2-didodecanoyl-sn-glycero-3-phosphoethanolamine; 1,2-diheptadecanoyl-sn-glycero-3-phosphoethanolamine; 1,2-dihexadecyl-sn-glycero-3-phosphoethanolamine; 1,2-dimyristoyl-sn-glycero-3-phosphoethanolamine; 1,2-dioleoyl-sn-glycero-3-phosphoethanolamine; 1,2-dipalmitoyl-rac-glycero-3-phosphoethanolamine; 1,2-dipalmitoyl-sn-glycero-3-phospho(N-palmitoyl)ethanolamine ammonium salt; 1,2-dipalmitoyl-sn-glycero-3-phospho(N-succinylethanolamine) sodium salt; 1,2-dipalmitoyl-sn-glycero-3-phospho-N,N-dimethylethanolamine; 1,2-dipalmitoyl-sn-glycero-3-phospho-N-methylethanolamine; 1,2-dipalmitoyl-sn-glycero-3-phosphoethanolamine; 1,2-distearoyl-sn-glycero-3-phosphoethanolamine; 2-linoleoyl-1-palmitoyl-sn-glycero-3-phosphoethanolamine; 2-oleoyl-1-palmitoyl-sn-glycero-3-phosphoethanolamine; N-(NBD)-aminododecanoyl-1,2-dioleoyl-sn-glycero-3-phosphoethanolamine sodium salt.

Glycerophosphoserines: 1,2-diacyl-sn-glycero-3-phospho-L-serine; 1,2-dioleoyl-sn-glycero-3-phospho-L-serine sodium salt; 1,2-dipalmitoyl-rac-glycero-3-phospho-L-serine; 1,2-dipalmitoyl-sn-glycero-3-phospho-L-serine sodium salt; 3-sn-phosphatidyl-L-serine sodium salt; 3-sn-phosphatidyl-L-serine; L-α-phosphatidyl-L-serine.

Neutral Glycerides

Diradylglycerols: 1,2-di-O-hexadecyl-rac-glycerol; 1,2-dimyristoyl-3-palmitoyl-rac-glycerol; 1,2-dimyristoyl-rac-glycerol; 1,2-dioctanoyl-sn-glycerol; 1,2-dioleoyl-rac-glycerol; 1,2-dioleoyl-sn-glycerol; 1,2-dipalmitoyl-3-iodo-3-deoxy-rac-glycerol; 1,2-dipalmitoyl-rac-glycerol, 1,2-dipalmitoyl-sn-glycerol; 1,2-distearoyl-rac-glycerol; 1,3-dielaidin; 1,3-dierucin; 1,3-dilinoleoyl-rac-glycerol; 1,3-dimyristin; 1,3-diolein; 1,3-dipentadecanoin; 1-O-palmityl-2-acetyl-rac-glycerol; 1-O-palmityl-2-O-methyl-sn-glycerol; 1-oleoyl-2-acetyl-sn-glycerol; 1-palmitoyl-3-stearoyl-rac-glycerol; 1-stearoyl-2-arachidonoyl-sn-glycerol; 2,3-dimyristoyl-sn-glycerol; dilaurin; diolein; dioleoylglycerol; dipalmitin; distearoylglycerol; glyceryl 1,3-didodecanoate; glyceryl 1,3-dipalmitate; glyceryl 1,3-distearate, Monoradylglycerols: 1-(cis-13-docosenoyl)-rac-glycerol; 1-decanoyl-rac-glycerol; 1-lauroyl-rac-glycerol; 1-linolenoyl-rac-glycerol; 1-monopalmitoleoyl-rac-glycerol; 1-O-palmityl-rac-glycerol; 1-octanoyl-rac-glycerol; 1-oleoyl-rac-glycerol; 1-stearoyl-rac-glycerol; 2-oleoylglycerol; 3-palmitoyl-sn-glycerol; 3-stearoyl-sn-glycerol; DL-α-palmitin; monoolein; rac-glycerol 1-myristate.

Triradylgylcerols: 1,2-didodecanoyl-3-tetradecanoyl-rac-glycerol; 1,2-dilinoleoyl-3-oleoyl-rac-glycerol; 1,2-dilinoleoyl-3-palmitoyl-rac-glycerol; 1,2-dimyristoyl-3-lauroyl-rac-glycerol; 1,2-dimyristoyl-3-palmitoyl-rac-glycerol; 1,2-dioleoyl-3-linoleoyl-rac-glycerol; 1,2-dioleoyl-3-palmitoyl-rac-glycerol; 1,2-dioleoyl-3-stearoyl-rac-glycerol; 1,2-dipalmitoyl-3-myristoyl-rac-glycerol; 1,2-dipalmitoyl-3-O-benzyl-rac-glycerol; 1,2-distearoyl-3-oleoyl-rac-glycerol; 1,2-distearoyl-3-palmitoyl-rac-glycerol; 1,3-dioleoyl-2-palmitoylglycerol; 1,3-dipalmitoyl-2-oleoylglycerol; 1-lauroyl-2-oleoyl-3-palmitoyl-rac-glycerol; 1-linoleoyl-2-oleoyl-3-stearoyl-rac-glycerol; 1-O-palmityl-2,3-dipalmitoyl-rac-glycerol; 1-palmitoyl-2-oleoyl-3-linoleoyl-rac-glycerol; glycerol triarachidate, glycerol trihexanoate; glyceryl tri(cis-13-docosenoate); glyceryl triacetate, glyceryl tributyrate, glyceryl tridecanoate, glyceryl tridodecanoate, glyceryl trielaidate, glyceryl triheptadecanoate, glyceryl trilinoleate, glyceryl trilinolenate, glyceryl trimyristate, glyceryl trinervonate, glyceryl trinonadecanoate, glyceryl trinonanoate, glyceryl trioctanoate, glyceryl trioleate, glyceryl tripalmitate, glyceryl tripalmitelaidate, glyceryl tripalmitoleate, glyceryl tripetroselinate, glyceryl tristearate, glyceryl tritricosanoate, glyceryl tritridecanoate; rac-1,2-dimyristoyl-3-oleoylglycerol; triacetin; tribehenin; tributyrin; tricaprin; triolein; tripentadecanoin; tripetroselaidin.

Sphingolipids

Ceramides: ceramide 1-phosphates; D-erythro-Ceramide C8 1-phosphate; ceramide 1-phosphate.

N-acyl-4-hydroxysphinganines (phytoceramides): Phytoceramide C2.

N-acylsphinganines (dihydrocerarmides): dihydroceramide C2; dihydroceramide C6; dihydroceramide C8; N-lignoceroyl-DL-dihydrosphingosine; N-palmitoyl-DL-dihydrogalactocerebroside; N-stearoyl-DL-dihydrolactocerebroside.

N-acylsphingosines (ceramides): D-erythro-ceramine C8; ceramide; N-acetyl-D-sphingosine, N-hexanoyl-D-sphingosine; N-octanoyl-D-sphingosine, N-oleoyl-D-sphingosine; N-tetracosanoyl-D-sphingosine 1-benzoate; non-hydroxy fatty acid ceramide.

Neutral glycosphingolipids: Galactocerebrosides; globotriaosylsphingosine; glucocerebrosides; lactocerebrosides; psychosine.

Phosphosphingolipids: N-palmitoyl-D-sphingomyelin; sphingomyelin; sphingosylphosphorylcholine; ceramide phosphorylethanolamine.

Sphingoid bases: N,N,N-trimethylsphingosine chloride salt; D-sphingosine; L-erythro-sphingosine; D-erythro-dihydrosphingosine, D-threo-dihydrosphingosine, DL-dihydrosphingosine, DL-erythro-dihydrosphingosine, DL-threo-dihydrosphingosine, L-threo-dihydrosphingosine; D-erythro-dihydrosphingosine 1-phosphate; sphingosine 1-phosphate.

Sterols

Bile acids and Derivatives: 5-cholenic acid-3β-ol; chenodeoxycholic acid; cholic acid; dehydrocholic acid; deoxycholic acid; lithocholic acid; sodium cholate hydrate; sodium dehydrocholate; sodium deoxycholate; sodium glycochenodeoxycholate; sodium taurochenodeoxycholate; sodium taurocholate hydrate; taurocholic acid sodium salt hydrate; ursodeoxycholic acid.

Cholesterol and Derivatives: 22(R)-hydroxycholesterol, 22(S)-hydroxycholesterol; 25-hydroxycholesterol; 5-cholesten-3β-ol-7-one; 5α-cholest-7-en-3β-ol; 5α-cholestan-3β-ol; 5α-cholestane; 5β-cholestan-3α-ol; 7β-hydroxycholesterol; campesterol; cholesta-3,5-diene; cholestanol; cholesterol 5α,6α-epoxide, cholesterol 5β,6β-epoxide; cholesterol-PEG 600; cholesterol; cholesteryl 10-undecenoate, cholesteryl acetate, cholesteryl arachidonate, cholesteryl behenate, cholesteryl butyrate, cholesteryl caprylate, cholesteryl dodecanoate, cholesteryl elaidate, cholesteryl erucate, cholesteryl heptadecanoate, cholesteryl heptanoate, cholesteryl hexanoate, cholesteryl linoleate, cholesteryl linolelaidate, cholesteryl myristate, cholesteryl N-(trimethylammonioethyl)carbamate chloride, cholesteryl n-decanoate, cholesteryl n-valerate, cholesteryl nervonate, cholesteryl oleate, cholesteryl palmitate, cholesteryl palmitelaidate, cholesteryl pelargonate, cholesteryl phenylacetate, cholesteryl stearate; glycocholic acid hydrate; lanosterol; sodium cholesteryl sulfate; stigmastanol; SyntheChol®; Thiocholesterol.

Estrogens and Derivatives: 17α-ethynylestradiol; 2-methoxyestradiol 3-methyl ether; estriol 16α-(β-D-glucuronide); estrone 3-(βD-glucuronide) sodium salt.

Phytosterols and Derivatives: β-sitosterol.

Steroids and Derivatives: testosterone acetate, testosterone propionate; 6α-methylprednisolone; corticosterone; cortisone; dexamethasone 21-phosphate disodium salt.

Prenols

Ubiquinones: Coenzyme Q10, Coenzyme Q1, Coenzyme Q2, Coenzyme Q4, Coenzyme Q4, Coenzyme Q9.

Vitamin E: (±)-α-tocopherol nicotinate, (±)-α-tocopherol phosphate disodium salt, (±)-α-tocopherol, (+)-α-tocopherol acetate, (+)-α-tocopherol acid succinate, D-αtocopherol succinate, DL-α-tocopherol acetate, DL-α-tocopherol, α-tocopherol, δ-tocopherol, γ-tocopherol; vitamin E acetate.

Vitamin K: phylloquinone (K1); vitamin K1; vitamin K2.

In some embodiments, the amphiphatic molecules in the compositions provided herein are identical or derived from moieties having the same chemical structure.

In other embodiments, more than one surface binding molecule and/or more than one amphipahtic molecule may be used to form the bilayer coating in the compositions provided herein. In some embodiments, it may be desirable to space apart the number of reactive groups that are exposed to the environment and/or to limit reactivity. In some other embodiments, it may be desirable to limit or reduce the number of reactive functional groups that are exposed to the environment. This may be done by using a combination of amphiphatic molecules that have different hydrophilic groups with varying degrees of reactivity. For example, in one embodiment, compositions provided herein include two types of amphiphatic molecules: one type of amphiphatic molecule includes, for example, a hydrophilic moiety that confers water solubility but is not reactive, is mixed with another type of amphiphatic molecules that include a hydrophilic moiety that is reactive. In one embodiment, the number and identity of reactive functional groups on the surface of the bilayer coatings provided herein is controlled by adjusting the proportion of each type of amphiphatic molecule that is added to form the compositions provided herein.

Additional Stability of Hydrophobic Region—Cross Linking

In some embodiments, the moieties of the molecules that form the bilayer coating provided herein may be crosslinked for additional stability. For example, in one embodiment, the hydrophobic moieties of the surface binding molecules may be crosslinked to provide a monolayer of surface binding molecules that has increased stability, which now has covalent bonds linking the lateral molecules as compared to hydrophobic interactions that are present without the effects of crosslinking. In another embodiment, the hydrophobic moieties of the surface binding molecules and/or the hydrophobic moieties of the amphiphatic molecules are crosslinked for additional stability.

In one embodiment, the hydrophobic moieties in the bilayer coatings that coat the nanoparticles, may be crosslinked. For example, the presence of double bonds in the hydrophobic moieties may be covalently linked together by polymerization reactions, such as, for example, free radical polymerization, cationic polymerization, anionic polymerization, metal catalyzed polymerization. The presence of acrylate moieties in the hydrophilic and/or hydrophobic domains of the bilayer coatings that coat the nanoparticles may also be crosslinked by polymerization reactions. In one embodiment, the use of unsaturated fatty acids as the surface binding molecules and/or amphiphatic molecules in the bilayer coating provided herein, can provided a means for crosslinking the layer of molecules by polymerizing the alkene-containing molecules. In another embodiment, the double bonds, if present on adjacent molecules in the bilayer coatings that coat the nanoparticles can be crosslinked by use of a metal oxo catalyst, such as, for example, osmium tetroxide or permanganate. Use of osmium tetroxide and/or permanganate to crosslink the double bonds of adjacent molecules is a way to introduce a heavy metal into the bilayer coating. The presence of a heavy metal, such as, for example, osmium or manganese into the bilayer coating could aid in detectability of the bilayer coated nanoparticle, use with electron microscopy, use in vivo as a drug or for absorption of X-rays for contrast or therapy. Use of permanganate introduces the manganese atom which is useful as a contrast agent for magnetic resonance imaging (MRI). The nanoparticles that are coated can also include a heavy metal that also absorbs radiation. In another embodiment, the nanoparticle that is coated can also includes an active MRI agent. This strategy provides a way to add additional stability to the bilayer coating and/or to provide a means for introducing additional heavy metals into a composition without toxic effects in in vivo or in vitro uses. The presence of multiple heavy atoms in a single composition can provide a means of using a single composition in two different imaging applications, such as, for example, in X-ray imaging and MRI.

In some embodiments, the hydrophilic moieties of the amphiphatic molecules, which face the environment, are crosslinked to provide additional stability. In one embodiment, the hydrophilic moieties of the amphiphatic molecules may be linked with a bifunctional crosslinker that links some of the outer hydrophilic moieties of the amphiphatic molecules. For example, if the amphiphatic molecules forming the bilayer coating include 1-aminododecane, then the amino groups of the 1-aminododecane molecules can be crosslinked with, but not limited to, glutaraldehyde and/or bis(sulfosuccinimidyl)suberate.

In any of the crosslinking strategies, the crosslinking can be executed after the bilayer coating forms on the nanoparticle.

Organic Solvents and Hydrophobic Environments

The compositions and methods provided herein may be easily modified to provide compositions that are soluble in organic solvents or hydrophobic environments. In one embodiment, the surface binding molecules that form the bilayer coating include: i) a binding moiety that that has an affinity for the nanoparticle; and ii) a hydrophilic moiety that non-covalently binds to a hydrophilic moiety of the amphiphatic molecules. The amphiphatic molecules will include: i) a hydrophilic moiety that non-covalently binds to the hydrophilic moiety of the surface binding molecules; and ii) a hydrophobic moiety that faces the organic or hydrophobic environment. In this case, the surface binding molecules and the amphiphatic molecules interact by means of hydrophilic interactions, such as, for example, by hydrogen bonding and/or ionic interactions and/or electrostatic interactions.

The bilayer coatings that coat the nanoparticle are modular in design and can be readily assembled by using commercial available molecules. The properties of the bilayer coating can be readily modified in order to provide stable compositions Formation of Bilayer Coated Nanoparticles Compositions provided herein include nanoparticles that are coated with a bilayer of molecules. The bilayer coatings disclosed herein are made from surface binding molecules and amphiphatic molecules. The surface binding molecules provided herein include a hydrophobic moiety and a binding moiety that has an affinity for the surface to be coated. In some embodiments, the binding moiety of the surface binding molecules is polar and/or hydrophilic. The amphiphatic molecules provided herein include a hydrophobic moiety and a hydrophilic moiety.

Nanoparticles can be prepared by methods disclosed herein or by methods known in the art. For example, in some embodiments, nanoparticles are prepared by methods disclosed in: U.S. Pat. No. 6,818,199; U.S. Pat. No. 6,645,464; U.S. Pat. No. 6,670,113; U.S. Pat. No. 6,521,773; U.S. Pat. No. 6,534,039, U.S. Pat. No. 6,369,206; U.S. Pat. No. 6,121,425; U.S. Pat. No. 5,443,813; U.S. Pat. No. 5,521,289; U.S. Pat. No. 5,690,903; U.S. Pat. No. 5,360,895; U.S. Pat. No. 6,955,639; Love, J. C., Estroff, L. A.; Kriebel, J. K., Nuzzo, R. G., Whitesides, G. M. Chem. Rev. 2005, 105, 1103-1169; Ulman, A. Chem. Rev. 1996, 96, 1533-1554; Hoeben, F. J. M., Jonkhejim, P, Meijer, E. W., Schenning, A. P. H. J. Chem. Rev. 2005, 105, 1491-1546; Daniel M, Didier, A. Chem. Rev. 2004, 104, 293-346; all of which are herein incorporated by reference.

In some embodiments, mixing together surface binding molecules with amphiphatic molecules, wherein each molecule has a hydrophobic moiety and a hydrophilic moiety, in an aqueous solvent may lead to the formation of micelles and other surfactant structures such as, for example, liposomes, cubosomes, bilayers and/or multilayers. Some of these states or forms may be less advantageous or not work at all to form the desired bilayer coatings described herein. For example, if the surface binding molecules and the amphiphatic molecules are each in a micellar state, then mixing them together may not produce the desired bilayer coatings. In other embodiments, the surface binding molecules and the amphiphatic molecules will interact with each other by means of their hydrophobic moieties. In some embodiments, the formation of stable micelles, bilayers, multilayers, liposomes, and/or cubosomes may prevent the self assembly of the molecules into a bilayer coating on the nanoparticles.

In one embodiment, surface binding molecules and amphiphatic molecules are mixed together and form an intermediate composition, wherein the hydrophobic moieties of the molecules interact with each other. However, these hydrophobic interactions between the molecules may lead to the formation of stable micelles, bilayers, multilayers, liposomes, and/or cubosomes that may prevent the self assembly of the molecules into a bilayer on the surface to be coated. The formation of micelles, bilayers, multilayers, liposomes, and/or cubosomes may be prevented by mixing the molecules that form the bilayer coating near or below the critical micelle concentration (CMC) of the individual molecules. However, this strategy requires low concentrations of molecules and the formation of the intermediate surface binding molecule-amphiphatic molecule composition may also dissociate under these conditions.

In one embodiment, compositions provided herein are formed by mixing surface binding molecules and amphiphatic molecules at high concentrations, well above their aqueous CMC, in a water miscible solvent, such as, for example, an alcohol solvent, such as, for example, ethanol. Under these conditions, the surface binding molecules and the amphiphatic molecules will form an intermediate composition/complex. The concentrated mixture of the surface binding molecules and amphiphatic molecules will then form a bilayer coating when exposed to a nanoparticle. Using this strategy for coating surfaces, bilayers form on the nanoparticles wherein the surface binding molecules bind tightly to the nanoparticle by means of the reactive moieties and the hydrophobic moieties of the surface binding moieties face away from the nanoparticle and interact through hydrophobic interactions with the amphiphatic molecules, which form a layer on the layer of the surface binding molecules. The presence of the hydrophilic moieties on the amphiphatic molecules, which face the environment, provide desirable properties to the bilayer coated nanoparticles such as, but not limited to, water solubility, biocompatibility, and/or reduced toxicity. If only surface binding molecules bound to the nanoparticles, then the hydrophobic tails of the surface binding molecules would face the environment and render the monolayer coated nanoparticle hydrophobic and water insoluble.

The premixing of the surface binding molecules and the amphiphatic molecules is not always required. If the molecules that form the bilayer coating are chosen such that they are optimized for their role in the bilayer coating, then the order of addition of the two components of the bilayer is not detrimental to the success of the formation of the bilayer coating. For example, if the surface binding molecules are chosen such that the reactive moieties of the surface binding molecules have a high affinity for the nanoparticle, and the amphiphatic molecules are chosen such that the hydrophilic groups have a high preference to be facing the environment, then a stable arrangement is to have the surface binding molecules bind to the nanoparticle and the amphiphatic molecules will have their hydrophilic moieties face the environment. The surface binding molecules and the amphiphatic molecules will interact with each other by means of their hydrophobic moieties. In this way, a complete monolayer of surface binding molecules will form on the nanoparticle, which in turn will be coated with a layer of amphiphatic molecules, wherein the surface binding molecules and the amphiphatic molecules are held together by hydrophobic interactions. In some embodiments, the efficiency and rapidity of the formation of the self-assembling bilayer coating is enhanced by optimizing the amounts of each molecule applied and the order of addition of the components of the compositions.

In one embodiment, 15 nm gold nanoparticles were exposed to either dodecanethiol (surface binding molecule) or Tween 20 (amphipathic molecule). In either case, the compositions were not stable to 1M aqueous NaCl. In another embodiment, uncoated 15 nm gold nanoparticles were also found not to be stable to 1M aqueous NaCl. However, if solutions of dodecanethiol in ethanol and Tween 20 in ethanol were premixed in mostly water and then applied to the 15 nm gold nanoparticles, the coated nanoparticles were stable in 1M aqueous NaCl.

In some embodiments, the solutions of the bilayer coated nanoparticles become hazy indicating micellar or liposome formation if the surface binding molecules are present in high concentration, or the ratio of the concentration of the surface binding molecules to the concentration of the amphipathic molecules is large, or if the amphipathic molecules are applied first to the nanoparticle in high concentrations. However, after both components (i.e. surface binding molecules and amphipathic molecules) are administered in non-limiting amounts, the nanoparticles, such as, for example, 15 nm gold nanoparticles, are stabilized against aggregation in 1 M aqueous NaCl even though the solution was hazy. In some embodiments where hazy solutions are formed, the solutions become clear after some time, such as, for example, after about 1 hour, about 2 hours, about 5 hours, about 10 hours, about 1 day, about 2 days, about 3 days, or after about more than 3 days. The clear solutions that are obtained from the hazy compositions include bilayer coated nanoparticles and the bilayer coated nanoparticles remain stable to 1 M aqueous NaCl. In some embodiments, a low energy state exists wherein the surface binding molecules bind to the nanoparticles through the reactive moieties and interact with amphipathic molecules through the hydrophobic moieties, and the hydrophilic moieties of the amphipathic molecules face the hydrophilic environment. For example, in one embodiment, when 15 nm gold particles are mixed with dodecanethiol and Tween 20 in a hydrophilic environment, a low energy state exists wherein the dodecanethiol is bound to the surface of the gold nanoparticles, forming a complete monolayer, and a layer of Tween 20 coats the dodecanethiol-coated gold. The layer of dodecanethiol and the layer of Tween 20 are held together by hydrophobic interactions. The water soluble ethylene glycols of the Tween 20 molecules face the water environment that surrounds the bilayer coated nanoparticle.

Aggregation of nanoparticles or coated nanoparticles can be a problem when nanoparticles or coated nanoparticles are purified by centrifugation. For example, 5-40 nm gold nanoparticles coated with proteins or polymers are usually purified by centrifugation. After several repeated centrifugations and resuspensions in fresh solvent, the particles typically exhibit increasing aggregation and lead to the formation of a hard pellet or deposit on the walls of the centrifuge tube that cannot be resolubilized, resulting in loss of nanoparticles. The compositions provided herein do not lead to aggregation of nanoparticles. Bilayer coated nanoparticles, as provided herein, do not readily lead to aggregation of the nanoparticles. For example, coating 15 nm gold nanoparticles with a bilayer formed from dodecane thiol and Tween 20 produces bilayer coated nanoparticles that can be purified by multiple centrifugations without loss due to aggregation.

Solvents play an important role in efficiently promoting the desired bilayer coatings on nanoparticles as provided herein. The use of water as the solvent in the formation of the compositions provided herein sometimes requires reduced concentrations of the surface binding molecules and/or amphipathic molecules for solubility reasons and also to avoid forming stable micelles, bilayer and multilayer liposomes that would hinder coating of the surface with a bilayer of molecules. Use of polar and water miscible solvent such as, for example, alcohols (such as, but not limited to, ethanol, methanol, and isopropanol), dimethylformamide, dimethylformamide, dimethysulfoxide, tetrohydrofuran, acetonitrile, and acetone, permit and promote the interaction of the surface binding molecules and the amphipathic molecules to form bilayer coatings at concentrations higher than their aqueous CMC, such as, for example, 1 to 1000 times above their aqueous CMC.

In some embodiments, prior to forming the bilayer coating on nanoparticles a solution is prepared by premixing surface binding molecules and amphipathic molecules in a water miscible solvent that solubilizes both the surface binding molecules and the amphipathic molecules in approximately a one-to-one ratio. In some embodiments, the surface binding molecules and the amphipathic molecules form an intermediate complex in the premixed solution wherein the hydrophobic moieties of the two types of molecules interact through hydrophobic interactions. When the premixed solution is mixed with nanoparticles a bilayer coating forms on the nanoparticle, wherein the surface binding molecules bind to the nanoparticle by means of the reactive moieties and the hydrophobic moieties of the surface binding molecules interact with the amphipathic molecules by means of hydrophobic interactions. Thus surface binding molecules and amphipathic self-assemble into a bilayer coating on the nanoparticle.

In some embodiments, the molecules and methods described herein may be used to prepare nanoparticles with interesting properties. For example, small nanoparticles (less than about 20 nm) can have properties such as, but not limited to, supermagnetism, fluorescence with high quantum yields (>80%), and depressed melting points. These properties make nanoparticles useful as, but not limited to, stains for analyzing biological samples by electron and optical microscopies, as catalysts for the synthesis of carbon nanotubes and inorganic nanowires, as ultrafine magnetic particulates for information storage and as MRI contrast agents. The smaller that the nanoparticle size is, there is a greater percentage of the total number of atoms in the nanoparticle that are interfacial. For example, a 1.3 nm gold nanoparticle has 88% of its atoms on the surface, whereas 10 nm gold nanoparticle has 11.5% of its atoms on the surface (Love, J. C., Estroff, L. A., Kriebel, J. K., Nuzzo, R. G., Whitesides, G. M. *Chem Rev.* 2005, 105, 1103-1169, herein incorporated by reference). The electronic and chemical states of the atoms in nanoparticles influence the chemical, electronic, and optical properties of the nanoparticle. In some cases, special conditions and/or precautions are required to prevent oxidation, nucleation or aggregation of nanoparticles in the solutions in which they are formed. The preparation of some nanoparticles and/or isolation of the nanoparticles may not be possible using existing methods known to those skilled in the art. The instability of some nanoparticles under the reaction conditions in which they are formed and/or isolated requires alternative conditions for their formation and/or isolation.

In one embodiment, surface binding molecules and amphipathic molecules disclosed herein can be used to in situ coat surfaces as they are formed. For example, in some embodiments, nanoparticles are formed in the presence of surface binding molecules and amphipathic molecules. As the nanoparticles are formed in the presence of surface binding molecules and amphipathic molecules, the nanoparticles are coated with a bilayer of molecules giving the nanoparticles immediate protection and a new environmental property that is governed by the properties of the hydrophilic moieties of the amphiphatic molecules that included in the bilayer coating. This approach can also be used to moderate the formation of the surface, control the growth rate and ultimate size or thickness of the underlying surface. For example, the size and growth rate of nanoparticles that are formed from the reduction of metal ions can be controlled by carrying out the reduction of the metal ions in the presence of surface binding molecules and amphiphatic molecules. In some embodiments, nanoparticles are formed from the reduction of metal ions in the presence of surface binding molecules and amphiphatic molecules which coat the nanoparticle as it is formed with a bilayer of molecules and prevent the formation of large particles. In some other embodiments, nanoparticles are formed from the reduction of metal ions in the presence of surface binding molecules and amphiphatic molecules, which coat the nanoparticle as it is formed with a bilayer of molecules and favor the formation of large particles. In some embodiments, nanoparticles are formed from the reduction of metal ions in the presence of surface binding molecules and amphiphatic molecules, which coat the nanoparticle as it is formed with a bilayer of molecules and produce a composition of bilayer coated nanoparticles that have a narrow particle size distribution.

In one embodiment, dodecane thiol and Tween 20 are mixed together and added to a solution that includes $HAuCl_4$ and $NaBH_4$. Under the reducing conditions, gold nanoparticles are formed and coated with a dodecanethiol-Tween 20 bilayer, as discussed herein. Adjusting the concentration(s) of the surface binding molecule(s) and the concentration(s) of the amphiphatic molecule(s) with respect to the gold atoms has an effect on the final gold particle size. This is a convenient way to form functionalized nanoparticles because the synthesis and coating is combined into one step. As discussed herein, various mixtures of surface binding molecules and amphiphatic molecules may be used to produce particles of varying sizes and properties.

In some embodiments, the compositions and methods provided herein may be used to prepare concentrated solutions of larger nanoparticles. For example, larger nanoparticles are usually prepared by reducing metal ions or salts with weak reducing agents to provide dilute solutions of the nanoparticles. For example, gold nanoparticles with a diameter of about 3 nm up to about 100 nm are usually prepared by reducing $HAuCl_4$ with weak reducing agents to provide dilute solutions of the gold nanoparticles. For example, gold nanoparticles with a diameter of about 3 nm up to about 100 nm are usually formed by reducing a 0.01% aqueous solution of $HAuCl_4$ with the weak reducing agent sodium citrate at elevated temperatures, such as, for example, at the boiling temperature of the solution. Under these conditions, gold nanoparticle solutions are prepared that are quite dilute. For example, in one embodiment, reducing a solution of 0.01% aqueous $HAuCl_4$ with sodium citrate provides a resultant solution that includes gold nanoparticles with a diameter of about 40 nm at a concentration of about $2 \times 10^{-10}$M. Under these conditions, raising the gold concentration significantly higher typically results in an insoluble precipitate of gold. This is a problem for the production of large quantities of metal nanoparticles because the nanoparticle solutions prepared by this method are dilute and require time and effort to concentrate the solutions of the nanoparticles, which is not always successful. However, by using the molecules and methods disclosed herein, concentrated, stable nanoparticle solutions can be prepared. For example, in one embodiment, using the methods and molecules provided herein it is possible to prepare gold nanoparticle solutions that are more concentrated than solutions prepared not using the methods and molecules disclosed herein. In one embodiment, gold nanoparticle solutions with up to greater than 30-fold increase in concentration are prepared, as compared to standard methods known in the art. For example, in one embodiment, reducing $HAuCl_4$ in the presence of surface binding molecules and amphiphatic molecules produces a solution of coated gold nanoparticles, wherein the gold nanoparticles have a diameter of about 15 nm, that is more concentrated than solutions of 15 nm gold nanoparticles that are prepared using methods known in the art in the absence of surface binding molecules and amphiphatic molecules. In another embodiment, reducing $HAuCl_4$ in the presence of surface binding molecules and amphiphatic molecules produces a solution of coated gold nanoparticles, wherein the gold nanoparticles have a diameter of about 40 nm, that is more concentrated than solutions of 40 nm gold nanoparticles that are prepared using methods known in the art in the absence of surface binding molecules and amphiphatic molecules.

In some embodiments, the multilayers may be formed on nanoparticles using the methods described herein. In some embodiments, the nanoparticles are coated with a monolayer of surface binding molecules. The monolayer coated nanoparticle now presents a new surface, i.e. the hydrophobic moieties of the surface binding molecules that face the environments, which can be coated using the methods described herein. In another embodiment, the bilayer coated nanoparticles provided herein are coated with additional layers of molecules as described herein. In one embodiment, the bilayer coated nanoparticles provided herein are treated with additional surface binding molecules that react with the environmental groups that are present on the surface of the bilayer coated nanoparticles. The reaction or exposure of additional surface binding molecules with the bilayer coated nanoparticles would then provide a nanoparticle coated with three layers of molecules. In some other embodiments, the nanoparticle coated with three layers of molecules is treated with additional amphiphatic molecules that interact with the third layer by hydrophobic interactions. This process can be repeated to provide nanoparticles that are coated with multiple layers of molecules.

Uses of Coated Nanoparticles

Nanoparticles and coated nanoparticles have a variety of uses, such as those disclosed in: U.S. Pat. No. 6,818,199; U.S. Pat. No. 6,645,464; U.S. Pat. No. 6,670,113; U.S. Pat. No. 6,521,773; U.S. Pat. No. 6,534,039, U.S. Pat. No. 6,369,206; U.S. Pat. No. 6,121,425; U.S. Pat. No. 5,443,813; U.S. Pat. No. 5,521,289; U.S. Pat. No. 5,690,903; U.S. Pat. No. 5,360,895; U.S. Pat. No. 6,955,639; Love, J. C., Estroff, L. A.; Kriebel, J. K., Nuzzo, R. G., Whitesides, G. M. Chem. Rev. 2005, 105, 1103-1169; Ulman, A. Chem. Rev. 1996, 96, 1533-1554; Hoeben, F. J. M., Jonkhejim, P, Meijer, E. W., Schenning, A. P. H. J. Chem. Rev. 2005, 105, 1491-1546; Daniel M, Didier, A. Chem. Rev. 2004, 104, 293-346; Alivisatos, A. P., Gu, W., Larabell, C. Annu. Rev. Biomed. Eng. 2005, 7:55-76; Waggoner, A. Current Opinion in Chemical Biology, 2006, 10:62-66; all of which are herein incorporated by reference.

Compositions provided herein may find use in a variety of contexts. The modular design of the compositions provided herein allows for a rapid and straightforward preparation of coated nanoparticles. By proper choice of surface binding groups, which will bind to the surface to be coated, and amphiphatic molecules, which will associate with the surface binding molecules through the hydrophobic moieties and present a desirable group to the environment, almost any surface, which includes surfaces of particles and nanoparticles, may be coated. By coating a surface, the properties of the coated material can be modified, tuned, attenuated and/or protected for a given application.

Biological uses of the bilayer coated nanoparticles provided herein include, but are not limited to, immunolabeling, medical imaging, and medical therapy.

In other embodiments, coating nanoparticles with a bilayer of molecules as disclosed herein can passivate surfaces, such as, for example, passivate surface properties of semiconductor nanoparticles, can prevent oxidation and attack by environmental chemicals that limit the usefulness of nanoparticles.

Compositions provided herein can be used in a variety of biological applications. In one embodiment, the incorporation of biocompatible amphiphatic molecules in the bilayer coatings can provide nanoparticles that are tolerated in vitro and/or in vivo, with reduced toxicity. For example, in one embodiment, incorporation of amphiphatic molecules that include a hydrophobic moiety, such as, for example, dodecyl, and a hydrophilic moiety, such as, for example, polyethylene glycol moieties, polyvinylpyrrolidinone moieties, and/or sugar moieties, can provide bilayer coated nanoparticles that are biocompatible with reduced toxicity. In one embodiment, 15 nm gold nanoparticles were coated with dodecane thiol as the surface binding molecules, and Tween 20 as the amphiphatic molecules, and injected intravenously into mice at a dose of about 2.2 g Au/kg. The injected particles did not show any apparent acute or long term toxicity.

Fluorescent quantum dots are small nanoparticles of inorganic metals that are used in biology (see, for example, Giepmans B N, Adams S R, Ellisman M H, Tsien R Y. "The fluorescent toolbox for assessing protein location and function." *Science*. 2006 Apr. 14; 312(5771):217-24.; Weng J, Ren J. "Luminescent quantum dots: a very attractive and promising tool in biomedicine." *Curr Med Chem.* 2006; 13(8):897-909.; Mulder W J, Strijkers G J, van Tilborg G A, Griffioen A W, Nicolay K. "Lipid-based nanoparticles for contrast-enhanced MRI and molecular imaging." *NMR Biomed.* 2006 February; 19(1):142-64.; Waggoner A. "Fluorescent labels for proteomics and genomics." *Curr Opin Chem Biol.* 2006 February; 10(1):62-6.; herein incorporated by reference).

Fluorescent quantum dots are small nanocrystals (about 1 nm up to about 10 nm) of inorganic semiconductor materials in which electronic excitations (electron-hole pairs, or excitons) are confined. Fluorescent quantum dots possess several properties that make them very attractive as fluorescent probes for in vivo biological labeling and single-molecule experiments, such as, for example: (i) they have precise emission color tunability by size due to quantum confinement effects; (ii) fluorescent quantum dots are very photostable and emit many more photons per particle compared to dye molecules; (iii) fluorescent quantum dots have a wide absorption band and very narrow and symmetric emission band. Therefore, many color probes can be simultaneously excited by a single narrow-band excitation source, and distinguished in a single exposure. Probes can be made in the near infrared (NIR) region of the spectrum, where auto-fluorescence is considerably reduced and no good dyes exist. (iv) The nanocrystal fluorescence lifetime is in the tens of nanosecond range and therefore allows for discriminating against background by time gated detection; (v) fluorescent quantum dots can be detected both by fluorescence and by an electron beam and therefore can be used to image the same sample by both light and electron microscopy.

In one embodiment, the methods provided herein may be used to coat fluorescent quantum dots. Fluorescent quantum dots have a variety of uses, especially in biological uses. Fluorescent quantum dots are very sensitive to the environment they are in and lose their fluorescent properties when exposed to water. There have been attempts to passivate the surface of fluorescent quantum dots or exclude water when they are used in biological aqueous environments. One attempt that is in current use is to adsorb large polymers onto the surface of the fluorescent quantum dots. Adsorbing large polymers onto the fluorescent quantum dots protects the fluorescent quantum dots for a limited period of time. By coating fluorescent quantum dots with the bilayer coatings provided herein, it is possible to passivate the surface of the fluorescent quantum dots and protect the fluorescent quantum dots from the environment, such as, for example, exposure to aqueous environments. Coating of fluorescent quantum dots with the bilayer coatings provided herein also renders the bilayer coated fluorescent quantum dots biocompatible and therefore provides more robust compositions for use in biological environments. The bilayer coatings provided herein provide a simple solution to optimizing the properties of fluorescent quantum dots for compatibility in biological environments, which does not rely on the use of high molecular weight polymers and proteins.

Atoms with high atom numbers (Z numbers) are useful in medicine, such as, for example, imaging applications. Atoms with high atom numbers, are those that have a Z number of greater than about 20. Atoms with high atomic numbers are able to absorb radiation, such as, but not limited to, X-ray radiation, infrared radiation (including, but not limited to near infrared radiation and far infrared radiation), microwave radiation, ultrasound radiation, radiofrequencies, visible electromagnetic radiation, and/or ultraviolet radiation. The ability of atoms with high atomic numbers to absorb radiation makes them useful as agents in medical imaging applications, such as, for example, X-ray imaging, X-ray and electron microscopic detection, positron emission tomography (PET), single photon emission computed tomography (SPECT), magnetic resonance imaging, and fluorescent imaging. Using the methods provided herein, nanoparticles that include a metal with a high atomic number (Z) may be coated with a bilayer of molecules to provide a biocompatible bilayer-coated nanoparticle that has reduced toxicity and may be used in medical imaging applications. In some embodiments, use of the bilayer coated compositions provided herein provides a method for safely using a larger amount/dose of a metal in in vivo and/or in vitro medical imaging applications. In some embodiments, use of the compositions provided herein allow larger amounts of contrast agents to be administered in medical imaging applications, which then provides sharper and/or more detailed images to be obtained.

X-ray imaging typically uses iodine agents. The use of iodine has shortcomings such as, for example, its low molecular weight (~800 Da), and rapid exit from the blood vasculature, which severely limits imaging time. Injection of iodine solutions into subjects cannot be done rapidly or into small blood vessels due to its high viscosity. Iodine is toxic at some level and can elicit kidney damage and kidney failure in some patients, and allergic reactions in others, sometimes resulting in anaphylactic shock or death. Attempts to target iodine to specific tissues for imaging by incorporating iodine into antibodies or peptides or other molecules have been problematic because the concentration of iodine delivered/incorporated is not high enough for detailed visualization. Nanoparticles that include an element with a high atomic number (Z) are useful for absorbing X-ray radiation, such as, in X-ray imaging.

However, uncoated nanoparticles that include an element with a high atomic number can be toxic. The coating on nanoparticles that include an element with a high atomic number controls to a large extent the toxicity, biodistribution, clearance and in vivo and in vitro use. Using the methods and molecules disclosed herein, bilayer coated nanoparticles that include an element with a high atomic number are produced that are not toxic at useful levels, are biocompatible, and can be used in X-ray imaging. In one embodiment, bilayer coated 15 nm gold nanoparticles as disclosed herein could be injected into mice with an $LD_{50}$ of >2.4 g Au/kg, and at a completely tolerated dose achieve 6,000 Hounsfield Units (HU) (x-ray radiodensity) in their blood vessels after about 3 hours. The high resolution imaging of the blood vasculature in a live animal by microCT was possible, with visualized vessels being observed as small as 20 microns in diameter. Previously, X-ray radiodensity values in the blood of live animals were observed as high as 900 HU. For example, iodine agents and iodine in liposomes have shown maximum values of $\leqq 900$ HU in the blood of live animals, and bismuth nanoparticles have been reported to show X-ray radiodensity values of about 600 HU in the blood of live animals (Mukundan S Jr, Ghaghada K B, Badea C T, Kao C Y, Hedlund L W, Provenzale J M, Johnson G A, Chen E, Bellamkonda R V, Annapragada A. A liposomal nanoscale contrast agent for preclinical CT in mice, *AJR Am J Roentgenol*. 2006 February; 186(2):300-7, Rabin O, Manuel Perez J, Grimm J, Wojtkiewicz G, Weissleder R. An X-ray computed tomography imaging agent based on long-circulating bismuth sulphide nanoparticles. *Nat Mater.* 2006; 5(2):118-22).

Bilayer coated nanoparticles provided herein, such as, for example, bilayer coated nanoparticles with a diameter greater than about 5 nm, can be kept out of the kidneys and also avoid early liver clearance in order to maximize circulation in the blood. For example, administration of 15 nm gold nanoparticles coated with a bilayer formed from dodecanethiol and Tween 20 to mice resulted in a blood half-life of about 2 hours. By modifying the size of the nanoparticle and the bilayer coating, the composition can be optimized for a desired application. This is ideal for extended vascular imaging, such as is required by most microCT units. The bilayer coating on the nanoparticles provided herein also keeps the nanoparticles circulating long enough in the blood to enhance passive or active delivery to other sites, for example, to tumors. A further consequence is the potential use for interventional cardiac catheterization. A current problem is that the iodine agents can cause kidney damage or failure, especially in those patients with already compromised renal function, such as many diabetics. Use of bilayer coated nanoparticles disclosed herein can avoid renal toxic effects observed with conventional contrast agents.

The coating methods disclosed also make possible a variety of routes to couple or incorporate targeting molecules or groups for targeted imaging or localization. Nanoparticles are also useful for therapy, since they can deliver a gene, toxic substance, drug, or material that is useful when exposed to radiation of various kinds such as, but not limited to, x-rays, microwaves, radiofrequency, ultrasound, and infrared. Methods of coating nanoparticles with a bilayer of molecules disclosed herein provide a method to make the particles stable, biocompatible with reduced toxicity, and targeted to specific locations. For example, gold nanoparticles can be used to enhance the local radiotherapy dose in tumors.

The dose enhancement of X-rays adjacent to high atomic number (high-Z) may be used to enhance radiotherapy of cancer (Matsudaira, H., Ueno, A. M., and Furuno, I., "Iodine contrast medium sensitizes cultured mammalian cells to x-rays but not to γ rays," *Rad. Res.* 84: 144-148, 1980). Radiation oncologists have also noted tissue necrosis around metal implants following therapeutic irradiation with X-rays (Castillo, M H, Button, T M, Doerr, R, Homs, M I, Pruett, C W, Pearce, J I, "Effects of radiotherapy on mandibular reconstruction plates," *Am. J. Surg.* 156, 261 (1988)). Das and coworkers made careful measurements of the dose enhancement factor at low-Z/high-Z interfaces irradiated by X-rays (Das, I J, Chopra, K L, "Backscatter dose perturbation in kilovoltage photon beams at high atomic number interfaces," *Med. Phys.* 22: 767-773, 1995). Experimental X-ray dose enhancement adjacent to bulk metallic gold was reported by Regulla and coworkers (Regulla, D F, Hieber, L B, and Seidenbusch, M, "Physical and biological interface dose effects in tissue due to X-ray-induced release of secondary radiation from metallic gold surfaces," *Rad. Res.* 150, 92 (1998)). A solid state detector was placed next to a thin (150 μm) gold foil and a dose enhancement factor of more than 100 with a range of 10 μm was found in the range of 40 to 120 kV tube potential. Cells were then placed in close proximity (2 μm) to the gold surface. In a clonogenic assay, 80 keV X-rays caused 80% cell killing at 0.2 Gy, which was a factor of 50 over the control without gold.

U.S. Pat. No. 6,001,054 to Regulla and Eckhard discloses a method for treating a site in a human body to inhibit abnormal proliferation of tissue at the site by introducing a metal surface at the site and then directing ionizing irradiation to the metal surface to obtain locally enhanced radiation therapy. The dose enhancement from the metal was observed within only about 100 microns of the stent. The stent would not be practical for a variety of applications, especially for areas that are not readily accessible.

The use of gold particles with a diameter of about 1.5-3.0 micrometers (1% by weight) in a stirred suspension with living cells during irradiation with 100-240 kVp X-rays produced a dose enhancement factor of about 1.54 (Herold, D M, Das, I J, Stobbe, C C, Iyer, R V, and Chapman, J D, "Gold microspheres: a selective technique for producing biologically effective dose enhancement," *Int. J. Rad. Biol.* 76: 1357-1364, 2000). Injection of the gold particles (1.5-3 micron in diameter, 1% gold suspension) directly into a growing tumor at 3 sites followed by irradiation (8 Gy, 200 kVp) was also disclosed by Herold et al. It was disclosed that the gold particles did not diffuse into the tumor but remained at the three sites of injection.

Nanoparticles that include a heavy metal can be coated with bilayer of molecules as disclosed herein. If the surface of the bilayer coating is conjugated to a suitable molecule, peptide, protein, antibody, or nucleic acid, the bilayer coated nanoparticle can be targeted and/or directed to tumors. The nanoparticles will be in the close vicinity of the tumor cells and thus be able to direct effective doses of radiation to the tumor cells.

In some embodiments, nanoparticles that include radioisotopes of heavy metal(s) can be coated with bilayer of molecules as disclosed herein. If the surface of the bilayer coating is conjugated to a suitable molecule, peptide, protein, antibody, or nucleic acid, the bilayer coated nanoparticle can be targeted and/or directed to tumors. The nanoparticles that include radioisotopes of heavy metal(s) will be in the close vicinity of the tumor cells and thus be able to emit radiation, such as, beta radiation, to the tumor.

In some embodiments, if the nanoparticles are absorbing or emitting radiation, the surface binding molecules and the amphiphatic molecules that form the bilayer coating on the nanoparticles may be chosen such that they do not appreciable diminish the amount or radiation that is absorbed or emitted by the nanoparticles.

The coating can be used to make nanoparticles useful for imaging by including detectable materials, such as high atomic number elements for x-ray and electron microscopic detection, including gold, tungsten, bismuth, iridium, platinum, even lead and osmium, or radioactive elements useful for Positron Emission Tomography (PET) and Single Photon Emission Computed Tomography (SPECT), magnetic or paramagnetic materials for Magnetic Resonance Imaging, or fluorescent containing materials, such as fluorescein, cyanine dyes, semiconductor crystals, and quantum dots, for fluorescent imaging.

Magnetic nanoparticles have many applications, including use in recording media, biosensors, magnetic ferrofluids, magnetic inks, cell separations with magnetic beads, and as magnetic resonance imaging (MRI) contrast agents (as well as those uses in U.S. Pat. No. 6,521,773; U.S. Pat. No. 6,534,039; both are herein incorporated by reference). The methods described herein can be used to produce magnetic materials and nanoparticles that have desirable properties that are difficult to obtain by using methods known in the art. For example, magnetic nanoparticles coated with the bilayer coating provided herein stabilize and preserve the magnetic properties of the magnetic nanoparticle. Due to oxidation or other chemical changes in solution, it is a problem to retain high relaxivity, magnetic susceptibility, and specific absorption ratio of magnetic nanoparticles in solution. By using the disclosed coating methods, it has been possible to retain initial magnetic properties of nanoparticles in solution for more than 3 months, even when stored at room temperature.

Magnetic nanoparticles can be prepared from the magnetic elements or elements that are capable of becoming magnetic (such as, but not limited to, iron, cobalt, nickel, gadolium, chromium, manganese). The magnetic nanoparticles can be prepared as mixtures of metals, as metal oxides, as alloys, or other combinations and forms known to those of skill in the art. Some common magnetic nanoparticles include, but are not limited to, hematite, $Fe_2O_3$, maghemite, gamma-$Fe_2O_3$ and magnetite, $Fe_3O_4$, alloys, such as, for example, alnico (aluminum, nickel, cobalt), mixed oxide materials with octahedral $Fe^{3+}$ ions such as, for example, the spinels $BaFe_{12}O_{19}$, and $Ba_2Mn_2Fe_{12}O_{22}$, gadolinium complexed with DTPA (diethylenetriamine pentaacetic acid), or those disclosed in U.S. Pat. No. 6,521,773; U.S. Pat. No. 6,534,039.

For oxide containing magnetic nanoparticles, small molecules with a negative charge, or those containing oxygen, as well as silanes, are a few of the possible surface binding molecules that are contemplated in the monolayer that coats the nanoparticle. The surface binding molecules also include a hydrophobic region that can interact with the hydrophobic region of the amphiphatic molecules. The amphiphatic molecules will include a hydrophilic moiety that will confer water solubility to the bilayer coated magnetic nanoparticle. As discussed, the hydrophobic region that is formed between the layer of the surface binding molecules and the layer of the amphiphatic molecules will protect the magnetic nanoparticle from the harmful effects of water and oxygen, such as, oxidation.

The following embodiment is discussed by way of example; modifications can be made to provide alternative embodiments using the methods disclosed herein. In one embodiment, iron oxide nanoparticles containing magnetite ($Fe_3O_4$) can be formed by mixing an aqueous solution of a $Fe^{3+}$ salt with a $Fe^{2+}$ salt in the molar ration of 2:1 and raising the pH. The magnetite nanoparticles will precipitate. In one embodiment, the surface binding molecules and amphiphatic molecules that will form the bilayer coating are premixed and then added to the magnetic nanoparticle. In one embodiment, the surface binding molecules are selected from among fatty acids and the amphiphatic molecules are selected from among surfactants. In one embodiment, the magnetite nanoparticles are treated with a premixed solution of oleic acid and Tween 20. In this embodiment, the magnetite nanoparticles will be coated with a bilayer of molecules, wherein the oleic acid forms a complete layer on the magnetite nanoparticles and the Tween 20 molecules form a layer on the oleic acid layer, wherein the two layers are held together by hydrophobic interactions. The Tween 20 molecules present a shell of ethylene glycol moieties to the environment, which make the bilayer coated nanoparticle water soluble and biocompatible. If desired, the double bonds in the oleic acid may be crosslinked with, for example, osmium tetroxide or permanganate, or the double bonds may be polymerized for increased stability, if desired. In other embodiments, a combination of surface binding molecules and/or amphiphatic molecules may be used to provide a bilayer coating for the magnetic nanoparticles contemplated herein.

The toxicity of the magnetic nanoparticles in magnetic resonance imaging (MRI) applications is an important consideration and can limit the utility of the magnetic nanoparticle agents. Magnetic nanoparticles that are prepared using art methods typically have $LD_{50}$ values of about 1 mg Fe/kg up to about 500 mg Fe/kg (Pouliquen D, Perdrisot R, Ermias A, Akoka S, Jallet P, Le Jeune J J "Superparamagnetic iron oxide nanoparticles as a liver MRI contrast agent: contribution of microencapsulation to improved biodistribution." *Magn Reson Imaging.* 1989 November-December; 7(6):619-27; Matthias Taupitz, "A new Contrast medium for MRI on the basis OF Citrate stabilized Magnetic Nanoparticles" Digital thesis, F U Berlin, 2005; Xia Z, Wang G, Tao K, Li J, Tian Y "Preparation and acute toxicology of nano-magnetic ferrofluid." *J Huazhong Univ Sci Technolog Med Sci.* 2005; 25(1):59-61). Typical recommended doses of magnetic nanoparticle agents are usually 1/10 of the $LD_{50}$ dose. Some common magnetic nanoparticles that are currently in medical use include, for example, AMI-25, which has a $LD_{50}$ of about 1.3 mg Fe/kg (AMI-25 is also know as Ferumoxide and is sold under the tradenames of Endorem® by Guerbet and Ferridex I. V.® by Berlex Laboriteries, 80-150 nm standard superparamagnetic iron oxide particle (SSPIO));

SHU 555A, which has a $LD_{50}$ of about 0.6 mg Fe/kg (SHU 555A is sold under the tradename of Resovist® by Schering and include 62 nm SSPIO);

AMI 227, which has a $LD_{50}$ of about 2.2 mg Fe/kg (AMI 227 is sold under the tradename of Sinerem® by Guerbet, and Combidex® by Advanced Magnetics, and includes 20-40 nm ultrasmall superparamagnetic iron oxide [USPIO] particles);

NC100L50, which has a $LD_{50}$ of about 5.6 mg Fe/kg (NC100L50 is sold under the tradename Clariscan® by Nycomed, and includes 20 nm USPIO) (Wang Y X, Hussain S M, Krestin G P. "Superparamagnetic iron oxide contrast agents: physicochemical characteristics and applications in MR imaging." *Eur Radiol.* 2001; 11(11):2319-31). Note: In these aforementioned materials, the LD50 has been calculated assuming the recommended dose is 1/10 of the LD50.

Provided herein are bilayer coated magnetic nanoparticles, such as iron nanoparticle, that have an acute $LD_{50}$ of greater than about 2000 mg Fe/Kg (intravenous injection into mice). These magnetic nanoparticles can be used as vascular contrast agents, or functionalized to change the biodistribution in order to target specific organs such as, but not limited to, the liver, kidneys, tumors, lymph nodes, or other targets. The bilayer coated magnetic nanoparticles may also be used to load living cells by protein transduction domain incorporation, receptor mediated endocytosis, electroporation, or other means. Such loaded cells may be used for MRI tracking. The magnetic nanoparticles may be loaded into liposomes, cells, or erythrocyte hosts along with other drugs or substances to magnetically deliver the materials at a specific site which may optionally later disrupt and release the contents.

The bilayer coated magnetic nanoparticles that are provided herein have a smaller shell than magnetic nanoparticles that are coated with high molecular weight polymers, such as, but not limited to, dextrans. The bilayer coated magnetic nanoparticles provided herein are smaller than existing magnetic nanoparticle compositions and permit better penetration into tumors and entrance into organs, such as, for example, kidneys for kidney imaging.

Magnetic nanoparticles have been used to separate cells when incorporated into micron-sized beads with, for example, an antibody coating that then bind to a specific cell type and can be isolated by a bar magnet (see, for example, the Dynal® product sold by Invitrogen, based in Carlsbad, Calif., www.invitrogen.com/dynal). When single magnetic nanoparticles are used, the force in a field gradient is very low, and can be overcome by Brownian motion and thermal energy, such that little or no accumulation is achieved with reasonable magnets. This is why many concerted interacting superparamagnetic particles are immobilized in micro-sized beads to achieve clearance from a solution. However, with a more powerful magnet (e.g., 0.3 Tesla), the field gradient at the pole piece edge has been discovered to be strong enough to pull superparamagnetic nanoparticles onto an electron microscope grid (compared to no magnetic field). The magnetic nanoparticles may be attached to biomolecules, such as antibodies, proteins, nucleic acid, lipids, carbohydrates, peptides, drugs, organic molecules and other materials. This demonstrates that magnetic nanoparticles can be used separate such labeled molecules via a magnetic field. Not only is this useful for enriching labeled biomolecules for electron microscopy, but can be used to isolate other materials either in solution or from a stream, where a fluid, drop or microfluid is deflected by a magnetic gradient. Individual molecules may also be manipulated to increase exposure to cells, to enhance transfection of magnetic-nucleic acid conjugates, to enhance drug delivery, and even move molecules within cells, such as into the nucleus by magnetic forces.

In some embodiments, the compositions provided herein may be used as drug carriers or delivery systems. Drug delivery is one of the most important problems in disease treatment. Unfortunately, the level of drug that can be safely administered frequently falls below that needed for complete tumor remission. Similarly, most other drugs systemically applied show toxicity limits and side effects before the desired effectiveness on the target tissue is achieved. If the drug could be delivered more specifically, this would greatly aid in drug therapies. The described particles with coatings can be coupled to drugs and directing moieties, such as antibodies, antibody fragments, single chain antibodies, peptides, proteins, cytokines, aptamers, nucleic acids, carbohydrates, lipids, or organic compounds that target the desired tissue or cells to be treated. Additionally, since many drugs are hydrophobic, they may be incorporated into the bilayer hydrophobic interaction domain. By incasing the drug in the structure it can "hide" the drug and reduce systemic toxicity. Another feature of this construct is that the drug can be released more slowly, providing a time-release mechanism for delayed or more even application of the drug over time.

EXAMPLES

The person skilled in the art may further appreciate various aspects and advantages of the present disclosure upon review of the following illustrative and non-limiting examples:

Example 1

Coating a 15 nm Gold Nanoparticle

Colloidal gold nanoparticles with a diameter of about 15 nm were prepared by mixing 100 mL of boiling water with 1 mL of 1% aqueous $HAuCl_4$ and 3 mL of 1% aqueous sodium citrate and heating the mixture for 15 minutes. A red solution developed and analysis by electron microspray indicated that 15 nm gold nanoparticles had formed. Dodecanethiol (the surface binding molecule) was diluted 1:100 in ethanol. The surfactant Tween® 20 (the amphiphatic molecule) was diluted 1:100 in ethanol. 10 microliters of the dodecanethiol solution was mixed with 20 microliters of the Tween® 20 solution followed by the addition of 0.4 mL of the 15 nm gold solution. After 10 minutes, the coated nanoparticles were purified from excess ligands by centrifugation to pellet the gold particles. The supernatant was removed and the gold pellet that was isolated were resuspended in water and the process of centrifugation was repeated 3 times. The coated gold nanoparticles were stable in 1 M NaCl, whereas the uncoated gold nanoparticles aggregated and precipitated in 0.1 M NaCl.

15 nm gold nanoparticles that are coated with adsorbed polyethylene glycol, adsorbed antibodies, adsorbed polyvinylpyrrolidone, or adsorbed polyacrylamide hydrazide showed some aggregation evident upon centrifugation by some fraction of the sample forming an insoluble hard pellet upon centrifugation, particularly after multiple washing steps (where the supernatant is removed and the pellet is redissolved in fresh buffer and recentrifuged). In contrast, the dodecanethiol/Tween® 20 coated nanoparticles showed no aggregation or adhesion of particles or insoluble pellet even after multiple repeated washing cycles. These particles were also unaffected by boiling for 10 minutes or by addition of beta mercaptoethanol at a final concentration of 100 mM.

Example 2

Stabilization of 40 nm Gold Nanoparticles

Large gold particles, with a size greater than about 40 nm, tend to be difficult to stabilize. However, coating of the gold particles with dodecanethiol (surface binding molecule) and Tween® 20 (amphiphatic molecule) resulted in exceptionally well stabilized particles.

Colloidal gold nanoparticles with a diameter of about 40 nm were prepared by citrate reduction of chloroauric acid in boiling water. Dodecanethiol was diluted 1:100 in ethanol. Tween® 20 was diluted 1:100 in ethanol. 10 microliters of the dodecanethiol solution was mixed with 20 microliters of the Tween® 20 solution followed by the addition of 0.4 mL of the 40 nm gold solution, and the mixture was mixed for 10 minutes. The coated gold nanoparticles were purified from excess ligands by centrifugation to pellet the gold particles. The supernatant was removed and the pellet was resuspended in water and the process of centrifugation was repeated 3 times.

The dodecanethiol/Tween® 20 coated gold nanoparticles showed no aggregation or adhesion of particles or insoluble pellet even after multiple repeated washing cycles. Uncoated gold particles aggregated and precipitated in 0.1 M NaCl, whereas the coated gold particles were stable in 1 M NaCl. The coated gold particles were also unaffected by boiling for 10 minutes or by addition of beta mercaptoethanol at a final concentration of 100 mM.

Example 3

Synthesis and Simultaneous Coating of 2 nm Gold Nanoparticle

Dodecanethiol was diluted 1:100 in ethanol. The surfactant Tween® 20 was diluted 1:100 in ethanol. 10 microliters of the dodecanthiol solution was mixed with 80 microliters of the Tween 20 solution. 200 microliters of water was added, followed by 4 microliters of a 25 mg/mL solution of $HAuCl_4$ dissolved in ethanol. After mixing, 4 microliters of a 2 mg/mL solution of $NaBH_4$ solution in ethanol was added. The solution turned brown. 4 microliters of a 1 N aqueous solution of NaOH was added followed by 4 microliters of the borohydride solution resulting in a darker brown solution. After several minutes an additional 8 microliters of the borohydride solution was added. Electron microscopy showed that the gold nanoparticles that were formed had a diameter about 2 nm. The coated gold nanoparticles were stable in 1 M NaCl and stable upon boiling. When centrifuged in a 100,000 molecular weigh cutoff concentrating filter, the particles did not pass through the filter, but remained in the retentate. This indicated a hydrodynamic shell diameter of >5 nm, consistent with the particles being coated with a bilayer that includes dodecanethiol and Tween® 20.

Example 4

Synthesis and Simultaneous Coating of ~15 nm Gold Nanoparticles

5 µL of dodecanethiol was mixed with 5 µL ethanol followed by the addition of 40 µL of Tween® 20 in 40 µL ethanol. 250 µL of deionized water was then added followed by 100 µL of $HAuCl_4$ (25 mg/ml in water solution). After mixing, 50 µL of $NaBH_4$ (2 mg/mL in ethanol) was added and the solution turned dark red. The nanoparticles were purified by centrifugation, where at 15,000×g the particles could be pelleted. The supernatant was removed and replaced with water or buffer, and centrifugation was repeated. This was repeated a third and fourth time to remove materials not bound to the gold particles. Surprisingly, no hard pellets were found (which tend to be common with other coatings, especially after multiple washes), and the pellets dissolved readily in fresh solvent. Alternatively, other samples of the nanoparticles were purified by ultrafiltration either in a stirred pressurized cell or in a centrifugal device containing a membrane. A 100,000 MWCO (molecular weight cutoff) membrane filter was used. Spectral analysis and electron microscopy confirmed the formation of ~15 nm gold nanoparticles. The particles were found to be very stable to multiple centrifugations without coagulation, were stable in 1 M NaCl, were stable at 100° C. and resisted degradation in 100 mM beta-mercaptoethanol.

Example 5

Biocompatibilty of Coated Gold Nanoparticles

Coated gold nanoparticles with a diameter of about 2 nm and about 15 nm were prepared as outlined in Examples 3 and 4. The particles were purified and concentrated by ultrafiltration or centrifugation to a concentration of 83 mg Au/mL, which was measured by graphite furnace atomic absorption. The nanoparticles were suspended in phosphate buffered saline and injected intravenously via tail vein into 12 C3H mice, administering 830 mg Au/kg. The mice did not display any abnormal behaviors and gained weight normally. The mice were observed for over 6 months now without indication of any adverse effects. In another experiment, mice that were injected with 2200 mg/kg of 15 nm coated gold nanoparticles, which were prepared as outlined in Example 1, showed no acute toxicity.

Example 6

X-Ray Imaging of Live Animals Using Coated Gold Nanoparticles 15 nm coated nanoparticles were prepared as outlined in Example 1. 400 mg Au/kg was administered into Balb/C mice by intravenous tail vein injection. Mice were placed in a clinical mammography unit and imaged using x-ray film, using 22 kVp x-rays, 0.8 sec exposure and 16 mAs. The gold enabled blood vessels are observed.

500 mg Au/kg of 15 nm gold nanoparticles prepared by the method of Example 1 were injected intravenously into Balb/C mice and 2048×2048 pixel digital planar images were taken with a Skyscan 1076 microCT unit operating at 41 kVp with no filter. Contrast in the kidneys, bladder, and liver did not perceptibly increase over this time, indicating that the gold particles successfully remained in the blood as a blood pool contrast agent.

Figure 2:
FIG. 2 is an illustrative, non-limiting example of a 9 micron cross-section of the legs and lower abdomen of a live mouse taken 3 hours after the injection of coated 15 nm gold nanoparticles, which were prepared as described in Example 1. The image was obtained using a Skyscan 1076 microCT unit operating at 41 kVp. Bright dots show blood vessels contrasted with the coated gold nanoparticles, some of which have a radiodensity of 6,000 HU.
Figure 3:
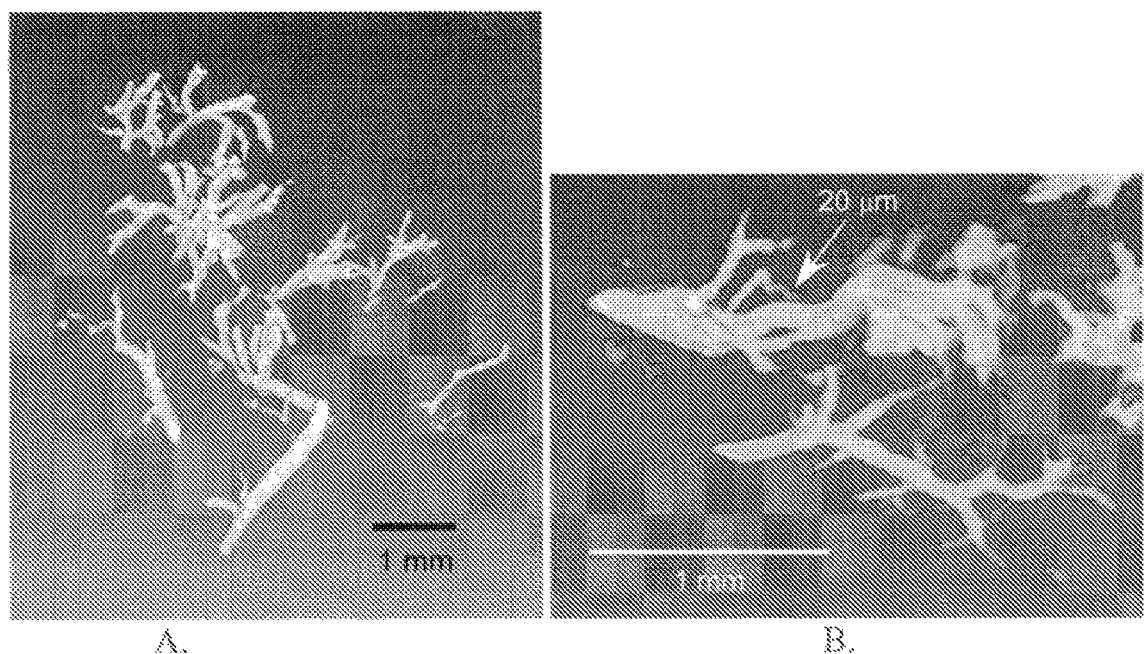
FIG. 3A is an illustrative, non-limiting example of blood vessels imaged in the leg of a live mouse after an intravenous injection of bilayer coated 15 nm gold nanoparticles, which were prepared as described in Example 1. 150-9 μm sections were taken with a Skyscan 1076 microCT unit operating at 41 kVp.
FIG. 3B is an illustrative, non-limiting example of enlargement and rotation of a region depicted in FIG. 3A. showing blood vessels with a diameter of about 20 microns.

A Balb/C mouse was anesthetized with 75 mg pentobarbital/kg (with a boost 3 hours later) and injected with 2000 mg Au/kg in the form of the coated 15 nm particles of Example 1. Several microCT imaging sessions were performed, and blood vessels were very clearly delineated. An extraordinary result was obtained in a scan commenced 3 hours after the gold nanoparticle injection which lasted for an additional 3.5 hours, the mouse being alive the whole time, having been given a boost of anesthetic before imaging. Long imaging times are required with most microCT units due to the low x-ray tube power and high resolution detectors, making the counts per pixel very noisy with short times. A Skyscan 1076 unit was used operating at 41 kVp. Not only were microvessels clearly seen, but the whole vascular network (in the lower abdomen and hindlegs that were imaged) was visualized down to an unprecedented 20 micron vessel size. This resolution has never before been achieved in a live animal. A 9 micron cross section of the leg is shown in FIG. 2, and part of the vascular tree is shown in FIG. 3A, with a smaller region magnified to reveal clear definition of 20 micron diameter vessels (FIG. 3B.).

Example 7

Conjugating Antibody to Bilayer Coated Gold

Colloidal gold particles with a diameter of about 15 nm were prepared by mixing 100 mL of boiling water with 1 mL of 1% aqueous $HAuCl_4$ and 3 mL of 1% aqueous sodium citrate. The solution was heated for 15 minutes. In a separate vessel was added: 1) 43 microliters of a solution of 1 part dodecanethiol and 100 parts ethanol; 2) 67 microliters of a solution of 1 part Tween® 20 and 100 parts ethanol; and 3) 28 microliters of a solution of 1 part dodecanaldehyde and 100 parts ethanol. The dodecanthiol/Tween® 20/dodecanaldehyde solution was then added to 9 mL of the 15 nm gold particles solution. The coated particles were purified by centrifuging them at 19,500 rpm in a SS34 rotor for 55 minutes.

The pellet was resuspended in PWB (pyridine wash buffer, 10 mM pyridine, pH 6.0) and transferred to a 1.5 mL microfuge tube and centrifuged 2 times in a tabletop centrifuge at 14,000×g for 15 mins. The last pellet was dissolved in 0.125 mL of PWB followed by the addition of 0.135 mL of mouse IgG (1.4 mg/mL). To the solution was added 5.5 microliters of 5M $NaCNBH_3$ in PWB and the reaction mixture was incubated for 3 hours. Ethanolamine (4.5 microliters of a 3M solution at pH 8.0) was then added to react with the remaining aldehyde functional groups from the dodecanaldehyde molecules. The solution was stirred for an additional 30 minutes. The coated gold nanoparticle-IgG conjugate was then purified by centrifugation 3 times using PWB. The purified pellet was mixed with 0.5 mL of TBS (10 mM Tris buffer, 140 mM NaCl). An immunoblot was prepared by spotting 1 microgram of goat anti-mouse IgG on a nitrocellulose membrane, and allowing it to air dry for 30 minutes. The membrane was blocked with TBS+5% dry milk for 30 minutes and then washed with TBS three times. The gold-antibody conjugate was then applied to the membrane and reacted for 12 minutes, followed by 3 washes with TBS, water, and then air drying. Strong antibody targeting of the gold complex with low or non-existent background reaction was observed.

Example 8

Functionalization of Gold Nanoparticles with Ni-NTA (Nitrilotriacetic Acid) and Binding to His-Tagged Proteins 0.2 mL of the nickel salt of 1,2-Dioleoyl-sn-Glycero-3-[(N-(5-amino-1-carboxypentyl)iminodiacetic acid)succinyl] (DOGS-Ni-NTA) in chloroform was evaporated to dryness with a stream of nitrogen. To this was added 0.2 mL of dodecanethiol and then 0.05 mL of this solution was added to 0.5 mL of tetrahydrofuran (THF) and vortexed.

Colloidal gold with a diameter of about 15 nm was prepared by mixing 100 mL of boiling water with 1 mL of 1% aqueous $HAuCl_4$ and 3 mL of 1% aqueous sodium citrate. The solution was heated for 15 minutes. 4 mL of the gold nanoparticle solution was added to the THF solution, and an additional 15 mL of water added. After mixing, the solution was centrifuged at 15,000×g for 15 minutes, and the soft gold pellet was resuspended in 2 mL of water and centrifuged again. The pellet was resuspended in 1 mL of water.

A dot blot experiment was performed by binding a 6×-Histidine tagged protein, ATF-1 (molecular weight 34 kDa) to a nitrocellulose membrane with a 0.22 micron pore size. 1 microliter of the tagged ATF-1 protein (1 mg/mL) was applied to the membrane and allowed to dry. The membrane was blocked with TBS+5% dry milk for 30 minutes and washed with TBS three times. The gold-Ni-NTA solution was then added to the membrane and incubated for 1 hour, followed by a 2 minute wash in TBS buffer. A spot was formed which showed the red color of the coated gold nanoparticle binding to the his-tagged protein. No background reaction was observed to the milk proteins used for blocking or to non-his tagged proteins, such as bovine serum albumen (BSA).

Example 9

Protection of Gold Surface Indicated by Resistance to Silver and Gold Enhancement The following experiment were performed to demonstrate that bilayer coated nanoparticles show unusual stability to the core nanoparticle in response to silver enhancement reagents/solutions. For example, gold nanoparticles coated by conventional methods in the art can nucleate silver metal deposition on their catalytic surface in the presence silver ions and a reducing agent. The gold particle then grows in size. Coating gold particles with a bilayer of molecules as disclosed herein, strongly inhibits this deposition, indicating that the catalytic gold surface is not readily accessible to the silver ions and reducing agent. The same result was also obtained with a gold enhancement solution.

Figure 4:
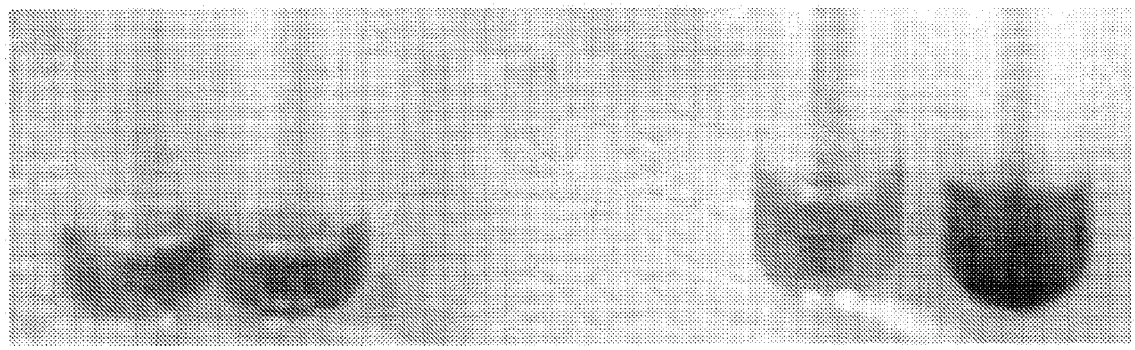
FIG. 4 is an illustrative, non-limiting demonstration of experiments that test the ability or inability of coated gold nanoparticles to undergo silver enhancement. Test tube 1 contains a solution of gold nanoparticles, with a diameter of about 15 nm coated with a bilayer formed from dodecanethiol and Tween 20, as described in Example 1. Test tube 2 contains a solution of gold nanoparticles that are coated with BSA, as described in Example 9. Test tube 3 shows the results after 45 minutes following the addition of LI Silver, which is a silver enhancement solution to the contents of test tube 1. Test tube 4 shows the results after 45 minutes following the addition of LI Silver to the contents of test tube 2. The coated gold nanoparticles that were prepared as described in Example 1 (Test tube 3) did not show any silver deposition/enhancement, whereas the solution containing gold nanoparticles coated with BSA (test tube 4) turned dark black indicating silver deposition.

Coated gold nanoparticles with a diameter of about 15 nm were prepared as described in Example 1 (dodecanethiol/Tween 20-coated gold). In a separate vessel 15 nm gold nanoparticles were prepared by citrate reduction of chloroauric acid and coated with bovine serum albumen (BSA) by adsorption. The citrate reduced gold was mixed with BSA at an appropriate pH and concentration. The coated gold nanoparticles were then purified by centrifugation. A silver enhancement solution which is known to deposit silver on gold particles (LI Silver) was added to both the dodecanethiol/Tween 20-coated coated gold and the BSA-coated gold and incubated for 45 min. The BSA-coated gold turned dark black indicating silver deposition. The dodecanethiol/Tween 20-coated gold of Example 1 did not initiate silver deposition (see FIG. 4).

Figure 5:
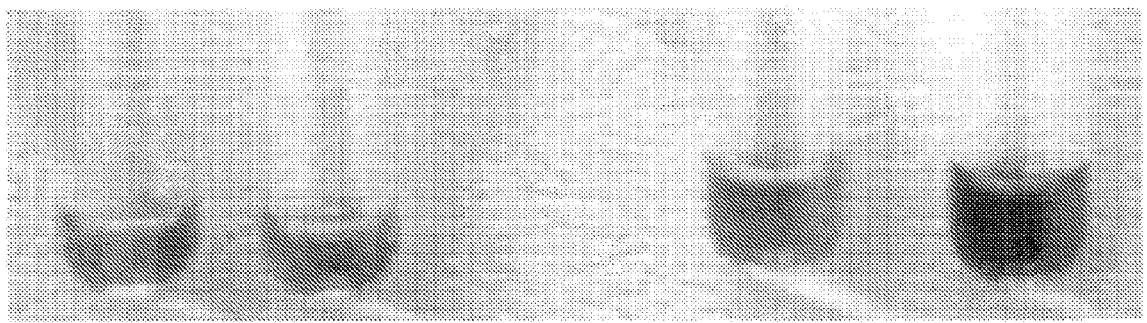
FIG. 5 is an illustrative, non-limiting demonstration of experiments that test the ability or inability of coated gold nanoparticles to undergo gold enhancement. Test tube 1 contains a solution of gold nanoparticles, with a diameter of about 15 nm coated with a bilayer formed from dodecanethiol and Tween 20, as described in Example 1. Test tube 2 contains a solution of gold nanoparticles that are coated with BSA, as described in Example 9. Test tube 3 shows the results after 15 minutes following the addition of GoldEnhance EM, which is a gold enhancement solution, to the contents of test tube 1. Test tube 4 shows the results after 15 minutes following the addition of GoldEnhance EM to the contents of test tube 2. The coated gold nanoparticles that were prepared as described in Example 1 (Test tube 3) did not show any gold deposition/enhancement, whereas the solution containing gold nanoparticles coated with BSA (test tube 4) showed gold deposition.

Gold deposition onto metal nanoparticles is a similar process to the deposition of silver onto metal nanoparticles where the gold surface is catalytic and favors reduction and deposition of gold ions as gold metal in the presence of a reducing agent. When bilayer coated gold (see Example 1) was compared to gold coated by methods known in the art, i.e., adsorption of proteins, such as, for example BSA, the bilayer coated gold was found to resist catalytic deposition, which implies that the shell is impermeable to gold (or silver) ions and the water soluble reducing agents and cannot effectively interact with the gold surface (FIG. 5). This experiment demonstrates the chemical stability achieved by the bilayer coatings disclosed herein.

Example 10

Blood Retention of Coated 15 nm Nanoparticles

Figure 6:
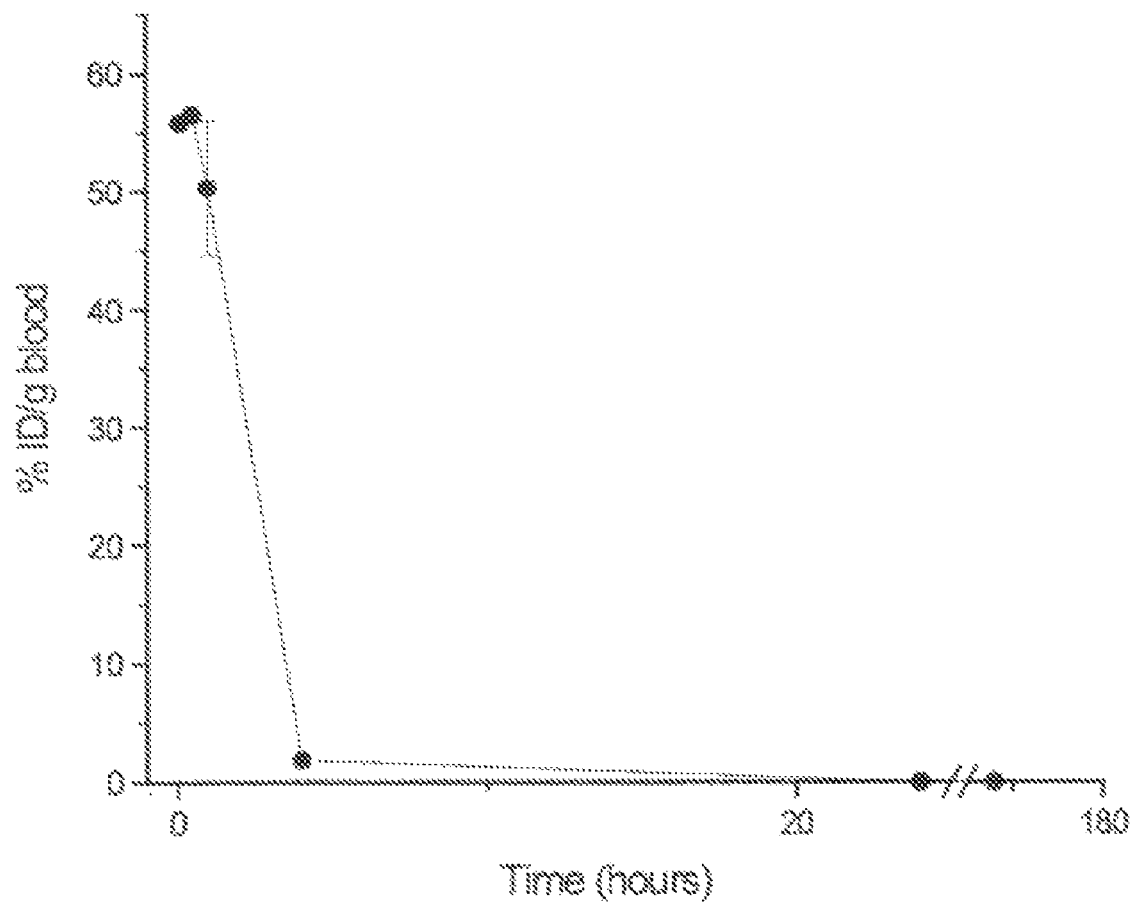
FIG. 6 is an illustrative, non-limiting example of the residence and clearance of bilayer coated 15 nm gold nanoparticles, which were prepared as described in Example 1, from the blood of mice. % ID/g blood=% injected dose per gram of blood.

Coated gold nanoparticles were prepared as described in Example 1 and concentrated such that 4.2 mg Au was intravenously injected via tail vein into each mouse. Three mice were sacrificed after predetermined time periods: 5 minutes, 30 minutes, 1 hour, 4 hours, 1 day and 7 days later. Blood was extracted from the hearts of the mice. The blood was dissolved in aqua regia, triton X-100, and nitric acid and analyzed for gold content by graphite furnace atomic absorption spectroscopy. The results are shown in FIG. 6 and indicate a blood half-life of about 2 hours, with virtually complete clearance after 1 day.

Example 11

Preparation of Coated Magnetic Nanoparticles $FeCl_3$ and $FeCl_2$ in a molar ratio of 2:1 was added to aqueous HCl and formed into superparamagnetic nanoparticles by pH adjustment with ammonium hydroxide, triethylamine, or potassium carbonate. The reaction was heated at 80° C. for 30 minutes. The particles were then coated with a solution that included 1 part oleic acid, 15 parts Tween® 20, and 15 parts water. The iron nanoparticles were then centrifuged at 45,000×g for 45 minutes, rinsed with water, and then centrifuged again. The sample was concentrated using a 50,000 MWCO (molecular weight cutoff) filter.

Example 12

Biocompatibility of Coated Magnetic Nanoparticles

Mice were intravenously injected via the tail vein with the coated magnetic iron nanoparticles that were prepared as described in Example 11. The mice were injected with a dose containing 25 mg Fe. No adverse effects were noted immediately or up to 1 month later.

Example 13

Use of Magnetic Field Gradients to Control Single Magnetic Nanoparticles

Figure 7:
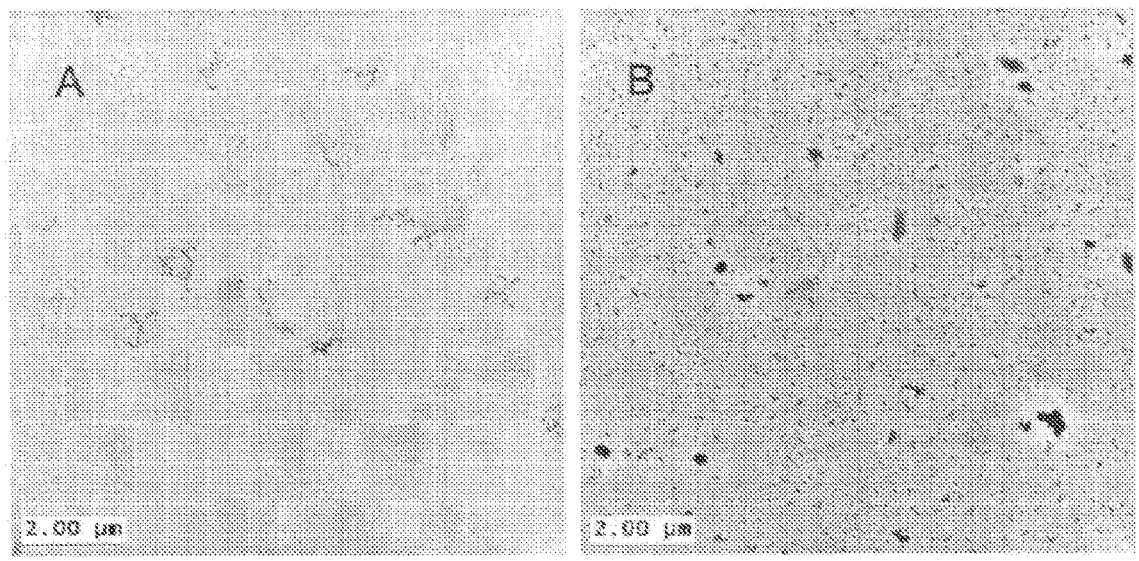
FIG. 7 is an illustrative, non-limiting of electron micrographs showing concentration of magnetic iron nanoparticles, prepared as described in Example 11, by attraction in a magnetic field gradient. The nanoparticle solution was placed on a carbon coated grid for 4 minutes either without exposure (A) or exposure (B) to a magnetic field gradient.

The coated magnetic nanoparticles of Example 11 were diluted to 1 O.D. at 400 nm and a drop applied to a carbon coated electron microscope grid. After 4 minutes, the sample was wicked off with filter paper and washed several times with water. In a parallel experiment, a grid with the drop of particles was held with the underside of the grid at the edge of a polepiece of a 3000 gauss permanent magnet to subject the nanoparticles to a gradient field. After 4 min, the grid was washed as above. Electron microscopy revealed a dense enrichment of particles for the grid held in the magnetic field (FIG. 7). The particles were ~15 nm in size, showing manipulation of nanoparticles at this dimension.

Example 14

Figure 8:
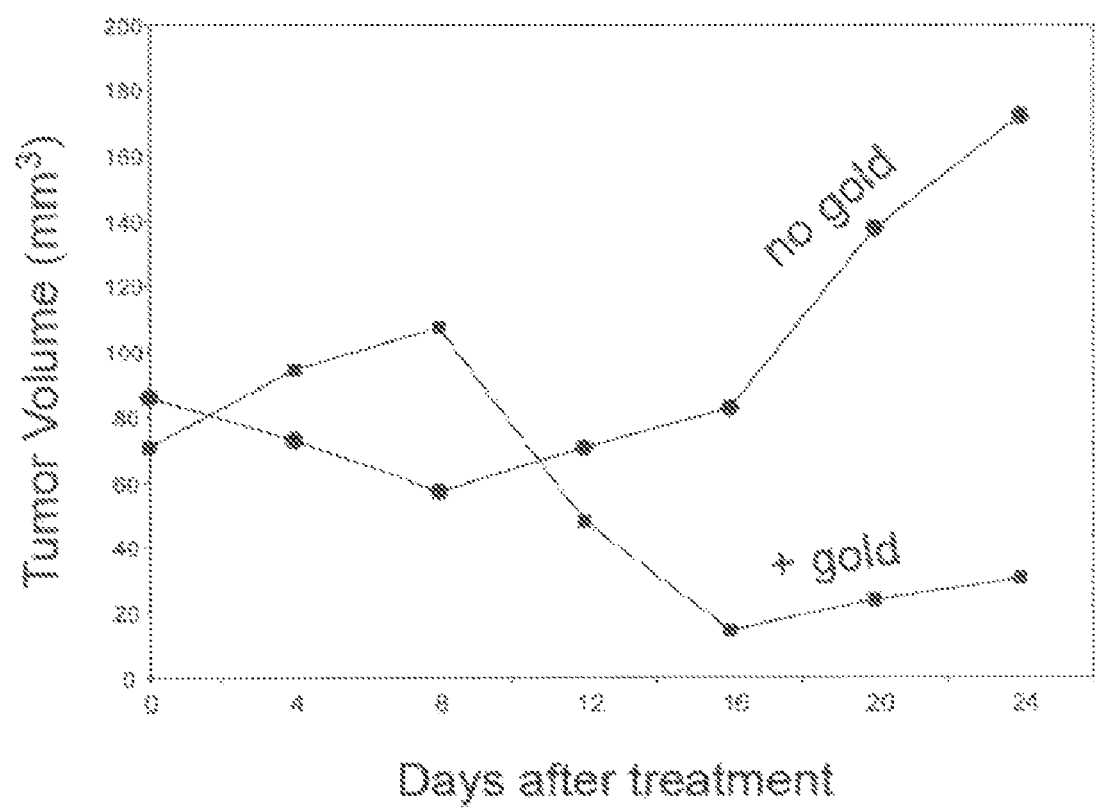
FIG. 8 is an illustrative, non-limiting demonstration of tumor volume of a subcutaneous SCCVII tumor in C3H mice as a function of time after a single radiosurgical treatment of 51 Gy. Prior to the irradiation, the mice were either not treated with any other reagent or were injected with 15 nm coated gold nanoparticles, which were prepared as described in Example 4. The results displayed are obtained from the average of 10 animals in each group.

Radiotherapy Enhancement Using Coated Gold Nanoparticles $2\times10^5$ SCCVII squamous cell carcinoma cells were implanted subcutaneously in the hind leg of C3H mice. When the tumor volume reached 50-100 mm$^3$, the animals were intravenously injected with 830 mg Au/kg of the coated gold nanoparticles that were prepared as described in Example 4. Within 1.5 minutes of administration of the coated gold nanoparticles, the tumor region was irradiated with X-rays with a dose of 51 Gy having a median energy of 157 keV. This particular tumor model has a radiation TCD50 (tumor control dose 50%, dose where 50% of the tumors are cured) of 80 Gy. As shown in FIG. 8, the administration of the coated gold nanoparticles has a significant effect on the reduction of the tumor volume with a radiation dose of 51 Gy.

The examples and embodiments described herein are for illustrative purposes only and various modifications or changes suggested to persons skilled in the art are to be included within the spirit and purview of this application and scope of the appended claims. All publications, patents, and patent applications cited herein are hereby incorporated by reference for all purposes.

What is claimed is:

1. A composition comprising:
a nanoparticle comprising at least one metal in the core of the nanoparticle, the at least one metal selected from titanium, vanadium, chromium, manganese, cobalt, nickel, copper, zinc, zirconium, molybdenum, ruthenium, rhodium, palladium, silver, cadmium, tungsten, rhenium, osmium, iridium, platinum, gold, aluminum, and bismuth, provided that the core of the nanoparticle does not contain iron; the nanoparticle coated with a bilayer of molecules held together by hydrophobic interactions, wherein the bilayer of molecules is formed from:
  (a) a monolayer of surface binding molecules in direct contact with the nanoparticle, comprising:
    (i) a hydrophobic moiety; and
    (ii) a binding moiety having an affinity for the nanoparticle, the binding moiety selected from a thiol moiety, a thiolate moiety, a carboxylate moiety of an unsaturated fatty acid or combinations thereof; and
  (b) a layer of amphiphatic molecules that is different from the surface binding molecules.

2. The composition of claim 1, wherein the monolayer of surface binding molecules of (a) forms a complete monolayer that coats the nanoparticle.

3. The composition of claim 1, wherein the nanoparticle has a diameter of about 1 nm up to about 200 nm.

4. The composition of claim 1, wherein the nanoparticle comprises gold.

5. The composition of claim 1, wherein the binding moiety of the surface binding molecules of (a) has an affinity for the nanoparticle that results in an ionic interaction, covalent bond, or coordination with the nanoparticle.

6. The composition of claim 1, wherein the binding moiety of the surface binding molecules of (a) is selected from among a thiol moiety and a thiolate moiety.

7. The composition of claim 1, wherein the hydrophobic moiety of the surface binding molecules of (a) is selected from among alkyl moieties, alkene moieties, alkyne moieties, aryl moieties, hydrophobic moieties of unsaturated fatty acids, steroid moieties, and combinations thereof.

8. The composition of claim 1, wherein the surface binding molecules of (a) are alkyl thiols.

9. The composition of claim 1, wherein the surface binding molecules of (a) have the same chemical structure.

10. The composition of claim 1, wherein the amphiphatic molecules of (b) comprise a hydrophobic moiety selected from among alkyl moieties, alkene moieties, alkyne moieties, aryl moieties, hydrophobic moieties of fatty acids, steroid moieties, and combinations thereof.

11. The composition of claim 1, wherein the amphiphatic molecules of (b) comprise a hydrophilic moiety selected from among phosphate groups, sulfonate groups, sulfate groups, hydroxyl groups, carboxyl groups, amino groups, amide groups, carbohydrate groups, peptide groups, protein groups, nucleic acid groups, ethylene glycol groups, and combinations thereof.

12. The composition of claim 1, wherein the amphiphatic molecules of (b) have the same chemical structure.

13. A composition comprising:
a nanoparticle comprising at least one metal in the core of the nanoparticle, the at least one metal selected from titanium, vanadium, chromium, manganese, cobalt, nickel, copper, zinc, zirconium, molybdenum, ruthenium, rhodium, palladium, silver, cadmium, tungsten, rhenium, osmium, iridium, platinum, gold, aluminum, and bismuth, provided that the core of the nanoparticle does not contain iron; the nanoparticle coated with a bilayer of molecules held together by hydrophobic interactions, wherein the bilayer of molecules is formed from:
  (a) a monolayer of surface binding molecules in direct contact with the nanoparticle, comprising:
    (i) a hydrophobic moiety; and
    (ii) a binding moiety having an affinity for the nanoparticle; and (b) a layer of amphiphatic molecules that is different from the surface binding molecules; wherein one or more of the amphiphatic molecules comprises a sorbitan moiety.

14. The composition of claim 13, wherein the amphiphatic molecule of (b) is selected from among sorbitan monolaurate, polyoxyethylene (20) sorbitan monolaurate, sorbitan monopalmitate, polyoxyethylene (20) sorbitan monopalmitate, sorbitan monostearate, polyoxyethylene (20) sorbitan monostearate, sorbitan monooleate, polyoxyethylene (20) sorbitan monooleate, and combinations thereof.

* * * * *